(12) United States Patent
Boulton et al.

(10) Patent No.: US 6,297,035 B1
(45) Date of Patent: *Oct. 2, 2001

(54) ERK1 MAP2 PROTEIN KINASE

(75) Inventors: Teri G. Boulton, Irving; Melanie H. Cobb, Dallas, both of TX (US); George D. Yancopoulos, Elmhurst, NY (US); Steven Nye, New York, NY (US); Nikos Panayotatos, Orangeburg, NY (US)

(73) Assignees: Regeneron Pharmaceuticals, Inc., Tarrytown, NY (US); University of Texas, Austin, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/932,012

(22) Filed: Sep. 17, 1997

Related U.S. Application Data

(60) Continuation of application No. 08/462,874, filed on Jun. 5, 1995, now abandoned, which is a division of application No. 08/178,488, filed on Jan. 7, 1994, now abandoned, which is a continuation of application No. 07/701,544, filed on May 16, 1991, now abandoned, which is a continuation-in-part of application No. 07/532,004, filed on Jun. 1, 1990, now abandoned.

(51) Int. Cl.$^7$ .............................. C12N 9/12; C12N 9/10; C12N 15/00; C07H 21/04

(52) U.S. Cl. ..................... 435/194; 435/183; 435/193; 435/320.1; 536/23.2

(58) Field of Search ................................ 435/183, 194, 435/193, 320.1; 530/352; 536/232

(56) References Cited

PUBLICATIONS

Ray, L. B. et al. J. Biol. Chem. 263: 12721–12727, Sep. 1988.*
Hoshi, M. et al. J. Biol. Chem. 263: 5396–5401, Apr. 1988.*
Miyasaka, T. et al. J. Biol. Chem. 265: 4730–4735, Mar. 1990.*
Hanks, S. K. et al. Science 241: 42–52, Jul. 1988.*
Rudinger, J., Peptide Hormones, Parsons (Ed.), University Park Press, Baltimore, MD. pp. 1–7, Jun. 1976.*
Rossomando et al. PNAS 86: 6940–6943 (1989).*
Boulton et al. Cell 65: 663–675 (1991).*

\* cited by examiner

Primary Examiner—Phillip Gambel
(74) Attorney, Agent, or Firm—Linda O. Palladino; Robert J. Corbert; Pennie & Edmonds

(57) ABSTRACT

The present invention relates to a newly identified family of protein serine/threonine kinases which phosphorylate microtubule-associated protein 2 (MAP2). It is based, in part, on the cloning and characterization of novel MAP2 kinases designated extracellular signal-regulated kinase 1, 2, and 3 (ERK1, ERK2, ERK3) which are expressed in the central nervous system, and on the identification of another ERK family member, ERK4, with antisera. The present invention provides for recombinant nucleic acid molecules and proteins representing members of the MAP2 kinase family, and also for microorganisms, transgenic animals, and cell lines comprising recombinant MAP2 kinase molecules. In additional embodiments of the invention, the present invention provides for methods for assaying cellular factor activity, including, but not limited to, nerve growth factor activity, in which the activation of MAP2 kinase serves as an indicator of cellular factor activity. These methods may be extremely useful in screening compounds for the presence of a desired cellular factor activity. In specific embodiments, compounds which may be useful in the treatment of Alzheimer's disease, peripheral neuropathies, and diabetes may be identified using the methods of the invention.

4 Claims, 28 Drawing Sheets

Phenyl Sepharose

ACA-54

DEAE

Q-Sepharose #2

FIGURE 2B-1

Figure 1:
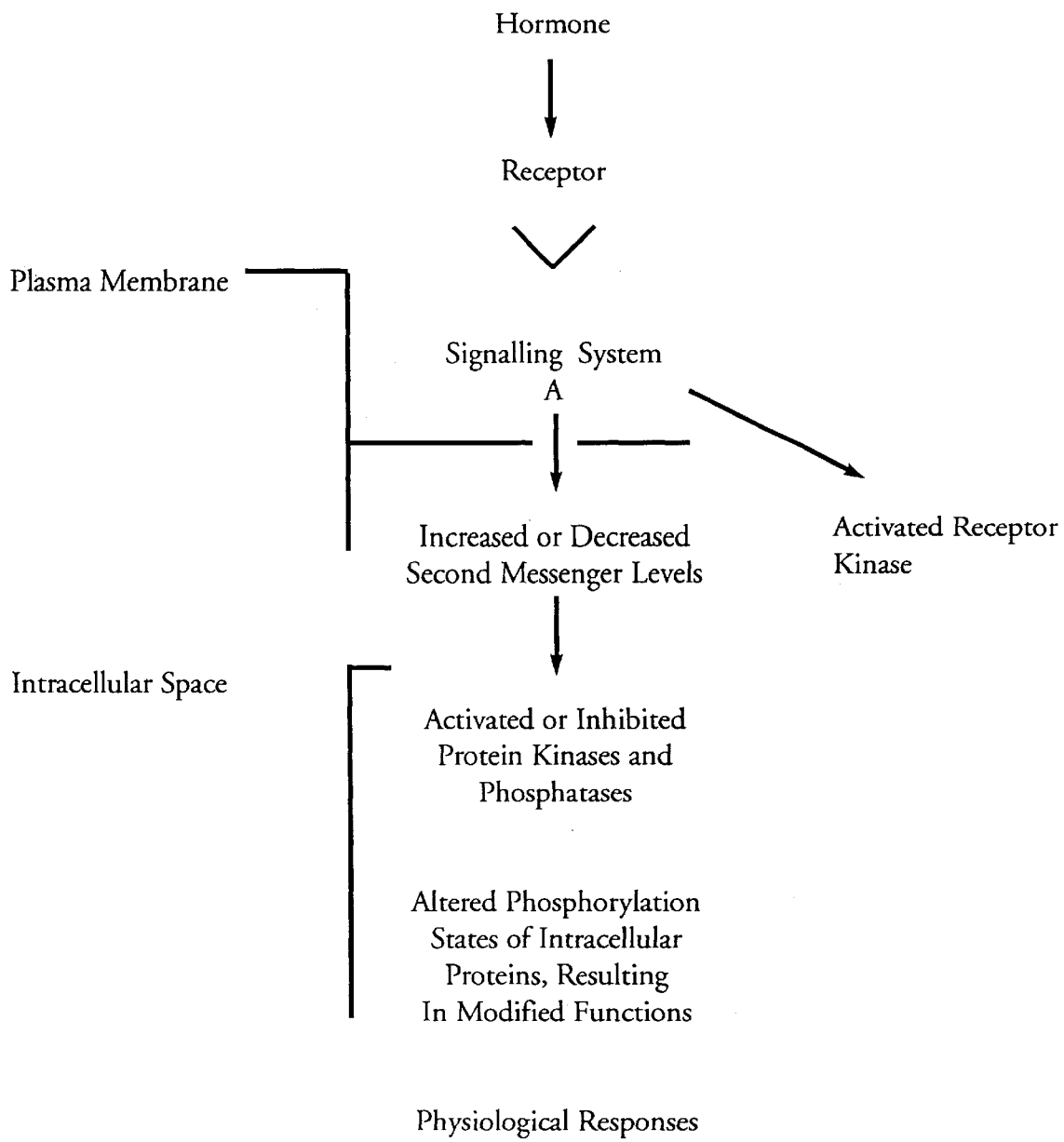

```
                                              Arg Gly Thr Ala Gly Val Val Pro Val Pro Gly Glu Val Glu Val Val
                                              AGG GGA ACT GCT GGG GTC GTG CCG GTC CCC GGG GAG GTG GAG GTG GTG

Lys Gly Gln Pro Phe Asp Val Gly Pro Arg Tyr Thr Gln Leu Gln Tyr Ile Gly Glu Gly Ala Tyr Gly Met Val Ser Ser
AAG GGG CAG CCA TTC GAC GTG GGC CCA CGC TAC ACG CAG CTG CAG TAC ATC GGC GAG GGC GCG TAC GGC ATG GTC AGC TCA
                                               *                                                    *

Ala Tyr Asp His Val Arg Lys Thr Arg Val Ala Ile Lys Lys Ile Ser Pro Phe Glu His Gln Thr Tyr Cys Gln Arg Thr
GCA TAT GAC CAC GTG CGC AAG ACC AGA GTG GCT ATC AAG AAG ATC AGC CCC TTC GAG CAT CAA ACC TAC TGT CAG CGC ACG

Leu Arg Glu Gln Ile Leu Leu Gly Phe Arg His Glu Asn Val Ile Gly Ile Arg Asp Ile Leu Arg Ala Pro Thr Leu
CTG AGA GAA ATC CAG ATC TTG CTC GGA TTC CGC CAT GAG AAT GTC ATA GGC ATC CGA GAC ATC CTC AGA GCA CCC ACC CTG

Glu Ala Met Arg Asp Val Tyr Ile Val Gln Asp Leu Met Glu Thr Asp Leu Tyr Lys Leu Leu Lys Ser Gln Gln Leu Ser
GAA GCC ATG AGA GAT GTT TAC ATT GTT CAG GAC CTC ATG GAG ACG GAC CTG TAC AAG CTA AAG AGC CAG CAG CTG AGC

Asn Asp His Ile Cys Tyr Phe Leu Tyr Gln Ile Leu Arg Gly Leu Lys Tyr Ile His Ser Ala Asn Val Leu His Arg Asp
AAT GAC CAC ATC TGC TAC TTC CTC TAC CAG ATC CTC CGG GGC CTC AAG TAC ATA CAC TCG GCC AAT GTG CTG CAC CGG GAC
                                                                                  *                     *

Leu Lys Pro Ser Asn Leu Leu Ile Asn Thr Thr Cys Asp Leu Lys Ile Cys Asp Phe Gly Leu Ala Arg Ile Ala Asp Pro
CTG AAG CCC TCC AAT CTG CTT ATC AAC ACC ACC TGC GAC CTT AAG ATC TGT GAT TTT GGC CTT GCC CGG ATT GCT GAC CCT
                              *                                                    *                    *

Glu His Asp His Thr Gly Phe Leu Thr Glu Tyr Val Ala Thr Arg Trp Tyr Arg Ala Pro Glu Ile Met Leu Asn Ser Lys
GAG CAC GAC CAC ACT GGC TTT CTG ACC GAG TAT GTG GCC ACA CGC TGG TAC CGA GCC CCA GAG ATC ATG CTT AAC TCC AAG
                                                                      *

Gly Tyr Thr Lys Ser Ile Asp Ile Trp Ser Val Gly Cys Ile Leu Ala Glu Met Leu Ser Asn Arg Pro Ile Phe Pro Gly
GGC TAC ACC AAA TCC ATT GAC ATC TGG TCT GTG GGC TGC ATT CTG GCT GAG ATG CTC TCC AAC CGG CCT ATC TTC CCC GGC
```

FIGURE 2B-2

```
Lys His Tyr Leu Asp Gln Leu Asn His Ile Leu Gly Ile Leu Gly Ser Pro Ser Gln Glu Asp Leu Asn Cys Ile Ile Asn
AAG CAC TAC CTG GAC CAG CTC AAC CAC ATT CTA GGT ATA CTG GGT TCC CCA TCC CAA GAG GAC CTA AAT TGT ATC ATT AAC

Met Lys Ala Arg Asn Tyr Leu Gln Ser Leu Pro Ser Lys Thr Lys Val Ala Trp Ala Lys Leu Phe Pro Lys Ser Asp Ser
ATG AAG GCC CGA AAC TAC CTA CAG TCT CTG CCC TCT AAA ACC AAG GTG GCT TGG GCC AAG CTT TTT CCC AAA TCT GAC TCC
                                                                            *
Lys Ala Leu Asp Leu Leu Asp Arg Met Leu Thr Phe Asn Pro Asn Lys Arg Ile Thr Val Glu Glu Ala Leu Ala His Pro
AAA GCT CTT GAC CTG CTG GAC CGG ATG TTA ACC TTT AAC CCA AAC AAG CGC ATC ACA GTA GAG GAA GCA CTG GCT CAC CCT

Tyr Leu Glu Gln Tyr Tyr Asp Pro Thr Asp Glu Pro Val Ala Glu Glu Pro Phe Thr Phe Asp Met Glu Leu Asp Asp Leu
TAC CTG GAA CAG TAC TAT GAT CCG ACA GAT GAA CCA GTG GCT GAG GAG CCA TTC ACC TTT GAC ATG GAG CTG GAT GAT CTC

Pro Lys Glu Arg Leu Lys Glu Leu Ile Phe Gln Glu Thr Ala Arg Phe Gln Pro Gly Ala Pro Glu Ala Pro END CAAGAAC
CCC AAG GAG CGG CTG AAG GAG CTG ATC TTC CAA GAG ACA GCC CGC TTC CAG CCA GGG GCA CCA GAG GCC CCC TAA

AGACACCCCTGTCCTTTGGACCTGTCTGCTCTACCTGCTCCTTCTCTGCAGATTGTTAGAAAATGAACTTGCTCAACCCGGACCCCGGCAGCCCCAGGCTGGACC

AAGGGTGGGCCTGGCACCCCTCTCACTCTGCTGGGTCTTCCTCCTGTTCAAGAGCTTCTCCCACTCCAGTCCCCTGCCCCATCTCCCCTGACCTGAGTGATGAGGTG

GTCCCAGAGCTGATCTCTGCTGTCTTTATCTATCCCTGCTAGCCCCCAGCTCGGTTCTGGAATGGAAGGGCTTCTGACCGCCCTAGGACCTGTGCT

ACAGAGGGGTGGAGGGCACTGAGTAGGCTAAGCTCTGCCCTACTCATCCTCGTTGGAACCCCACCCCATTTCCCTGACAGAACATTCCTAAATCTCAAGGGCTAGTT

TCCCTGAGGAGCCAGCCTAACCCCTCTCCCTCTCAAGCTGCCACATGTAACGCCCTTGCTGCTTCTGTGTGGGTGATTGGATGTGGAGGCGGGGCCCGTG

GAGAGCCCGTGCCCTCCCCACTCCCTGTATCTAATATATAAATATAGAGATGTGTATATGGAAAAAAAAAAAAAAAAAAAAAAAAAAAAAAAA
```

FIGURE 3A-1

FIGURE 3A-2

```
  *   *
  Phe Gly Leu Ala Arg Val Ala Asp Pro Asp His Thr Gly Phe Leu Thr Glu
  TTT GGC CTT GCC CGT GTT GCA GAT CCA GAC CAT CAT ACA GGG TTC TTG ACA GAG

*     *
  Tyr Val Ala Thr Arg Trp Tyr Arg Ala Pro Glu Ile Met Leu Asn Ser Lys Gly
  TAT GTA GCC ACG CGT TGG TAC AGA GCT CCA GAA ATT ATG TTG AAT TCC AAG GGT    777

*           IX  *
  Tyr Thr Lys Ser Ile Asp Ile Trp Ser Val Gly Cys Ile Leu Ala Glu Met Leu Ser
  TAT ACC AAG TCC ATT GAT ATT TGG TCT GTG GGC TGC ATC CTG GCA GAG ATG CTA TCC

Asn Arg Pro Ile Phe Pro Gly Lys His Tyr Leu Asp Gln Leu Asn His Ile Leu
  AAC AGG CCT ATC TTC CCA GGA AAG CAT TAC CTT GAC CAG CTG AAT CAC ATC CTG    888
                X
  Gly Ile Leu Gly Ser Pro Ser Gln Glu Asp Leu Asn Cys Ile Ile Asn Leu Lys Ala
  GGT ATT CTT GGA TCT CCA TCA CAG GAA GAT CTG AAT TGT ATA ATA AAT TTA AAA GCT

Arg Asn Tyr Leu Leu Ser Leu Pro His Lys Asn Lys Val Pro Trp Asn Arg Leu
  AGA AAC TAT CTT CTT TCT CTC CCG CAC AAA AAT AAG GTG CCG TGG AAC AGG TTG    999
                                                                          XI
  Phe Pro Asn Ala Asp Ser Lys Ala Leu Asp Leu Leu Asp Lys Met Leu Thr Phe Asn
  TTC CCA AAC GCT GAC TCC AAA GCT CTG GAT TTA CTG GAT AAA ATG TTG ACA TTT AAC

*
  Pro His Lys Arg Ile Glu Val Glu Gln Ala Leu Ala His Pro Tyr Leu Glu Gln
  CCT CAC AAG AGG ATT GAA GTT GAA CAG GCT CTG GCC CAC CCG TAC CTG GAG CAG    1110

Tyr Tyr Asp Pro Ser Asp Glu Pro Ile Ala Glu Pro Phe Lys Phe Asp Met Glu
  TAT TAT GAC CCA AGT GAT GAG CCC ATT GCT GAA GCA CCA TTC AAG TTT GAC ATG GAG

Leu Asp Asp Leu Pro Lys Glu Lys Leu Lys Glu Leu Ile Phe Glu Glu Thr Ala
  CTG GAC GAC TTA CCT AAG GAG AAG CTC AAA GAA CTC ATT TTT GAA GAG ACT GCT    1221

Arg Phe Gln Pro Gly Tyr Arg Ser END
  CGA TTC CAG CCA GGA TAC AGA TCT TAA  ATTGGTCAGGACAAGGGCTCAGAGGACTGGACGCGTTCA

GATGTCGGTGTCCCCCCAGTTCTTGACCCTGTCCTGTGTCCTGTCTCCAGCTTACCCACTCTTGACTC       1359

CTTTGAGCCGTTCCGAGGGCAGTCTGGCTGTCGTAGTGGCTTTTATACTTTCACGGAATTCTTCAGTCCAGAGAGTT

CTCCTGCACCAGGCCCTGCACAGTTGCACTCAG                                          1467
```

FIGURE 3B-1

```
AGACCTGCCGGGCGCATATTATTCACAGTTTGTCCCATGTAAGTCGTTAGCATAGTGAATCGAGTGCATAGTATG
TCATTTCATTCCGTTGAGTTGTTTTCTTCTTTAAATGTCTGCAGAGTCGCTACCCTTCCTTGAACTATGAAGCAC  160

TGCAATCTTCTTAATTCTCAGTATGAAGAGAGATTTTGAGCTTTAAGTCTGAGGGAACTCAGCAGGCCTGGTTGGCGT
                                                            END  Glu Ile Phe Pro
CTGCAATGAACATCAAGAAACCATCGTCTGTGGGAATGTGATCGTTTTCTCCCTTTT  TGA  GAG ATC TTT CCT  314

Phe Asp Ala Ser Phe Leu Pro Cys Leu His Lys Phe Asn Asn Leu Lys Phe Asn Lys Gly Asn
TTT GAT GCC AGT TTT CTT CCT TGT CTT TTA CAC AAG TTC AAC AAT TTG AAA GGA AAA GGC AAT

Cys Lys Gly Phe Lys  MET  Ala Glu Glu Phe Ser Leu Met Asn Ile His Gly Phe Asp
TGT AAG GGT TTT AAG  ATG  GCA GAG GAG TTT GAA AGT CTC ATG AAC ATT CAT GGC TTT GAT  434
                                                                              *
Leu Gly Ser Arg Tyr Met Asp Leu Lys Pro Leu Gly Cys Gly Asn Gly Leu Val Phe
CTG GGT TCC AGG TAC ATG GAC TTA AAA CCA TTG GGC TGT GGT GGA GGC TTG GTT TTT
                                                  *  I
Ser Ala Val Asp Asn Asp Cys Asp Lys Arg Val Ala Ile Lys Lys Ile Val Leu Thr Asp
TCT GCT GTA GAC AAT GAC TGT GAC AAG AGA GTA GCC ATC AAG AAA ATT GTC CTC ACC GAT  554
                                    II              *
Pro Gln Ser Val Lys His Ala Leu Ile Lys Ile Ile Arg Arg Leu Asp His Asp
CCC CAG AGT GTC AAA CAT GCC CTC AAA ATT AAA ATT AGA AGA CTT GAC CAC GAT
                III  *
Asn Ile Val Lys Val Phe Glu Ile Leu Gly Pro Ser Gln Leu Thr Asp Asp Val
AAC ATT GTG AAA GTG TTT GAA ATT CTT GGT CCC AGT GGA AGC CAG CTG ACA GAC GAT GTG  674
            IV                                                          V
Gly Ser Leu Thr Glu Leu Asn Ser Val Tyr Ile Val Gln Glu Tyr Met Glu Thr Asp Leu
GGC TCT CTA GAG ACA GAG CTG AAT AGC GTC TAC ATT GTT CAG GAG TAC ATG GAG ACA GAC TTG

Ala Asn Val Leu Glu Gln Gly Pro Leu Glu Glu His Ala Arg Leu Phe Met Tyr Gln
GCG AAC GTG CTG GAG CAG GGC CCT TTA CTG GAG GAG CAT GCC AGG CTC ATG TAC CAG  794
                    VI                                                *
Leu Leu Arg Gly Leu Lys Tyr Ile His Ser Ala Asn Val Leu His Arg Asp Leu Lys Pro
CTG CTG CGT GGG CTC AAG TAC ATC CAC TCT GCA AAC GTG CTG CAC AGG GAT CTC AAG CCG
                           VII                          *  *
Ala Asn Leu Phe Ile Asn Thr Glu Asp Leu Val Leu Lys Ile Gly Asp Phe Gly Leu Ala
GCC AAC CTT TTC ATT AAC ACT GAA GAC TTG GTG AAG ATT GGT GAC TTT GGC CTG GCC  914
 *
```

FIGURE 3B-2

```
                                                              VIII
Arg Ile Met Asp Pro His Tyr Ser His Lys Gly His Leu Ser Glu Gly Leu Val Thr Lys
CGG ATC ATG GAT CCT CAT TAT TCC CAT AAG GGT CAT CTT TCT GAA GGA TTG GTT ACC AAA  1034
              *         #                                                *
Trp Tyr Arg Ser Pro Arg Leu Leu Ser Pro Asn Asn Tyr Thr Lys Ala Ile Asp Met
TGG TAC AGA TCT CCA CGG CTT TTA TCT CCT AAT AAC TAT ACT AAA GCC ATT GAC ATG  1034
 IX       *         *
Trp Ala Gly Cys Ile Phe Ala Glu Met Leu Thr Gly Lys Thr Leu Phe Ala Gly Ala
TGG GCT GGC TGC ATC TTT GCT GAA ATG CTG ACT GGT AAA ACC CTC TTT GCA GGT GCA  1154

His Glu Leu Glu Gln Met Gln Leu Ile Leu Thr Leu Glu Ser Ile Pro Val His Glu Asp
CAT GAA CTT GAA CAG ATG CAG CTG ATC TTG ACT CTG GAG TCT ATC CCT GTG CAC GAG GAT
                                                           X

Arg Gln Glu Leu Leu Ser Val Ile Pro Val Tyr Ile Arg Asn Asp Met Thr Glu Pro His
CGG CAG GAG CTT CTC AGC GTG ATT CCA GTT TAC ATT AGA AAC GAC ATG ACT GAG CCA CAC  1274

Lys Pro Leu Thr Gln Leu Pro Gly Ile Ser Arg Glu Ala Leu Asp Phe Leu Glu Gln
AAA CCG CTG ACT CAG CTG CCG GGG ATT AGT CGG GAA GCA CTG GAT TTC CTG GAA CAG
                    *

Ile Leu Thr Phe Ser Pro Met Asp Arg Leu Thr Ala Glu Glu Ala Leu Ser His Pro Tyr
ATT CTG ACG TTC AGT CCC ATG GAC CGG CTG ACA GAG GAA GCA CTT TCC CAT CCT TAC
         XI

Met Ser Ile Tyr Ser Phe Pro Thr Asp Glu Pro Ile Ser Ser His Pro Phe His Ile Glu
ATG AGC ATC TAC TCT TTC CCA ACG GAC GAG CCT ATT TCC AGC CAT CCT TTC CAC ATA GAA  1394

Asp Glu Val Asp Asp Ile Leu Leu Met Asp Glu Thr His Ser Gly Thr His Ile Tyr Asn Trp Glu
GAC GAA GTG GAC GAC ATT TTG CTA ATG GAT GAA ACA CAC AGT GGT ACA CAC ATT TAT AAC TGG GAA
```

FIGURE 3B-3

```
Arg Tyr His Asp Cys Gln Phe Ser Glu His Asp Trp Pro Ile His Asn Asn Phe Asp Ile
AGG TAC CAC GAT TGT CAG TTC TCG GAG CAT GAC TGG CCT ATT CAT AAC AAC TTT GAT ATC 1514

Asp Glu Val Gln Leu Asp Pro Arg Ala Leu Ser Asp Val Thr Asp Glu Glu Val Gln
GAT GAG GTT CAG CTT GAC CCG AGA GCT CTG TCT GAT GTC ACC GAT GAA GAA GTT CAA

Val Asp Pro Arg Lys Tyr Leu Asp Gly Asp Arg Glu Lys Tyr Leu Glu Asp Pro Ala Phe 1634
GTT GAT CCT CGA AAG TAC TTG GAT GGA GAC CGA GAG AAG TAT CTG GAG GAT CCC GCC TTC

Asp Thr Ser Tyr Ser Ala Glu Pro Cys Trp Gln Tyr Pro Asp His His Glu Asn Lys Tyr
GAC ACC AGC TAC TCT GCT GAG CCT TGC TGG CAG TAC CCA GAT CAC CAC GAG AAC AAG TAC

Cys Asp Leu Glu Cys His Thr Cys Asn Tyr Lys Thr Arg Ser Pro Ser Tyr Leu Asp 1754
TGT GAT CTG GAG TGT CAC ACC TGT AAC TAC AAA ACA AGG TCG CCA TCA TAC TTA GAT

Asn Leu Val Trp Arg Glu Ser Glu Val Asn His Tyr Tyr Glu Pro Lys Leu Ile Ile Asp
AAC CTG GTG TGG AGG GAG AGC GAG GTT AAC CAT TAC TAT GAG CCC AAG CTT ATT ATA GAT

Leu Ser Asn Trp Lys Glu Gln Ser Lys Asp Lys Arg Gly Lys Ser Lys Cys 1874
CTT TCC AAC TGG AAA GAG CAA AGT AAG GAC AAA TCC AGG AAG TCC AAG TGT

Glu Arg Asn Gly Leu Val Lys Arg Arg Leu Arg Lys Arg Pro Ser Ser Trp Leu
GAG AGG AAC GGG TTG GTC AAG CGC AGA TTG CGG AGG AAG CGT CCC AGC TGG CTG

Arg Gly Arg Gly Ala Lys Ala Leu Thr Leu Met Pro Ser Ser Gln Ala Pro Phe Ser Ser
AGA GGG AGA GGG GCC AAG GCT TTG ACT TTG ATG CCT TCA TCG CAG GCA CCG TTC AGC TCA 1994

Val Pro Ser Val Ser Leu Leu Thr END
GTG CCC AGC GTG AGT CTG CTG ACG TAG TTGACAAGTTAAACGACTTGAATAGCTCAGTGTCCCAGCTAGAA
ATGAAAAGCCTGATATCCAAGTCAGTCAGCCGAGAACCAAGAAAAGGAAGGCTAACCTGGCCCAGCTGCAGTTTGTGTGAGGTCA 2145

GTACCAGCCCTCCTGGGAGAGCCAGTTTGTGAGTGGCGGGAGGAGTGCTTCCTTATCAGTCAGTCAGTTTGTGTGAGGTCA
GGAAGGACGAACACGTGGAGAAGGAGAACACTTACACCAGCTATTTGGACAAGTTTTTTAGCAGGAGGAGATTCTGAA 2305
```

FIGURE 3B-4

```
ATGCTAGAAACTGAGCCAGTGGAAGAAGGGAAGCGTGGGAGAGAGGCCGTGAGGCAGGGCTTCTGAGCAGGCGGTGGGA
GTTTCCTGAGCAGGCAGCTAGAGTCCATAGGCAGCCCCGCCAGTCCCAGGGGATCCCACTCAAGTCCCATCC      2465
AGGCCACGTTAACACCTTCCGCTATGAAATCTTCCCCTCAAATCCCTCACAAGACATACAGCAACATTCTGAAACATCTG
AACTAAACACTCAGCAGACACTTCTTTTGTCTTTTATCACTAAGTGTTTAAGTCATT                      2625
TTTTTTACTTGAATCAGAAGGTGTCATTAATTGCAAGGATTTTCTTGGTTCTCAGTTTGTAAAACACAGAGTTTT
TCTACATGTGAGTTAGTTTCATTGAACTGGCATGTCGTTTGCACACACAAAGAATAGAGCAAAACAATGCAGTGCA    2785
GGAGGAGACAAGATGCGCTAGGATGGACAGACATTCTCACAGACCAGTGACCTGCTTACAGGAAACAAAACCTGCCTTG
AAACTTACACAGTGAGACTGTACATAATTGCATGAAAAGATCTATTTTTCCTGAAACATTTTCATTCATTAGTATTT    2945
TCAAGTTTTTCATACTGTACACATTTCTAAGACACATGATACCAGCAGCAACTGAAAACGAATGCCGAATTGGTACAC
ATGTGTTATCTACCTCAAGTAACAAAGTATGCGGGCGAAACCTAACCACCATATCAATGTCGTCGCGGCATATGCACTTG 3105
TATCTAGCCAGCGTTGGCCGCAGTAACCAATGAGACTCGTCCGCCATTTATCAATGTCCTGGTGTTCATCCTCCTTTACAGTG
AAGTGTTAGATACATCATTATTATCTTTAGCAAATCAGTATATTTCTGTATTAATTATAAAGGTAACTTAGT         3265
TTAAGTTTATTGCAACTGCCCTTCTCCCGTTGGCACTATGGTTTGTTGCCTGCCGAGCTGATCTGAGAAGTCAGCTT
GTCCCGAGGCTGCCATGTCCATGTACGTTAAGTAAAGTGCTCACTGTGTATAGGAATCTGTATTTTGGAGGTGCTTGATCTATCT 3420
ACAAAGAAAAAATTAGGAATTTATTATAAAATGCTCCTAGAAGTCTTAATGGTGTTTATTTTTAAAACCTTGTAATGT
TAGACTTGTGTGCATGGAAGTGATTAAGGTACATTGTAGTTTGAACATTGTACATGATAAGCCTTCCCCACCC      3585
CCGTTTTACTGTATGTTTTATTGAATGATCTATTCCCATCCCTAGGCAAGCATGAATAAAATTAGGTTAAATGTAAA
AAAAAA                                                                         3671
```

FIGURE 3C-1

FIGURE 3C-2

```
                                                                                        IV
ERK1    Glu Ile Gln Ile Leu Leu Gly Phe Arg His Glu Asn Val Ile Gly Ile Arg   297
        GAA ATC CAG ATC TTG CTC GGA TTC CGC CAT GAG AAT GTC ATA GGC ATC CGA
            Thr                 Arg
ERK1Ψ   ... ..C ... ..A ... ... ... ..G C.. ... ... ... ... ... ... ... ...

ERK1    Asp Ile Leu Arg Ala Pro Thr Leu Glu Ala Met Arg Asp Val Tyr Ile
        GAC ATC CTC AGA GCA CCC ACC CTG GAA GCC ATG AGA GAT GTT TAC ATT
ERK1Ψ   ... ... ... ... ... ... ... ..T ... ... ... ... ... ... ... ...

V
ERK1    Val Gln Asp Leu Met Glu Thr Asp Leu Tyr Lys Leu Leu Lys Ser Gln Gln
        GTT CAG GAC CTC ATG GAG ACG GAC CTG TAC AAG CTG CTA AAG AGC CAG CAG
                                Asp
ERK1Ψ   ... ... ... ... ... ... ..T ..A ... ... ... ..T ... ... ... ..A ...   396

ERK1    Leu Ser Asn Asp His Ile Cys Tyr Phe Leu Tyr Gln Ile Leu Arg Gly
        CTG AGC AAT GAC CAC ATC TGC TAC TTC CTC TAC CAG ATC CTC CGG GGC
                                        Phe
ERK1Ψ   ... ... ... ... ... ... ... ... ... ..T ... ... ... ... ... ...

VI
ERK1    Leu Lys Tyr Ile His Ser Ala Asn Val Leu His Arg Asp Leu Lys Pro Ser
        CTC AAG TAC ATA CAC TCG GCC AAT GTG CTG CAC CGG GAC CTG AAG CCC TCC
                                                    *
ERK1Ψ   ... ... ... ... ... ... ... ... ... ... ... ... ... ... ... ... ...   495

VII                                *   *   *
ERK1    Asn Leu Leu Ile Asn Thr Thr Cys Asp Leu Lys Ile Cys Asp Phe Gly Leu Ala
        AAT CTG CTT ATC AAC ACC ACC TGC GAC CTT AAG ATC TGT GAT TTT GGC CTT GCC
        *                           END
ERK1Ψ   ... ... ... ... ... ... ... ... ..A ... ... ... ... ... ... ... ..G ...
```

FIGURE 4A-1

```
                       I                                                    II
ERK1   EPRGTAGVVPVPGEVEVVKGQPFDVGPRYTQLQYIGEGAYGMVSSAYDHVRKTRVAIKKISPFEHQT-YCQRTLRE
ERK2         MAAAAAGP.M.R.V........N.S.............C......NLN.V................
ERK3             MAEKFESLMNIHG..L.S..MD.KPL.C.GN.L.F..V.NDCDK......VLTDP.S--VKHA...
FUS3                 MPKRIVYNISSDFQLKSLL......V.C..THKPTGEI........E..DKPL-FAL.....
KSS1                  MARTIT..IPSQ.KLVDL........T.C..IHKPSGIK......Q..SKKL-FVT..I..
hCDC2                           MED..KIEK....T..V.YKGRHKTTGQV..M...RLESEEGVPSTAI..

III                          IV                        V
ERK1   IQILLGFR-HENVIGIRDILRAPTL----EAMRDVYIVQDLMETDLYKLLKSQ-----Q            125
ERK2   .K...R..-....I...N..I....I.....Q.K.................T.-----H            118
ERK3   .K.IRRLD--D.IVKVFE..GPSGSQVGSLTELNS.....EY......ANV.EQG-----P           123
FUS3   .K..KH.K-..I.T.FN.Q.PDSF-----NFNE...I.E..Q..HRVIST.----M                108
KSS1   .KL.RY.HE..I.S.L.KV.PVSI-----DKLNA..L.EE.....Q.VINN.NSGFST              114
hCDC2  .SL.KEL.-.P.IVSLQ.V.MQD------------SRL.LIFEFLSM.K.Y.D.IPPGQ-Y            99

VI                              VII
ERK1   LSNDHICYFLYQILRGLKYIHSANVLHRDLKPSNLLINTT-CDLKICDFGLARIADPEHD-------
ERK2   ...........................................L..................---
ERK3   .LEE.ARL.M..L..............A..F..EDLV...G......V...D..-------
ERK3   ..D...Q..I..T..AV.VL.GS..I...........SN-...V........M..HYS-------
FUS3   ..D..VQ.T.....A..S...Q.I......I......L.SN-...V.......I.ESAADNSEPTG
KSS1   .................Q.IVFC..RR..........Q......CLASSS.---SRET
hCDC2  MDSSLVKSY.....Q.IVFC..RR..........Q.....DDK-GTI.LA.....AFG-------I
```

FIGURE 4A-2

```
              VIII                                  IX                                    X
ERK1    HTGFLTEYVATRWYRAPEIMLNSKGYTKSIDIWSVGCILAEMLSNRPIFPGKHYLDQLNHILGILGSP-SQEDLNC    259
ERK2    .........................................................-              252
ERK3    .K.H.S.GLV.K...S.RLL.SPNN...A..M.AA..F...TGKTL.A.A.E.E.MQL..ESIPVV-HE..RQE    258
FUS3    QQSGM...............V..T.AK.SRAM.V..C........LFLR......RD.RH..LL.F..I.T.H.DN..R.    250
KSS1    LV..M.............TFQE..TAM......C........V.GK.L...RD.HH..WL..EV..T--F..F.Q    252
hCDC2   PIRVY.H..V.L...S..VL.G.AR.STPV....I.T.F..LATKK.L.H.DSEI...FR.FRA..T.-NN.VWPE    230

XI
ERK1    IINMKARNYLQSLPSKTKVAWAKLFPKSD--SKALDLLDRMLTFNPNKRITVEEALAHPYLEQYDPTDEP
ERK2    ..L......L..H.N..P.NR..NA.-....K......H..E.Q........S...
ERK3    LLSV-IPV.IRNDMTEPHKPLTQ.L.GIS--RE...F.EQI...S.MD.L.A....S...MSI.SF.....
FUS3    .ESPR..E.IK...MYPAAPLE.M..RVN--P.GI...Q...V.D.A....AK...E....QT.H..N...
KSS1    .KSKR.KE.IAN..MRPPLP.ETVWS.T.LNPDMI....K..Q...D..SAA....R....AM.H..S...
hCDC2   VESL--QD.KNTF.KWKPGSL.SHVKNL.--ENG....SK..IYD.A...SGKM..N...FNDLDNQIKKM    297

ERK1    VAEE-------PFTFDMELDD-LPKERLKELIFQETARFQPGAPEAP                              367
ERK2    I..A--------..K.........-....K......E......YRS                              358
ERK3    ISSH--------...HIED.V..I.LMDETHSH.Y-NWE.YHDCQFSEHDWPIHNNFDIDEVQLDPRAL        387
FUS3    EG..PIPPSF------..E..HHKEA...TTKD..K..WN.IFS                                 353
KSS1    EYPPLNLDDEFWKLDNKIMRPE..EEE-V.I.M..DMLYD.LMKTME                              368

ERK3    SDVTDEEEVQVDPRKYLDGDREKYLEDPAFDTSYSAEPCWQYPDHHENKYCDLECSHTCNYKTRSPSYLDN      528
ERK3    LVWRESEVNHYYEPKLIIDLSNWKEQSKDKSDKRGKSKCERNGLVKRRLRLRKRPSSWLRGRGAKALTLMPS     543
ERK3    SQAPFSSVPSVSLLT
```

FIGURE 4B

|      | ERK1 | ERK2 | ERK3 | FUS3 | KSS1 | CDC2 |
|------|------|------|------|------|------|------|
| ERK1 | 100  | 90   | 50   | 56   | 56   | 41   |
| ERK2 |      | 100  | 51   | 55   | 57   | 41   |
| ERK3 |      |      | 100  | 36   | 37   | 26   |
| FUS3 |      |      |      | 100  | 57   | 30   |
| KSS1 |      |      |      |      | 100  | 31   |
| CDC2 |      |      |      |      |      | 100  |

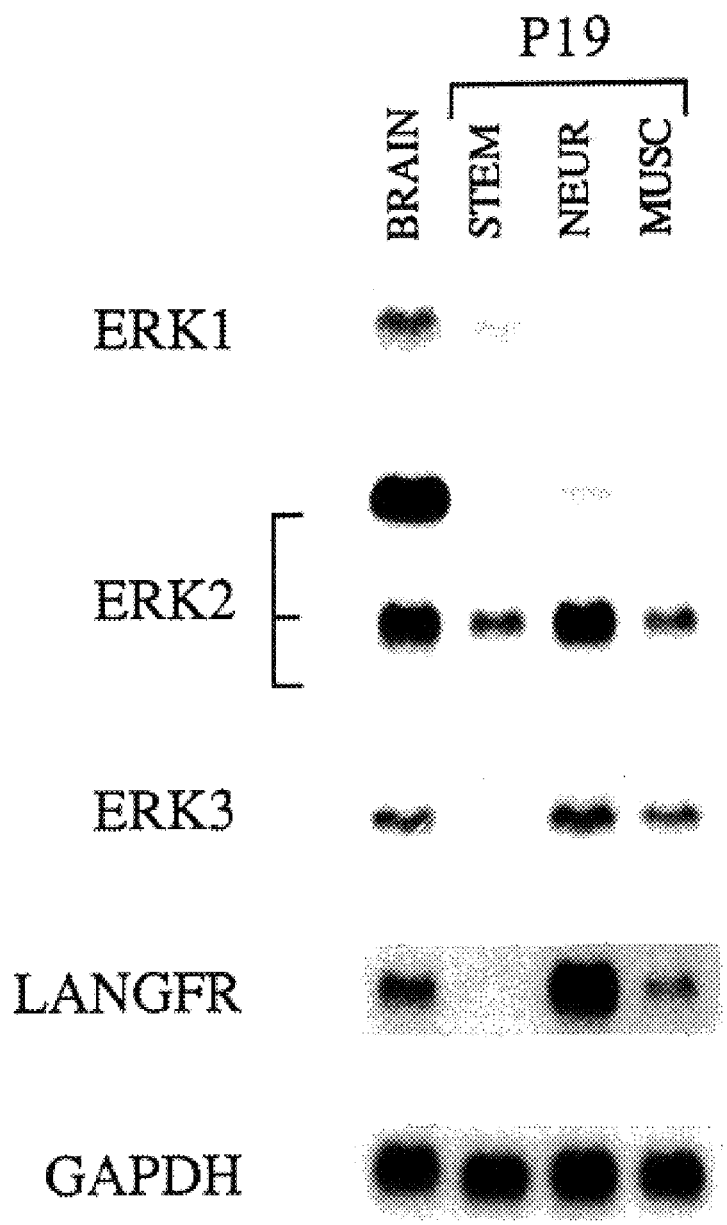

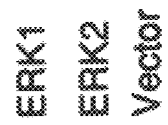
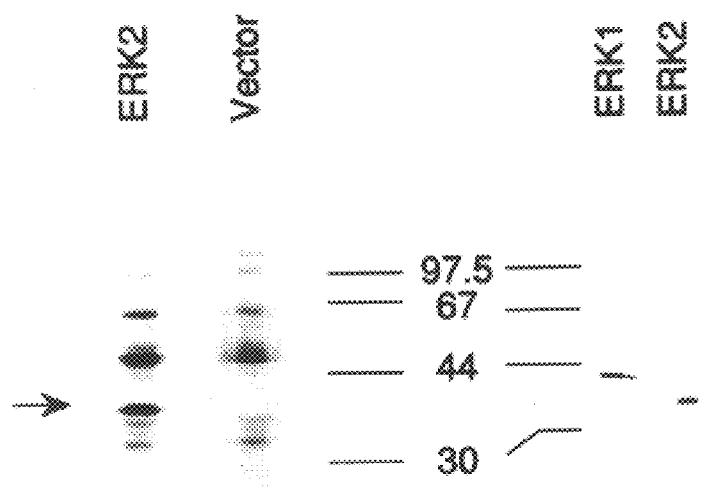
Figure 7A
Figure 7B
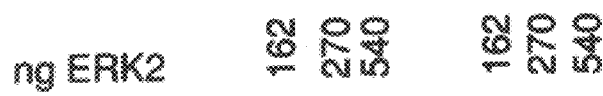
Figure 7C
Figure 7D
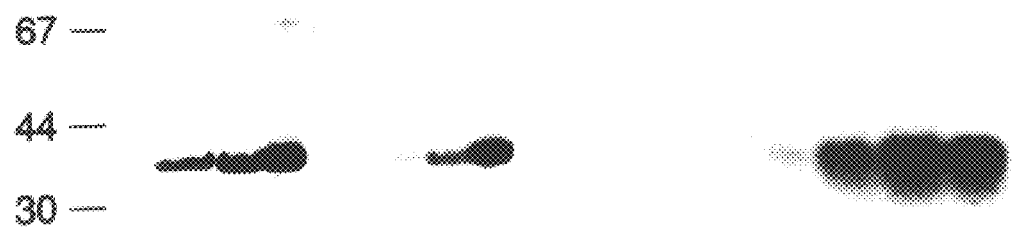

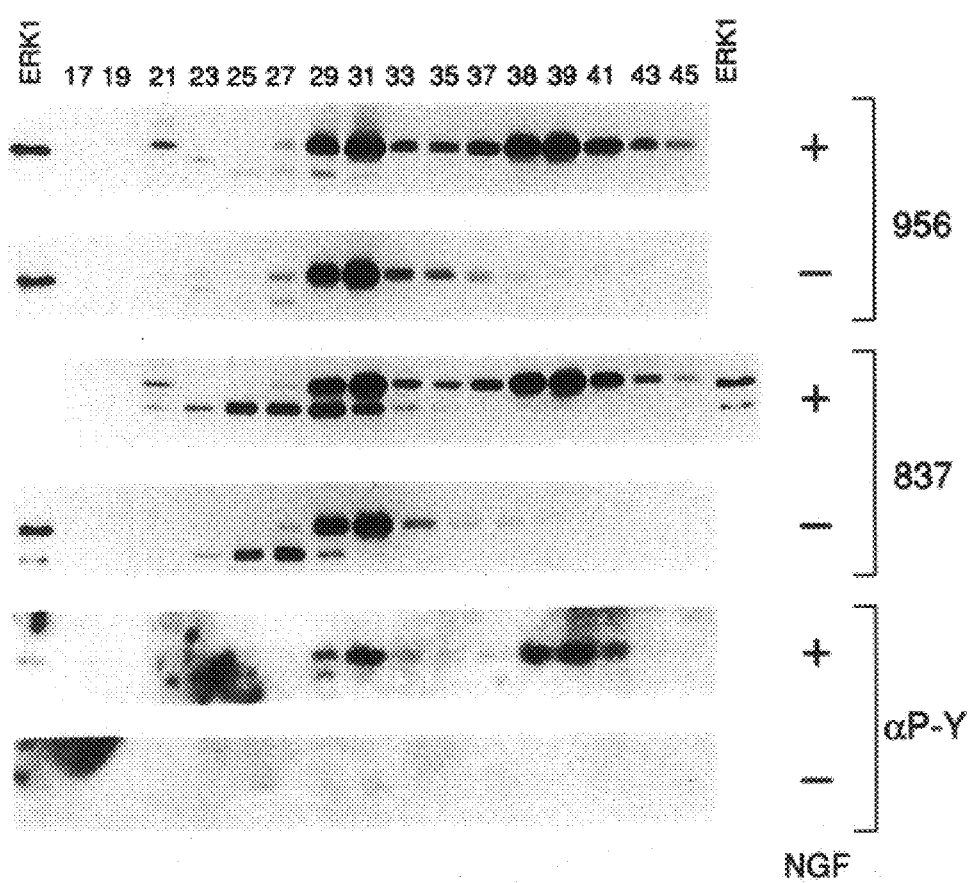

SEQUENCE LISTING

```
<160> NUMBER OF SEQ ID NOS: 21

<210> SEQ ID NO 1
<211> LENGTH: 1747
<212> TYPE: DNA
<213> ORGANISM: RAT
<220> FEATURE:
<221> NAME/KEY: CDS
<222> LOCATION: (1)...(1095)
<223> OTHER INFORMATION: ERK1 cDNA

<400> SEQUENCE: 1 agg gga act gct ggg gtc gtc ccg gtg gtc ccc ggg gag gtg gag gtg      48
Arg Gly Thr Ala Gly Val Val Pro Val Val Pro Gly Glu Val Glu Val
 1               5                  10                  15 gtg aag ggg cag cca ttc gac gtg ggc cca cgc tac acg cag ctg cag      96
Val Lys Gly Gln Pro Phe Asp Val Gly Pro Arg Tyr Thr Gln Leu Gln
             20                  25                  30 tac atc ggc gag ggc gcg tac ggc atg gtc agc tca gca tat gac cac     144
Tyr Ile Gly Glu Gly Ala Tyr Gly Met Val Ser Ser Ala Tyr Asp His
         35                  40                  45 gtg cgc aag acc aga gtg gct atc aag aag atc agc ccc ttc gag cat     192
Val Arg Lys Thr Arg Val Ala Ile Lys Lys Ile Ser Pro Phe Glu His
     50                  55                  60 caa acc tac tgt cag cgc acg ctg aga gaa atc cag atc ttg ctc gga     240
Gln Thr Tyr Cys Gln Arg Thr Leu Arg Glu Ile Gln Ile Leu Leu Gly
 65                  70                  75                  80 ttc cgc cat gag aat gtc ata ggc atc cga gac atc ctc aga gca ccc     288
Phe Arg His Glu Asn Val Ile Gly Ile Arg Asp Ile Leu Arg Ala Pro
                 85                  90                  95 acc ctg gaa gcc atg aga gat gtt tac att gtt cag gac ctc atg gag     336
Thr Leu Glu Ala Met Arg Asp Val Tyr Ile Val Gln Asp Leu Met Glu
            100                 105                 110 acg gac ctg tac aag ctg cta aag agc cag cag ctg agc aat gac cac     384
```

```
                                                    -continued

Thr Asp Leu Tyr Lys Leu Leu Lys Ser Gln Gln Leu Ser Asn Asp His
    115                 120                 125 atc tgc tac ttc ctc tac cag atc ctc cgg ggc ctc aag tac ata cac         432
Ile Cys Tyr Phe Leu Tyr Gln Ile Leu Arg Gly Leu Lys Tyr Ile His
    130                 135                 140 tcg gcc aat gtg ctg cac cgg gac ctg aag ccc tcc aat ctg ctt atc         480
Ser Ala Asn Val Leu His Arg Asp Leu Lys Pro Ser Asn Leu Leu Ile
145                 150                 155                 160 aac acc acc tgc gac ctt aag atc tgt gat ttt ggc ctt gcc cgg att         528
Asn Thr Thr Cys Asp Leu Lys Ile Cys Asp Phe Gly Leu Ala Arg Ile
                165                 170                 175 gct gac cct gag cac gac cac act ggc ttt ctg acc gag tat gtg gcc         576
Ala Asp Pro Glu His Asp His Thr Gly Phe Leu Thr Glu Tyr Val Ala
            180                 185                 190 aca cgc tgg tac cga gcc cca gag atc atg ctt aac tcc aag ggc tac         624
Thr Arg Trp Tyr Arg Ala Pro Glu Ile Met Leu Asn Ser Lys Gly Tyr
        195                 200                 205 acc aaa tcc att gac atc tgg tct gtg ggc tgc att ctg gct gag atg         672
Thr Lys Ser Ile Asp Ile Trp Ser Val Gly Cys Ile Leu Ala Glu Met
    210                 215                 220 ctc tcc aac cgg cct atc ttc ccc ggc aag cac tac ctg gac cag ctc         720
Leu Ser Asn Arg Pro Ile Phe Pro Gly Lys His Tyr Leu Asp Gln Leu
225                 230                 235                 240 aac cac att cta ggt ata ctg ggt tcc cca tcc caa gag gac cta aat         768
Asn His Ile Leu Gly Ile Leu Gly Ser Pro Ser Gln Glu Asp Leu Asn
                245                 250                 255 tgt atc att aac atg aag gcc cga aac tac cta cag tct ctg ccc tct         816
Cys Ile Ile Asn Met Lys Ala Arg Asn Tyr Leu Gln Ser Leu Pro Ser
            260                 265                 270 aaa acc aag gtg gct tgg gcc aag ctt ttt ccc aaa tct gac tcc aaa         864
Lys Thr Lys Val Ala Trp Ala Lys Leu Phe Pro Lys Ser Asp Ser Lys
        275                 280                 285 gct ctt gac ctg ctg gac cgg atg tta acc ttt aac cca aac aag cgc         912
Ala Leu Asp Leu Leu Asp Arg Met Leu Thr Phe Asn Pro Asn Lys Arg
    290                 295                 300 atc aca gta gag gaa gca ctg gct cac cct tac ctg gaa cag tac tat         960
Ile Thr Val Glu Glu Ala Leu Ala His Pro Tyr Leu Glu Gln Tyr Tyr
305                 310                 315                 320 gat ccg aca gat gaa cca gtg gct gag gag cca ttc acc ttt gac atg        1008
Asp Pro Thr Asp Glu Pro Val Ala Glu Glu Pro Phe Thr Phe Asp Met
                325                 330                 335 gag ctg gat gat ctc ccc aag gag cgg ctg aag gag ctg atc ttc caa        1056
Glu Leu Asp Asp Leu Pro Lys Glu Arg Leu Lys Glu Leu Ile Phe Gln
            340                 345                 350 gag aca gcc cgc ttc cag cca ggg gca cca gag gcc ccc taacaagaac         1105
Glu Thr Ala Arg Phe Gln Pro Gly Ala Pro Glu Ala Pro
        355                 360                 365 agacacccct gtccttttgg acctggtctg ctctacctgc tccttctctg cagattgtta     1165
gaaaatgaac tttgctcaac ccggacccecg gcagcccagg ctggaccaag ggtgggcctg     1225
gcacccctct cactgtgctg gggtctcctc gttcaagagg cttctcccac tccagtcccc     1285
tgccccatct cccccttgacc tgagtgatga ggtggtccca gagctgatct ctgctgctgt     1345
gtctttatct atccctgcta gccccagctc tggtagacgg ttctggaatg gaagggctat     1405
gaccgcccta ggacctgtgc tacagagggg tggagggcac tgagtaggct aagctctgcc     1465
ctactcatcc tgttggaacc ccacccccatt ttccctgaca gaacattcct aaatctcaag     1525
ggctagtttc cctgaggagc cagcctaggc ctaaccctct ccctctcaag ctgccacatg     1585
```

```
taacgccctt gctgcttctg tgtgtgggtg attggatgtg gaggcgggc ccgtggagag      1645 cccgtgcccc tccccacctc cctgtgcctg tatctaatat ataaatatag agatgtgtat      1705
atggaaaaaa aaaaaaaaaa aaaaaaaaaa aaaaaaaaaa aa                        1747
```

<210> SEQ ID NO 2
<211> LENGTH: 365
<212> TYPE: PRT
<213> ORGANISM: RAT
<220> FEATURE:
<223> OTHER INFORMATION: ERK1

<400> SEQUENCE: 2

```
Arg Gly Thr Ala Gly Val Val Pro Val Pro Gly Glu Val Glu Val
 1               5                  10                  15

Val Lys Gly Gln Pro Phe Asp Val Gly Pro Arg Tyr Thr Gln Leu Gln
             20                  25                  30

Tyr Ile Gly Glu Gly Ala Tyr Gly Met Val Ser Ser Ala Tyr Asp His
         35                  40                  45

Val Arg Lys Thr Arg Val Ala Ile Lys Lys Ile Ser Pro Phe Glu His
     50                  55                  60

Gln Thr Tyr Cys Gln Arg Thr Leu Arg Glu Ile Gln Ile Leu Leu Gly
 65                  70                  75                  80

Phe Arg His Glu Asn Val Ile Gly Ile Arg Asp Ile Leu Arg Ala Pro
                 85                  90                  95

Thr Leu Glu Ala Met Arg Asp Val Tyr Ile Val Gln Asp Leu Met Glu
            100                 105                 110

Thr Asp Leu Tyr Lys Leu Leu Lys Ser Gln Gln Leu Ser Asn Asp His
        115                 120                 125

Ile Cys Tyr Phe Leu Tyr Gln Ile Leu Arg Gly Leu Lys Tyr Ile His
    130                 135                 140

Ser Ala Asn Val Leu His Arg Asp Leu Lys Pro Ser Asn Leu Leu Ile
145                 150                 155                 160

Asn Thr Thr Cys Asp Leu Lys Ile Cys Asp Phe Gly Leu Ala Arg Ile
                165                 170                 175

Ala Asp Pro Glu His Asp His Thr Gly Phe Leu Thr Glu Tyr Val Ala
            180                 185                 190

Thr Arg Trp Tyr Arg Ala Pro Glu Ile Met Leu Asn Ser Lys Gly Tyr
        195                 200                 205

Thr Lys Ser Ile Asp Ile Trp Ser Val Gly Cys Ile Leu Ala Glu Met
    210                 215                 220

Leu Ser Asn Arg Pro Ile Phe Pro Gly Lys His Tyr Leu Asp Gln Leu
225                 230                 235                 240

Asn His Ile Leu Gly Ile Leu Gly Ser Pro Ser Gln Glu Asp Leu Asn
                245                 250                 255

Cys Ile Ile Asn Met Lys Ala Arg Asn Tyr Leu Gln Ser Leu Pro Ser
            260                 265                 270

Lys Thr Lys Val Ala Trp Ala Lys Leu Phe Pro Lys Ser Asp Ser Lys
        275                 280                 285

Ala Leu Asp Leu Leu Asp Arg Met Leu Thr Phe Asn Pro Asn Lys Arg
    290                 295                 300

Ile Thr Val Glu Glu Ala Leu Ala His Pro Tyr Leu Glu Gln Tyr Tyr
305                 310                 315                 320

Asp Pro Thr Asp Glu Pro Val Ala Glu Glu Pro Phe Thr Phe Asp Met
                325                 330                 335
```

```
Glu Leu Asp Asp Leu Pro Lys Glu Arg Leu Lys Glu Leu Ile Phe Gln
            340                 345                 350

Glu Thr Ala Arg Phe Gln Pro Gly Ala Pro Glu Ala Pro
            355                 360                 365

<210> SEQ ID NO 3
<211> LENGTH: 1467
<212> TYPE: DNA
<213> ORGANISM: RAT
<220> FEATURE:
<221> NAME/KEY: CDS
<222> LOCATION: (1)...(1245)
<223> OTHER INFORMATION: ERK2 cDNA

<400> SEQUENCE: 3 ccg tgg ttc tac cgg cgg tta gtt ctc tct tct gtg ttg tcc tcc ctc       48
Pro Trp Phe Tyr Arg Arg Leu Val Leu Ser Ser Val Leu Ser Ser Leu
 1               5                  10                  15 ctc gtt ccc gat cgc cgc cag ccg gct aca cgg gcg gcg gcg cgg ttc       96
Leu Val Pro Asp Arg Arg Gln Pro Ala Thr Arg Ala Ala Ala Arg Phe
                20                  25                  30 ctg tgg gaa gcg cag cac aag tcg agc ggt aac gcg aag cgt cga gcc      144
Leu Trp Glu Ala Gln His Lys Ser Ser Gly Asn Ala Lys Arg Arg Ala
        35                  40                  45 caa cgc ggc gga ggc tgt gca gcc aac atg gcg gcg gcg gcg gcg gcg      192
Gln Arg Gly Gly Gly Cys Ala Ala Asn Met Ala Ala Ala Ala Ala Ala
    50                  55                  60 ggc ccg gag atg gtc cgc ggg cag gtg ttc gac gtg ggg ccg cgc tac      240
Gly Pro Glu Met Val Arg Gly Gln Val Phe Asp Val Gly Pro Arg Tyr
65                  70                  75                  80 act aat ctc tcg tac atc gga gaa ggc gcc tac ggc atg gtt tgt tct      288
Thr Asn Leu Ser Tyr Ile Gly Glu Gly Ala Tyr Gly Met Val Cys Ser
                85                  90                  95 gct tat gat aat ctc aac aaa gtt cga gtt gct atc aag aaa atc agt      336
Ala Tyr Asp Asn Leu Asn Lys Val Arg Val Ala Ile Lys Lys Ile Ser
            100                 105                 110 cct ttt gag cac cag acc tac tgt cag aga acc ctg aga gag ata aaa      384
Pro Phe Glu His Gln Thr Tyr Cys Gln Arg Thr Leu Arg Glu Ile Lys
        115                 120                 125 atc cta ctg cgc ttc aga cat gag aac atc atc ggc atc aat gac atc      432
Ile Leu Leu Arg Phe Arg His Glu Asn Ile Ile Gly Ile Asn Asp Ile
    130                 135                 140 atc cgg gca cca acc att gag cag atg aaa gat gta tat ata gta cag      480
Ile Arg Ala Pro Thr Ile Glu Gln Met Lys Asp Val Tyr Ile Val Gln
145                 150                 155                 160 gac ctc atg gag aca gat ctt tac aag ctc ttg aag aca cag cac ctc      528
Asp Leu Met Glu Thr Asp Leu Tyr Lys Leu Leu Lys Thr Gln His Leu
                165                 170                 175 agc aat gat cat atc tgc tat ttt ctt tat cag atc ctg aga gga tta      576
Ser Asn Asp His Ile Cys Tyr Phe Leu Tyr Gln Ile Leu Arg Gly Leu
            180                 185                 190 aag tat ata cat tca gct aat gtt ctg cac cgt gac ctc aag cct tcc      624
Lys Tyr Ile His Ser Ala Asn Val Leu His Arg Asp Leu Lys Pro Ser
        195                 200                 205 aac ctc ctg ctg aac acc act tgt gat ctc aag atc tgt gac ttt ggc      672
Asn Leu Leu Leu Asn Thr Thr Cys Asp Leu Lys Ile Cys Asp Phe Gly
    210                 215                 220 ctt gcc cgt gtt gca gat cca gac cat gat cat aca ggg ttc ttg aca      720
Leu Ala Arg Val Ala Asp Pro Asp His Asp His Thr Gly Phe Leu Thr
225                 230                 235                 240 gag tat gta gcc acg cgt tgg tac aga gct cca gaa att atg ttg aat      768
```

```
Glu Tyr Val Ala Thr Arg Trp Tyr Arg Ala Pro Glu Ile Met Leu Asn
                245                 250                 255 tcc aag ggt tat acc aag tcc att gat att tgg tct gtg ggc tgc atc      816
Ser Lys Gly Tyr Thr Lys Ser Ile Asp Ile Trp Ser Val Gly Cys Ile
                260                 265                 270 ctg gca gag atg cta tcc aac agg cct atc ttc cca gga aag cat tac      864
Leu Ala Glu Met Leu Ser Asn Arg Pro Ile Phe Pro Gly Lys His Tyr
                275                 280                 285 ctt gac cag ctg aat cac atc ctg ggt att ctt gga tct cca tca cag      912
Leu Asp Gln Leu Asn His Ile Leu Gly Ile Leu Gly Ser Pro Ser Gln
            290                 295                 300 gaa gat ctg aat tgt ata ata aat tta aaa gct aga aac tat ttg ctt      960
Glu Asp Leu Asn Cys Ile Ile Asn Leu Lys Ala Arg Asn Tyr Leu Leu
305                 310                 315                 320 tct ctc ccg cac aaa aat aag gtg ccg tgg aac agg ttg ttc cca aac     1008
Ser Leu Pro His Lys Asn Lys Val Pro Trp Asn Arg Leu Phe Pro Asn
                325                 330                 335 gct gac tcc aaa gct ctg gat tta ctg gat aaa atg ttg aca ttt aac     1056
Ala Asp Ser Lys Ala Leu Asp Leu Leu Asp Lys Met Leu Thr Phe Asn
                340                 345                 350 cct cac aag agg att gaa gtt gaa cag gct ctg gcc cac ccg tac ctg     1104
Pro His Lys Arg Ile Glu Val Glu Gln Ala Leu Ala His Pro Tyr Leu
                355                 360                 365 gag cag tat tat gac cca agt gat gag ccc att gct gaa gca cca ttc     1152
Glu Gln Tyr Tyr Asp Pro Ser Asp Glu Pro Ile Ala Glu Ala Pro Phe
            370                 375                 380 aag ttt gac atg gag ctg gac gac tta cct aag gag aag ctc aaa gaa     1200
Lys Phe Asp Met Glu Leu Asp Asp Leu Pro Lys Glu Lys Leu Lys Glu
385                 390                 395                 400 ctc att ttt gaa gag act gct cga ttc cag cca gga tac aga tct         1245
Leu Ile Phe Glu Glu Thr Ala Arg Phe Gln Pro Gly Tyr Arg Ser
                405                 410                 415 taaattggtc aggacaaggg ctcagaggac tggacgcgtt cagatgtcgg tgtccccca    1305 gttcttgacc ctggtcctgt ctccagcccg tctcagctta cccactcttg actccttga   1365 gccgttccga ggggcagtct ggtcgtagtg gcttttatac tttcacggaa ttcttcagtc  1425
cagagagttc tcctgcacca ggccctgcac agttgcactc ag                     1467
```

<210> SEQ ID NO 4
<211> LENGTH: 415
<212> TYPE: PRT
<213> ORGANISM: RAT
<220> FEATURE:
<223> OTHER INFORMATION: ERK2

<400> SEQUENCE: 4

```
Pro Trp Phe Tyr Arg Arg Leu Val Leu Ser Ser Val Leu Ser Ser Leu
 1               5                  10                  15

Leu Val Pro Asp Arg Arg Gln Pro Ala Thr Arg Ala Ala Ala Arg Phe
                20                  25                  30

Leu Trp Glu Ala Gln His Lys Ser Ser Gly Asn Ala Lys Arg Arg Ala
            35                  40                  45

Gln Arg Gly Gly Gly Cys Ala Ala Asn Met Ala Ala Ala Ala Ala Ala
        50                  55                  60

Gly Pro Glu Met Val Arg Gly Gln Val Phe Asp Val Gly Pro Arg Tyr
65                  70                  75                  80

Thr Asn Leu Ser Tyr Ile Gly Glu Gly Ala Tyr Gly Met Val Cys Ser
                85                  90                  95
```

Ala Tyr Asp Asn Leu Asn Lys Val Arg Val Ala Ile Lys Lys Ile Ser
                100                 105                 110

Pro Phe Glu His Gln Thr Tyr Cys Gln Arg Thr Leu Arg Glu Ile Lys
            115                 120                 125

Ile Leu Leu Arg Phe Arg His Glu Asn Ile Ile Gly Ile Asn Asp Ile
        130                 135                 140

Ile Arg Ala Pro Thr Ile Glu Gln Met Lys Asp Val Tyr Ile Val Gln
145                 150                 155                 160

Asp Leu Met Glu Thr Asp Leu Tyr Lys Leu Leu Lys Thr Gln His Leu
                165                 170                 175

Ser Asn Asp His Ile Cys Tyr Phe Leu Tyr Gln Ile Leu Arg Gly Leu
            180                 185                 190

Lys Tyr Ile His Ser Ala Asn Val Leu His Arg Asp Leu Lys Pro Ser
        195                 200                 205

Asn Leu Leu Leu Asn Thr Thr Cys Asp Leu Lys Ile Cys Asp Phe Gly
210                 215                 220

Leu Ala Arg Val Ala Asp Pro Asp His Asp His Thr Gly Phe Leu Thr
225                 230                 235                 240

Glu Tyr Val Ala Thr Arg Trp Tyr Arg Ala Pro Glu Ile Met Leu Asn
                245                 250                 255

Ser Lys Gly Tyr Thr Lys Ser Ile Asp Ile Trp Ser Val Gly Cys Ile
            260                 265                 270

Leu Ala Glu Met Leu Ser Asn Arg Pro Ile Phe Pro Gly Lys His Tyr
        275                 280                 285

Leu Asp Gln Leu Asn His Ile Leu Gly Ile Leu Gly Ser Pro Ser Gln
290                 295                 300

Glu Asp Leu Asn Cys Ile Ile Asn Leu Lys Ala Arg Asn Tyr Leu Leu
305                 310                 315                 320

Ser Leu Pro His Lys Asn Lys Val Pro Trp Asn Arg Leu Phe Pro Asn
                325                 330                 335

Ala Asp Ser Lys Ala Leu Asp Leu Leu Asp Lys Met Leu Thr Phe Asn
            340                 345                 350

Pro His Lys Arg Ile Glu Val Glu Gln Ala Leu Ala His Pro Tyr Leu
        355                 360                 365

Glu Gln Tyr Tyr Asp Pro Ser Asp Glu Pro Ile Ala Glu Ala Pro Phe
370                 375                 380

Lys Phe Asp Met Glu Leu Asp Asp Leu Pro Lys Glu Lys Leu Lys Glu
385                 390                 395                 400

Leu Ile Phe Glu Glu Thr Ala Arg Phe Gln Pro Gly Tyr Arg Ser
                405                 410                 415

<210> SEQ ID NO 5
<211> LENGTH: 3671
<212> TYPE: DNA
<213> ORGANISM: RAT
<220> FEATURE:
<221> NAME/KEY: CDS
<222> LOCATION: (303)...(2018)
<223> OTHER INFORMATION: ERK3 cDNA

<400> SEQUENCE: 5
agacctgccg ggcgcatatt tattcacagt tttgtcccat gttaagtcgg ttagcatagt      60
gaatctgagt gcatagtatg tcatttcatt ccgttgagtt tctcgagtgt tttctttaaa     120
tgtctgcaga gtcgctaccc ttccttgaag tatgaagcac tgcaatcttc ttaattctca     180
gtatgaagag agatttttga gctttaagtc tgaggggaac tcagcaggcc tggttggcgt     240

-continued

```
ctgcaatgaa catcaagaaa gcatcgtgct gtgggaatgt gatcgttttt ctcccttttt      300
```

| | | | | | | | | | | | | | | | | |
|---|---|---|---|---|---|---|---|---|---|---|---|---|---|---|---|---|
| ga gag | atc | ttt | cct | ttt | gat | gcg | agt | ttt | ctt | cct | tgt | tta | cac | aag | | 347 |
| Glu | Ile | Phe | Pro | Phe | Asp | Ala | Ser | Phe | Leu | Pro | Cys | Leu | His | Lys | | |
| 1 | | | 5 | | | | | 10 | | | | | 15 | | | |

| ttc | aac | aat | ttg | aaa | gga | aaa | ggc | aat | tgt | aag | ggt | ttt | aaa | atg | gca | 395 |
|---|---|---|---|---|---|---|---|---|---|---|---|---|---|---|---|---|
| Phe | Asn | Asn | Leu | Lys | Gly | Lys | Gly | Asn | Cys | Lys | Gly | Phe | Lys | Met | Ala | |
| | | | 20 | | | | | 25 | | | | | 30 | | | |

| gag | aaa | ttt | gaa | agt | ctc | atg | aac | att | cat | ggc | ttt | gat | ctg | ggt | tcc | 443 |
|---|---|---|---|---|---|---|---|---|---|---|---|---|---|---|---|---|
| Glu | Lys | Phe | Glu | Ser | Leu | Met | Asn | Ile | His | Gly | Phe | Asp | Leu | Gly | Ser | |
| | | 35 | | | | | 40 | | | | | 45 | | | | |

| agg | tac | atg | gac | tta | aaa | cca | ttg | ggc | tgt | gga | ggc | aat | ggc | ttg | gtt | 491 |
|---|---|---|---|---|---|---|---|---|---|---|---|---|---|---|---|---|
| Arg | Tyr | Met | Asp | Leu | Lys | Pro | Leu | Gly | Cys | Gly | Gly | Asn | Gly | Leu | Val | |
| | | 50 | | | | | 55 | | | | | 60 | | | | |

| ttt | tct | gct | gta | gac | aat | gac | tgt | gac | aaa | aga | gta | gcc | atc | aag | aaa | 539 |
|---|---|---|---|---|---|---|---|---|---|---|---|---|---|---|---|---|
| Phe | Ser | Ala | Val | Asp | Asn | Asp | Cys | Asp | Lys | Arg | Val | Ala | Ile | Lys | Lys | |
| 65 | | | | | 70 | | | | | 75 | | | | | | |

| att | gtc | ctc | acc | gat | ccc | cag | agt | gtc | aaa | cat | gcc | ctc | cgt | gaa | atc | 587 |
|---|---|---|---|---|---|---|---|---|---|---|---|---|---|---|---|---|
| Ile | Val | Leu | Thr | Asp | Pro | Gln | Ser | Val | Lys | His | Ala | Leu | Arg | Glu | Ile | |
| 80 | | | | | 85 | | | | | 90 | | | | | 95 | |

| aaa | att | att | aga | aga | ctt | gac | cac | gat | aac | att | gtg | aaa | gtg | ttt | gaa | 635 |
|---|---|---|---|---|---|---|---|---|---|---|---|---|---|---|---|---|
| Lys | Ile | Ile | Arg | Arg | Leu | Asp | His | Asp | Asn | Ile | Val | Lys | Val | Phe | Glu | |
| | | | 100 | | | | | 105 | | | | | 110 | | | |

| att | ctt | ggt | ccc | agt | gga | agc | cag | ctg | aca | gac | gat | gtg | ggc | tct | cta | 683 |
|---|---|---|---|---|---|---|---|---|---|---|---|---|---|---|---|---|
| Ile | Leu | Gly | Pro | Ser | Gly | Ser | Gln | Leu | Thr | Asp | Asp | Val | Gly | Ser | Leu | |
| | | | 115 | | | | | 120 | | | | | 125 | | | |

| aca | gag | ctg | aat | agc | gtc | tac | att | gtt | cag | gag | tac | atg | gag | aca | gac | 731 |
|---|---|---|---|---|---|---|---|---|---|---|---|---|---|---|---|---|
| Thr | Glu | Leu | Asn | Ser | Val | Tyr | Ile | Val | Gln | Glu | Tyr | Met | Glu | Thr | Asp | |
| | | | 130 | | | | | 135 | | | | | 140 | | | |

| ttg | gcg | aac | gtg | ctg | gag | cag | ggc | cct | tta | ctg | gag | gag | cat | gcc | agg | 779 |
|---|---|---|---|---|---|---|---|---|---|---|---|---|---|---|---|---|
| Leu | Ala | Asn | Val | Leu | Glu | Gln | Gly | Pro | Leu | Leu | Glu | Glu | His | Ala | Arg | |
| | 145 | | | | | 150 | | | | | 155 | | | | | |

| ctc | ttc | atg | tac | cag | ctg | ctg | cgt | ggg | ctc | aag | tac | atc | cac | tct | gca | 827 |
|---|---|---|---|---|---|---|---|---|---|---|---|---|---|---|---|---|
| Leu | Phe | Met | Tyr | Gln | Leu | Leu | Arg | Gly | Leu | Lys | Tyr | Ile | His | Ser | Ala | |
| 160 | | | | | 165 | | | | | 170 | | | | | 175 | |

| aac | gtg | ctg | cac | agg | gat | ctg | aag | ccg | gcc | aac | ctt | ttc | att | aac | act | 875 |
|---|---|---|---|---|---|---|---|---|---|---|---|---|---|---|---|---|
| Asn | Val | Leu | His | Arg | Asp | Leu | Lys | Pro | Ala | Asn | Leu | Phe | Ile | Asn | Thr | |
| | | | 180 | | | | | 185 | | | | | 190 | | | |

| gaa | gac | ttg | gtg | ctg | aag | att | ggt | gac | ttt | ggc | ctg | gcc | cgg | atc | atg | 923 |
|---|---|---|---|---|---|---|---|---|---|---|---|---|---|---|---|---|
| Glu | Asp | Leu | Val | Leu | Lys | Ile | Gly | Asp | Phe | Gly | Leu | Ala | Arg | Ile | Met | |
| | | 195 | | | | | 200 | | | | | 205 | | | | |

| gat | cct | cat | tat | tcc | cat | aag | ggt | cat | ctt | tct | gaa | gga | ttg | gtt | acc | 971 |
|---|---|---|---|---|---|---|---|---|---|---|---|---|---|---|---|---|
| Asp | Pro | His | Tyr | Ser | His | Lys | Gly | His | Leu | Ser | Glu | Gly | Leu | Val | Thr | |
| | | 210 | | | | | 215 | | | | | 220 | | | | |

| aaa | tgg | tac | aga | tct | cca | cgg | ctt | tta | ctt | tct | cct | aat | aac | tat | act | 1019 |
|---|---|---|---|---|---|---|---|---|---|---|---|---|---|---|---|---|
| Lys | Trp | Tyr | Arg | Ser | Pro | Arg | Leu | Leu | Leu | Ser | Pro | Asn | Asn | Tyr | Thr | |
| 225 | | | | | 230 | | | | | 235 | | | | | | |

| aaa | gcg | att | gac | atg | tgg | gct | gca | ggc | tgc | atc | ttt | gct | gaa | atg | ctg | 1067 |
|---|---|---|---|---|---|---|---|---|---|---|---|---|---|---|---|---|
| Lys | Ala | Ile | Asp | Met | Trp | Ala | Ala | Gly | Cys | Ile | Phe | Ala | Glu | Met | Leu | |
| 240 | | | | | 245 | | | | | 250 | | | | | 255 | |

| act | ggt | aaa | acc | ctc | ttt | gca | ggt | gca | cat | gaa | ctt | gaa | cag | atg | cag | 1115 |
|---|---|---|---|---|---|---|---|---|---|---|---|---|---|---|---|---|
| Thr | Gly | Lys | Thr | Leu | Phe | Ala | Gly | Ala | His | Glu | Leu | Glu | Gln | Met | Gln | |
| | | | 260 | | | | | 265 | | | | | 270 | | | |

| ctg | atc | ttg | gag | tct | atc | cct | gtt | gtg | cac | gag | gaa | gat | cgg | cag | gag | 1163 |
|---|---|---|---|---|---|---|---|---|---|---|---|---|---|---|---|---|
| Leu | Ile | Leu | Glu | Ser | Ile | Pro | Val | Val | His | Glu | Glu | Asp | Arg | Gln | Glu | |
| | | | 275 | | | | | 280 | | | | | 285 | | | |

| ctt | ctc | agc | gtg | att | cca | gtt | tac | att | aga | aac | gac | atg | act | gag | cca | 1211 |
|---|---|---|---|---|---|---|---|---|---|---|---|---|---|---|---|---|
| Leu | Leu | Ser | Val | Ile | Pro | Val | Tyr | Ile | Arg | Asn | Asp | Met | Thr | Glu | Pro | |
| | | 290 | | | | | 295 | | | | | 300 | | | | |

```
cac aaa ccg ctg act cag ctg ctt ccg ggg att agt cgg gaa gca ctg      1259
His Lys Pro Leu Thr Gln Leu Leu Pro Gly Ile Ser Arg Glu Ala Leu
    305                 310                 315 gat ttc ctg gaa cag att ctg acg ttc agt ccc atg gac cgg ctg aca      1307
Asp Phe Leu Glu Gln Ile Leu Thr Phe Ser Pro Met Asp Arg Leu Thr
320                 325                 330                 335 gcc gag gaa gca ctt tcc cat cct tac atg agc atc tac tct ttg cca      1355
Ala Glu Glu Ala Leu Ser His Pro Tyr Met Ser Ile Tyr Ser Leu Pro
                340                 345                 350 acg gac gag cct att tcc agc cat cct ttc cac ata gaa gac gaa gtg      1403
Thr Asp Glu Pro Ile Ser Ser His Pro Phe His Ile Glu Asp Glu Val
            355                 360                 365 gac gac att ttg cta atg gat gaa aca cac agt cac att tat aac tgg      1451
Asp Asp Ile Leu Leu Met Asp Glu Thr His Ser His Ile Tyr Asn Trp
        370                 375                 380 gaa agg tac cac gat tgt cag ttc tcg gag cat gac tgg cct att cat      1499
Glu Arg Tyr His Asp Cys Gln Phe Ser Glu His Asp Trp Pro Ile His
    385                 390                 395 aac aac ttt gat atc gat gag gtt cag ctt gac ccg aga gct ctg tct      1547
Asn Asn Phe Asp Ile Asp Glu Val Gln Leu Asp Pro Arg Ala Leu Ser
400                 405                 410                 415 gat gtc acc gat gaa gaa gaa gtt caa gtt gat cct cga aag tac ttg      1595
Asp Val Thr Asp Glu Glu Glu Val Gln Val Asp Pro Arg Lys Tyr Leu
                420                 425                 430 gat gga gac cga gag aag tat ctg gag gat ccc gcc ttc gac acg agc      1643
Asp Gly Asp Arg Glu Lys Tyr Leu Glu Asp Pro Ala Phe Asp Thr Ser
            435                 440                 445 tac tct gct gag cct tgc tgg cag tac cca gat cac cac gag aac aag      1691
Tyr Ser Ala Glu Pro Cys Trp Gln Tyr Pro Asp His His Glu Asn Lys
        450                 455                 460 tac tgt gat ctg gag tgt agc cac acc tgt aac tac aaa aca agg tcg      1739
Tyr Cys Asp Leu Glu Cys Ser His Thr Cys Asn Tyr Lys Thr Arg Ser
    465                 470                 475 cca tca tac tta gat aac ctg gtg tgg agg gag agc gag gtt aac cat      1787
Pro Ser Tyr Leu Asp Asn Leu Val Trp Arg Glu Ser Glu Val Asn His
480                 485                 490                 495 tac tat gag ccg aag ctt att ata gat ctt tcg aac tgg aaa gag caa      1835
Tyr Tyr Glu Pro Lys Leu Ile Ile Asp Leu Ser Asn Trp Lys Glu Gln
                500                 505                 510 agt aag gac aaa tcg gac aag aga ggc aag tcc aag tgt gag agg aac      1883
Ser Lys Asp Lys Ser Asp Lys Arg Gly Lys Ser Lys Cys Glu Arg Asn
            515                 520                 525 ggg ttg gtg aag cgg aaa ttg cgg ttg agg aag cgt ccc agc agc tgg      1931
Gly Leu Val Lys Arg Lys Leu Arg Leu Arg Lys Arg Pro Ser Ser Trp
        530                 535                 540 ctg aga ggg aga ggg gcc aag gct ttg act ttg atg cct tca tcg cag      1979
Leu Arg Gly Arg Gly Ala Lys Ala Leu Thr Leu Met Pro Ser Ser Gln
    545                 550                 555 gca ccg ttc agc tca gtg ccc agc gtg agt ctg gtg acg tagttacaa        2028
Ala Pro Phe Ser Ser Val Pro Ser Val Ser Leu Val Thr
560                 565                 570 gttaaacgac ttgaatagct cagtgtccca gctagaaatg aaaagcctga tatccaagtc    2088
agtcagccga gaaaagcaag aaaagggaag ggctaacctg ggccagctgg gaggcttgta    2148
ccagccctcc tgggagaggg agtttgtgag tggcgggggg agtgcttcct tatcagtcag    2208
ttttgttgtg aggtcaggaa ggacgaacac gtggagaagg agaacactta caccagctat    2268
ttggacaagt ttttagcag gaaggaggat tctgaaatgc tagaaactga ggcagtggaa     2328
gaagggaagc gtggggagag aggccgygag gcaggggttc tgagcagcgg tggggagttt    2388
```

```
ctcctgagca ggcagctaga gtccataggc acgccgcagt tgcacagtgc aggggatcc      2448 ccactcaagt ccatccaggc cacgttaaca gcttcggcta tgaaatcttc ccctcaaatc     2508
gctcacaaga catacagcaa cattctgaaa catctgaact aaacactcag cagacacttc     2568
ttttgttctt catgaaatgt gttgtgtctt ttttatcact aatgttttaa gtcatttttt     2628
ttttacttga atcagaaggt gtcattaatt tgcaaggatt tttgttggtt gtcagtttgt     2688
aaaacacaaa gttttttcta catgtgagtt agttttcatt tgaagtggca tgtcgtttgc     2748
acacacacaa agaatagagc aaaacaatgc agtgcaggag gagacaagat gcgctaggat     2808
ggacagacat tctgacagag cagtgacctg cttagaggaa acaaaagctt gccttgaaac     2868
ttacacagtg agactgtaca taattgcatg aaaagatcta ttttttttcct gaaacatttt    2928 tcattcatta gtattttcaa gttttttcata gtgtacagat ttgttaagac acatgatagc    2988
agcagcaact gaaaacgaat gccgaatttg gtacacatgt gttatctacc tcaaggtaac     3048
aaaagtatgg gggcgaaagc taacgcaccc atagtcgtcc ggggcatatg cacttgtatc     3108
tagcgagcgt tgggggcagt aagcaatgag actcgtgggc catttatcaa tgtcctggtg     3168
ttcatcgttt acagtgaagt gttagataca tgacatctta tttattttag caaatcagta     3228
tattttctgt atttaattat aaaaggtaac ttagtttaag tttttatttgg aagtgcggtt    3288 gttgggtttt ggcactatgg tttgttgggt gccgagctga tctgagaagt cagcttgtcc     3348
cgaggctgtc catgtacgtt aagtaaagtg ctcactgtgt tataggaatc tgtattttgg    3408
gggtgcttga tctatccaca agaaaaaaaa ttaggaattt attataaaat gctgctagaa    3468
gtgttaatgg tgtttatttt ttaaaagctt gtaatgttag agttgtgtgc atggaagtga    3528
ttaaggtaca tcattattgt agtttgaaca ttgtacatga taagccttcc cccaccccg    3588 tttttactgt atgtttttat tgaatgatct attccccatc cctaggcaag catgaataaa    3648
attaggttaa atgtaaaaaa aaa                                             3671
```

<210> SEQ ID NO 6
<211> LENGTH: 572
<212> TYPE: PRT
<213> ORGANISM: RAT
<220> FEATURE:
<223> OTHER INFORMATION: ERK3

<400> SEQUENCE: 6

```
Glu Ile Phe Pro Phe Asp Ala Ser Phe Leu Pro Cys Leu His Lys Phe
 1               5                  10                  15

Asn Asn Leu Lys Gly Lys Gly Asn Cys Lys Gly Phe Lys Met Ala Glu
             20                  25                  30

Lys Phe Glu Ser Leu Met Asn Ile His Gly Phe Asp Leu Gly Ser Arg
         35                  40                  45

Tyr Met Asp Leu Lys Pro Leu Gly Cys Gly Gly Asn Gly Leu Val Phe
     50                  55                  60

Ser Ala Val Asp Asn Asp Cys Asp Lys Arg Val Ala Ile Lys Lys Ile
 65                  70                  75                  80

Val Leu Thr Asp Pro Gln Ser Val Lys His Ala Leu Arg Glu Ile Lys
                 85                  90                  95

Ile Ile Arg Arg Leu Asp His Asp Asn Ile Val Lys Val Phe Glu Ile
            100                 105                 110

Leu Gly Pro Ser Gly Ser Gln Leu Thr Asp Asp Val Gly Ser Leu Thr
        115                 120                 125
```

```
Glu Leu Asn Ser Val Tyr Ile Val Gln Glu Tyr Met Glu Thr Asp Leu
    130                 135                 140
Ala Asn Val Leu Glu Gln Gly Pro Leu Leu Glu His Ala Arg Leu
145                 150                 155                 160
Phe Met Tyr Gln Leu Leu Gly Gly Leu Lys Tyr Ile His Ser Ala Asn
                    165                 170                 175
Val Leu His Arg Asp Leu Lys Pro Ala Asn Leu Phe Ile Asn Thr Glu
                180                 185                 190
Asp Leu Val Leu Lys Ile Gly Asp Phe Gly Leu Ala Arg Ile Met Asp
            195                 200                 205
Pro His Tyr Ser His Lys Gly His Leu Ser Glu Gly Leu Val Thr Lys
        210                 215                 220
Trp Tyr Arg Ser Pro Arg Leu Leu Leu Ser Pro Asn Asn Tyr Thr Lys
225                 230                 235                 240
Ala Ile Asp Met Trp Ala Ala Gly Cys Ile Phe Ala Glu Met Leu Thr
                    245                 250                 255
Gly Lys Thr Leu Phe Ala Gly Ala His Glu Leu Glu Gln Met Gln Leu
                260                 265                 270
Ile Leu Glu Ser Ile Pro Val Val His Glu Glu Asp Arg Gln Glu Leu
            275                 280                 285
Leu Ser Val Ile Pro Val Tyr Ile Arg Asn Asp Met Thr Glu Pro His
        290                 295                 300
Lys Pro Leu Thr Gln Leu Leu Pro Gly Ile Ser Arg Glu Ala Leu Asp
305                 310                 315                 320
Phe Leu Glu Gln Ile Leu Thr Phe Ser Pro Met Asp Arg Leu Thr Ala
                    325                 330                 335
Glu Glu Ala Leu Ser His Pro Tyr Met Ser Ile Tyr Ser Leu Pro Thr
                340                 345                 350
Asp Glu Pro Ile Ser Ser His Pro Phe His Ile Glu Asp Glu Val Asp
            355                 360                 365
Asp Ile Leu Leu Met Asp Glu Thr His Ser His Ile Tyr Asn Trp Glu
        370                 375                 380
Arg Tyr His Asp Cys Gln Phe Ser Glu His Asp Trp Pro Ile His Asn
385                 390                 395                 400
Asn Phe Asp Ile Asp Glu Val Gln Leu Asp Pro Arg Ala Leu Ser Asp
                    405                 410                 415
Val Thr Asp Glu Glu Glu Val Gln Val Asp Pro Arg Lys Tyr Leu Asp
                420                 425                 430
Gly Asp Arg Glu Lys Tyr Leu Glu Asp Pro Ala Phe Asp Thr Ser Tyr
            435                 440                 445
Ser Ala Glu Pro Cys Trp Gln Tyr Pro Asp His His Glu Asn Lys Tyr
450                 455                 460
Cys Asp Leu Glu Cys Ser His Thr Cys Asn Tyr Lys Thr Arg Ser Pro
465                 470                 475                 480
Ser Tyr Leu Asp Asn Leu Val Trp Arg Glu Ser Glu Val Asn His Tyr
                    485                 490                 495
Tyr Glu Pro Lys Leu Ile Ile Asp Leu Ser Asn Trp Lys Glu Gln Ser
                500                 505                 510
Lys Asp Lys Ser Asp Lys Arg Gly Lys Ser Lys Cys Glu Arg Asn Gly
            515                 520                 525
Leu Val Lys Arg Lys Leu Arg Leu Arg Lys Pro Ser Ser Trp Leu
        530                 535                 540
Arg Gly Arg Gly Ala Lys Ala Leu Thr Leu Met Pro Ser Ser Gln Ala
```

```
                545                 550                 555                 560
            Pro Phe Ser Ser Val Pro Ser Val Ser Leu Val Thr
                                565                 570
```

<210> SEQ ID NO 7
<211> LENGTH: 6
<212> TYPE: PRT
<213> ORGANISM: RAT
<220> FEATURE:
<223> OTHER INFORMATION: Peptide

<400> SEQUENCE: 7

```
Gln Tyr Ile Gly Glu Gly
  1               5
```

<210> SEQ ID NO 8
<211> LENGTH: 28
<212> TYPE: DNA
<213> ORGANISM: RAT
<220> FEATURE:
<223> OTHER INFORMATION: Oligonucleotide
<221> NAME/KEY: modified_base
<222> LOCATION: 23
<223> OTHER INFORMATION: n=a, c, g or t

<400> SEQUENCE: 8
ttctagaatt ccartayath ggngargg                                      28

<210> SEQ ID NO 9
<211> LENGTH: 6
<212> TYPE: PRT
<213> ORGANISM: RAT
<220> FEATURE:
<223> OTHER INFORMATION: Peptide

<400> SEQUENCE: 9

```
Asp Leu Lys Pro Ser Asn
  1               5
```

<210> SEQ ID NO 10
<211> LENGTH: 31
<212> TYPE: DNA
<213> ORGANISM: RAT
<220> FEATURE:
<223> OTHER INFORMATION: Oligonucleotide
<221> NAME/KEY: modified_base
<222> LOCATION: 17
<223> OTHER INFORMATION: n=a, c, g, or t
<221> NAME/KEY: modified_base
<222> LOCATION: 20
<223> OTHER INFORMATION: n=a, c, g, or t
<221> NAME/KEY: modified_base
<222> LOCATION: 26
<223> OTHER INFORMATION: n=a, c, g, or t

<400> SEQUENCE: 10
ttctcgagtc gacrttngan ggyttnarrt c                                  31

<210> SEQ ID NO 11
<211> LENGTH: 4
<212> TYPE: PRT
<213> ORGANISM: RAT
<220> FEATURE:
<223> OTHER INFORMATION: Peptide

<400> SEQUENCE: 11

```
Gln Tyr Asp Leu
  1
```

<210> SEQ ID NO 12
<211> LENGTH: 6
<212> TYPE: PRT
<213> ORGANISM: RAT
<220> FEATURE:
<223> OTHER INFORMATION: Peptide

<400> SEQUENCE: 12

Gly Glu Gly Ala Tyr Gly
 1               5

<210> SEQ ID NO 13
<211> LENGTH: 7
<212> TYPE: PRT
<213> ORGANISM: YEAST
<220> FEATURE:
<223> OTHER INFORMATION: Peptide

<400> SEQUENCE: 13

Val Pro Ser Thr Ala Ile Arg
 1               5

<210> SEQ ID NO 14
<211> LENGTH: 6
<212> TYPE: PRT
<213> ORGANISM: RAT
<220> FEATURE:
<223> OTHER INFORMATION: Peptide

<400> SEQUENCE: 14

Asp Leu Lys Pro Ala Asn
 1               5

<210> SEQ ID NO 15
<211> LENGTH: 549
<212> TYPE: DNA
<213> ORGANISM: RAT
<220> FEATURE:
<221> NAME/KEY: CDS
<222> LOCATION: (1)...(549)
<223> OTHER INFORMATION: ERK1

<400> SEQUENCE: 15

```
gct ccg ggg ggc ggg ggc ggg gag ccc agg gga act gct ggg gtc gtc      48
Ala Pro Gly Gly Gly Gly Gly Glu Pro Arg Gly Thr Ala Gly Val Val
 1               5                  10                  15 ccg gtg gtc ccc ggg gag gtg gag gtg gtg aag ggg cag cca ttc gac      96
Pro Val Val Pro Gly Glu Val Glu Val Val Lys Gly Gln Pro Phe Asp
                 20                  25                  30 gtg ggc cca cgc tac acg cag ctg cag tac atc ggc gag ggc gcg tac     144
Val Gly Pro Arg Tyr Thr Gln Leu Gln Tyr Ile Gly Glu Gly Ala Tyr
             35                  40                  45 ggc atg gtc agc tca gca tat gac cac gtg cgc aag acc aga gtg gct     192
Gly Met Val Ser Ser Ala Tyr Asp His Val Arg Lys Thr Arg Val Ala
         50                  55                  60 atc aag aag atc agc ccc ttc gag cat caa acc tac tgt cag cgc acg     240
Ile Lys Lys Ile Ser Pro Phe Glu His Gln Thr Tyr Cys Gln Arg Thr
 65                  70                  75                  80 ctg aga gaa atc cag atc ttg ctc gga ttc cgc cat gag aat gtc ata     288
Leu Arg Glu Ile Gln Ile Leu Leu Gly Phe Arg His Glu Asn Val Ile
                 85                  90                  95 ggc atc cga gac atc ctc aga gca ccc acc ctg gaa gcc atg aga gat     336
Gly Ile Arg Asp Ile Leu Arg Ala Pro Thr Leu Glu Ala Met Arg Asp
                100                 105                 110
```

```
gtt tac att gtt cag gac ctc atg gag acg gac ctg tac aag ctg cta    384
Val Tyr Ile Val Gln Asp Leu Met Glu Thr Asp Leu Tyr Lys Leu Leu
        115                 120                 125 aag agc cag cag ctg agc aat gac cac atc tgc tac ttc ctc tac cag    432
Lys Ser Gln Gln Leu Ser Asn Asp His Ile Cys Tyr Phe Leu Tyr Gln
130                 135                 140 atc ctc cgg ggc ctc aag tac ata cac tcg gcc aat gtg ctg cac cgg    480
Ile Leu Arg Gly Leu Lys Tyr Ile His Ser Ala Asn Val Leu His Arg
145                 150                 155                 160 gac ctg aag ccc tcc aat ctg ctt atc aac acc acc tgc gac ctt aag    528
Asp Leu Lys Pro Ser Asn Leu Leu Ile Asn Thr Thr Cys Asp Leu Lys
                165                 170                 175 atc tgt gat ttt ggc ctt gcc                                        549
Ile Cys Asp Phe Gly Leu Ala
            180
```

<210> SEQ ID NO 16
<211> LENGTH: 183
<212> TYPE: PRT
<213> ORGANISM: RAT
<220> FEATURE:
<223> OTHER INFORMATION: ERK1

<400> SEQUENCE: 16

```
Ala Pro Gly Gly Gly Gly Glu Pro Arg Gly Thr Ala Gly Val Val
 1               5                  10                  15

Pro Val Pro Gly Glu Val Glu Val Val Lys Gly Gln Pro Phe Asp
                20                  25                  30

Val Gly Pro Arg Tyr Thr Gln Leu Gln Tyr Ile Gly Glu Gly Ala Tyr
            35                  40                  45

Gly Met Val Ser Ser Ala Tyr Asp His Val Arg Lys Thr Arg Val Ala
 50                  55                  60

Ile Lys Lys Ile Ser Pro Phe Glu His Gln Thr Tyr Cys Gln Arg Thr
 65                  70                  75                  80

Leu Arg Glu Ile Gln Ile Leu Leu Gly Phe Arg His Glu Asn Val Ile
                85                  90                  95

Gly Ile Arg Asp Ile Leu Arg Ala Pro Thr Leu Glu Ala Met Arg Asp
            100                 105                 110

Val Tyr Ile Val Gln Asp Leu Met Glu Thr Asp Leu Tyr Lys Leu Leu
        115                 120                 125

Lys Ser Gln Gln Leu Ser Asn Asp His Ile Cys Tyr Phe Leu Tyr Gln
130                 135                 140

Ile Leu Arg Gly Leu Lys Tyr Ile His Ser Ala Asn Val Leu His Arg
145                 150                 155                 160

Asp Leu Lys Pro Ser Asn Leu Leu Ile Asn Thr Thr Cys Asp Leu Lys
                165                 170                 175

Ile Cys Asp Phe Gly Leu Ala
            180
```

<210> SEQ ID NO 17
<211> LENGTH: 537
<212> TYPE: DNA
<213> ORGANISM: RAT
<220> FEATURE:
<221> NAME/KEY: CDS
<222> LOCATION: (1)...(504)
<223> OTHER INFORMATION: ERK1 psi

<400> SEQUENCE: 17

-continued

| | |
|---|---|
| gct ccg ggg gat ggg ggc ggg gag ccc agg gga act gct ggg gtc gtc<br>Ala Pro Gly Asp Gly Gly Gly Glu Pro Arg Gly Thr Ala Gly Val Val<br>1                 5                     10                  15 | 48 |
| ctg gtg gtc ccc cgg gag gtg gag ggg cag cca ttc gac gtg ggc cca<br>Leu Val Val Pro Arg Glu Val Glu Gly Gln Pro Phe Asp Val Gly Pro<br>                 20                     25                    30 | 96 |
| tgt tac aca cag ctg cag tac atc ggc gaa gat gcg gac atg gtc agc<br>Cys Tyr Thr Gln Leu Gln Tyr Ile Gly Glu Asp Ala Asp Met Val Ser<br>             35                    40                    45 | 144 |
| tca gct tat gac cac gtg cgc aag acc aga gtg gct atc aag aag att<br>Ser Ala Tyr Asp His Val Arg Lys Thr Arg Val Ala Ile Lys Lys Ile<br>50                           55                    60 | 192 |
| agc ccc ttc gag cat caa acc tac tgt cag ccc acg ttg aga gaa acc<br>Ser Pro Phe Glu His Gln Thr Tyr Cys Gln Pro Thr Leu Arg Glu Thr<br>65                           70                    75                  80 | 240 |
| cag ata ttg ctg cga ttc cgc cat gag aat gtc ata ggc atc cga gac<br>Gln Ile Leu Leu Arg Phe Arg His Glu Asn Val Ile Gly Ile Arg Asp<br>                        85                    90                    95 | 288 |
| atc ctc aga gca ccc acc ctg gaa gct atg aga gat gtt tac att gtt<br>Ile Leu Arg Ala Pro Thr Leu Glu Ala Met Arg Asp Val Tyr Ile Val<br>                 100                   105                  110 | 336 |
| cag gac ctc atg gat aca gac ctg tac aag ctg ctt aag agc caa cag<br>Gln Asp Leu Met Asp Thr Asp Leu Tyr Lys Leu Leu Lys Ser Gln Gln<br>                 115                   120                  125 | 384 |
| ctg agc aat gac cac atc tgc ttc ttc ctc tac cag atc ctc cgg ggc<br>Leu Ser Asn Asp His Ile Cys Phe Phe Leu Tyr Gln Ile Leu Arg Gly<br>130                          135                    140 | 432 |
| ctc aag tac ata cac tcg gcc aat gtg ctg cac cgg gac ctg aag ccc<br>Leu Lys Tyr Ile His Ser Ala Asn Val Leu His Arg Asp Leu Lys Pro<br>145                          150                    155                  160 | 480 |
| tcc aat ctg ctt atc aac acc acc tgagacctta agatctgtga ttttggcctg<br>Ser Asn Leu Leu Ile Asn Thr Thr<br>                        165 | 534 |
| gcc | 537 |

<210> SEQ ID NO 18
<211> LENGTH: 168
<212> TYPE: PRT
<213> ORGANISM: Artificial Sequence
<220> FEATURE:
<223> OTHER INFORMATION: ERK1 psi

<400> SEQUENCE: 18

Ala Pro Gly Asp Gly Gly Gly Glu Pro Arg Gly Thr Ala Gly Val Val
1               5                   10                  15

Leu Val Val Pro Arg Glu Val Glu Gly Gln Pro Phe Asp Val Gly Pro
            20                  25                  30

Cys Tyr Thr Gln Leu Gln Tyr Ile Gly Glu Asp Ala Asp Met Val Ser
        35                  40                  45

Ser Ala Tyr Asp His Val Arg Lys Thr Arg Val Ala Ile Lys Lys Ile
    50                  55                  60

Ser Pro Phe Glu His Gln Thr Tyr Cys Gln Pro Thr Leu Arg Glu Thr
65                  70                  75                  80

Gln Ile Leu Leu Arg Phe Arg His Glu Asn Val Ile Gly Ile Arg Asp
                85                  90                  95

Ile Leu Arg Ala Pro Thr Leu Glu Ala Met Arg Asp Val Tyr Ile Val
            100                 105                 110

Gln Asp Leu Met Asp Thr Asp Leu Tyr Lys Leu Leu Lys Ser Gln Gln
        115                 120                 125

-continued

```
Leu Ser Asn Asp His Ile Cys Phe Phe Leu Tyr Gln Ile Leu Arg Gly
        130                 135                 140

Leu Lys Tyr Ile His Ser Ala Asn Val Leu His Arg Asp Leu Lys Pro
145                 150                 155                 160

Ser Asn Leu Leu Ile Asn Thr Thr
                165

<210> SEQ ID NO 19
<211> LENGTH: 353
<212> TYPE: PRT
<213> ORGANISM: YEAST
<220> FEATURE:
<223> OTHER INFORMATION: FUS3

<400> SEQUENCE: 19

Met Pro Lys Arg Ile Val Tyr Asn Ile Ser Ser Asp Phe Gln Leu Lys
  1               5                  10                  15

Ser Leu Leu Gly Glu Gly Ala Tyr Gly Val Val Cys Ser Ala Thr His
            20                  25                  30

Lys Pro Thr Gly Glu Ile Val Ala Ile Lys Lys Ile Glu Pro Phe Asp
        35                  40                  45

Lys Pro Leu Phe Ala Leu Arg Thr Leu Arg Glu Ile Lys Ile Leu Lys
 50                  55                  60

His Phe His Glu Asn Ile Ile Thr Ile Phe Asn Ile Gln Arg Pro Asp
65                  70                  75                  80

Ser Phe Glu Asn Phe Asn Glu Val Tyr Ile Ile Gln Glu Leu Met
                85                  90                  95

Gln Thr Asp Leu His Arg Val Ile Ser Thr Gln Met Leu Ser Asp Asp
                100                 105                 110

His Ile Gln Tyr Phe Ile Tyr Gln Thr Leu Arg Ala Val Lys Tyr Val
            115                 120                 125

Leu His Gly Ser Asn Val Ile His Arg Asp Leu Lys Pro Ser Asn Leu
        130                 135                 140

Leu Ile Asn Ser Asn Cys Asp Leu Lys Val Cys Asp Phe Gly Leu Ala
145                 150                 155                 160

Arg Ile Asp Glu Ser Ala Ala Asp Asn Ser Glu Pro Thr Gly Gln Gln
                165                 170                 175

Ser Gly Met Thr Glu Tyr Val Ala Thr Arg Trp Tyr Arg Ala Pro Glu
            180                 185                 190

Val Met Leu Thr Ser Ala Lys Tyr Ser Arg Ala Met Asp Val Trp Ser
        195                 200                 205

Cys Gly Cys Ile Leu Ala Glu Leu Phe Leu Arg Arg Pro Ile Phe Pro
    210                 215                 220

Gly Arg Asp Tyr Arg His Gln Leu Leu Leu Ile Phe Gly Ile Ile Gly
225                 230                 235                 240

Thr Pro His Ser Asp Asn Asp Leu Arg Cys Ile Glu Ser Pro Arg Ala
                245                 250                 255

Arg Glu Tyr Ile Lys Ser Leu Pro Met Tyr Pro Ala Ala Pro Leu Glu
            260                 265                 270

Lys Met Phe Pro Arg Val Asn Pro Lys Gly Ile Asp Leu Leu Gln Arg
        275                 280                 285

Met Leu Val Phe Asp Pro Ala Lys Arg Ile Thr Ala Lys Glu Ala Leu
    290                 295                 300

Glu His Pro Tyr Leu Gln Thr Tyr His Asp Pro Asn Asp Glu Pro Glu
305                 310                 315                 320
```

Gly Glu Pro Ile Pro Pro Ser Phe Phe Glu Phe Asp His His Lys Glu
                325                 330                 335

Ala Leu Thr Thr Lys Asp Leu Lys Lys Leu Ile Trp Asn Glu Ile Phe
            340                 345                 350

Ser

<210> SEQ ID NO 20
<211> LENGTH: 368
<212> TYPE: PRT
<213> ORGANISM: YEAST
<220> FEATURE:
<223> OTHER INFORMATION: KSS1

<400> SEQUENCE: 20

Met Ala Arg Thr Ile Thr Phe Asp Ile Pro Ser Gln Tyr Lys Leu Val
1               5                   10                  15

Asp Leu Ile Gly Glu Gly Ala Tyr Gly Thr Val Cys Ser Ala Ile His
            20                  25                  30

Lys Pro Ser Gly Ile Lys Val Ala Ile Lys Lys Ile Gln Pro Phe Ser
        35                  40                  45

Lys Lys Leu Phe Val Thr Arg Thr Ile Arg Glu Ile Lys Leu Leu Arg
50                  55                  60

Tyr Phe His Glu His Glu Asn Ile Ile Ser Ile Leu Asp Lys Val Arg
65                  70                  75                  80

Pro Val Ser Ile Asp Lys Leu Asn Ala Val Tyr Leu Val Glu Glu Leu
                85                  90                  95

Met Glu Thr Asp Leu Gln Lys Val Ile Asn Asn Gln Asn Ser Gly Phe
            100                 105                 110

Ser Thr Leu Ser Asp Asp His Val Gln Tyr Phe Thr Tyr Gln Ile Leu
        115                 120                 125

Arg Ala Leu Lys Ser Ile His Ser Ala Gln Val Ile His Arg Asp Ile
130                 135                 140

Lys Pro Ser Asn Leu Leu Leu Asn Ser Asn Cys Asp Leu Lys Val Cys
145                 150                 155                 160

Asp Phe Gly Leu Ala Arg Cys Leu Ala Ser Ser Ser Asp Ser Arg Glu
                165                 170                 175

Thr Leu Val Gly Phe Met Thr Glu Tyr Val Ala Thr Arg Trp Tyr Arg
            180                 185                 190

Ala Pro Glu Ile Met Leu Thr Phe Gln Glu Tyr Thr Thr Ala Met Asp
        195                 200                 205

Ile Trp Ser Cys Gly Cys Ile Leu Ala Glu Met Val Ser Gly Lys Pro
210                 215                 220

Leu Phe Pro Gly Arg Asp Tyr His His Gln Leu Trp Leu Ile Leu Glu
225                 230                 235                 240

Val Leu Gly Thr Pro Ser Phe Glu Asp Phe Asn Gln Ile Lys Ser Lys
                245                 250                 255

Arg Ala Lys Glu Tyr Ile Ala Asn Leu Pro Met Arg Pro Pro Leu Pro
            260                 265                 270

Trp Glu Thr Val Trp Ser Lys Thr Asp Leu Asn Pro Asp Met Ile Asp
        275                 280                 285

Leu Leu Asp Lys Met Leu Gln Phe Asn Pro Asp Lys Arg Ile Ser Ala
290                 295                 300

Ala Glu Ala Leu Arg His Pro Tyr Leu Ala Met Tyr His Asp Pro Ser
305                 310                 315                 320

```
Asp Glu Pro Glu Tyr Pro Pro Leu Asn Leu Asp Asp Glu Phe Trp Lys
                325                 330                 335

Leu Asp Asn Lys Ile Met Arg Pro Glu Glu Glu Glu Val Pro Ile
                340                 345                 350

Glu Met Leu Lys Asp Met Leu Tyr Asp Glu Leu Met Lys Thr Met Glu
                355                 360                 365

<210> SEQ ID NO 21
<211> LENGTH: 297
<212> TYPE: PRT
<213> ORGANISM: Homo sapiens

<400> SEQUENCE: 21

Met Glu Asp Tyr Thr Lys Ile Glu Lys Ile Gly Glu Gly Thr Tyr Gly
  1               5                  10                  15

Val Val Tyr Lys Gly Arg His Lys Thr Thr Gly Gln Val Val Ala Met
                 20                  25                  30

Lys Lys Ile Arg Leu Glu Ser Glu Glu Glu Gly Val Pro Ser Thr Ala
             35                  40                  45

Ile Arg Glu Ile Ser Leu Leu Lys Glu Leu Arg His Pro Asn Ile Val
         50                  55                  60

Ser Leu Gln Asp Val Leu Met Gln Asp Ser Arg Leu Tyr Leu Ile Phe
 65                  70                  75                  80

Glu Phe Leu Ser Met Asp Leu Lys Lys Tyr Leu Asp Ser Ile Pro Pro
                 85                  90                  95

Gly Gln Tyr Met Asp Ser Ser Leu Val Lys Ser Tyr Leu Tyr Gln Ile
                100                 105                 110

Leu Gln Gly Ile Val Phe Cys Ile His Ser Arg Arg Val Leu His Arg
            115                 120                 125

Asp Leu Lys Gln Asn Leu Leu Ile Asp Asp Lys Gly Thr Ile Lys Leu
        130                 135                 140

Ala Asp Phe Gly Leu Ala Arg Ala Phe Gly Ile Pro Ile Arg Val Tyr
145                 150                 155                 160

Thr His Tyr Val Val Thr Leu Trp Tyr Arg Ser Pro Glu Val Leu Leu
                165                 170                 175

Gly Ser Ala Arg Tyr Ser Thr Pro Val Asp Ile Trp Ser Ile Gly Thr
            180                 185                 190

Ile Phe Ala Glu Leu Ala Thr Lys Lys Pro Leu Phe His Gly Asp Ser
        195                 200                 205

Glu Ile Asp Gln Leu Phe Arg Ile Phe Arg Ala Leu Gly Thr Pro Asn
    210                 215                 220

Asn Glu Val Trp Pro Glu Val Glu Ser Leu Gln Asp Tyr Lys Asn Thr
225                 230                 235                 240

Phe Pro Lys Trp Lys Pro Gly Ser Leu Ala Ser His Val Lys Asn Leu
                245                 250                 255

Asp Glu Asn Gly Leu Asp Leu Leu Ser Lys Met Leu Ile Tyr Asp Pro
            260                 265                 270

Ala Lys Arg Ile Ser Gly Lys Met Ala Leu Asn His Pro Tyr Phe Asn
        275                 280                 285

Asp Leu Asp Asn Gln Ile Lys Lys Met
    290                 295
```

ERK1 MAP2 PROTEIN KINASE

This is a file wrapper continuation of application U.S. Ser. No. 08/462,874, filed Jun. 5, 1995, now abandoned, which is a divisional of U.S. Ser. No. 08/178,488, filed Jan. 7, 1994, now abandoned, which is a continuation of U.S. Ser. No. 07/701,544, filed May 16, 1991, now abandoned, which is a continuation-in-part of U.S. Ser. No. 07/532,004, filed Jun. 1, 1990, now abandoned, each of which is incorporated by reference herein in its entirety.

Pursuant to the provisions of 35 U.S.C. §202(c), it is hereby acknowledged that the Government has certain rights in this invention, which was made in part with fund; from the National Institutes of Health.

1. INTRODUCTION

The present invention relates to a newly identified family of MAP2 protein kinases. It is based, in part, on the cloning and characterization of three MAP2 protein kinases, designated ERK1, ERK2, and ERK3, which are expressed in the central nervous system and elsewhere. The present invention provides for recombinant MAP2 kinase nucleic acids and proteins, cell lines and microorganisms comprising recombinant MAP2 kinase molecules, and bioassay methods for detecting the presence of biologically active compounds which utilize recombinant MAP2 kinase molecules.

2. BACKGROUND OF THE INVENTION

2.1. Protein Kinase Cascades and the Regulation of Cell Function

A cascade of phosphorylation reactions, initiated by a receptor tyrosine kinase, has been proposed as a potential transducing mechanism for growth factor receptors, including the insulin receptor (Cobb and Rosen, 1984, Biochim. Biophys. Acta. 738:1–8; Denton et al., 1984, Biochem. Soc. Trans. 12:768–771). In his review of the role of protein phosphorylation in the normal control of enzyme activity, Cohen (1985, Eur. J. Biochem. 151:439–448) states that amplification and diversity in hormone action are achieved by two principal mechanisms, the reversible phosphorylation of proteins and the formation of "second messengers"; many key regulatory proteins are interconverted between phosphorylated and unphosphorylated forms by cellular protein kinases and certain protein phosphatases.

Some hormones appear to transmit their information to the cell interior by activating transmembrane signalling systems that control production of a relatively small number of chemical mediators, the "second messengers." These second messengers, in turn, are found to regulate protein kinase and phosphatase activities, thereby altering the phosphorylation states of many intracellular proteins, and consequently controlling the activity of enzymes which are regulated by their degree of phosphorylation (see FIG. 1). The receptors for other hormones are themselves protein kinases or interact directly with protein kinases to initiate protein kinase signalling cascades. These series of events are believed to explain the diversity associated with the actions of various hormones (Cohen, 1985, Eur. J. Biochem. 151:439–448; Edelman et al., 1987, Ann. Rev. Biochem. 56:567–613).

Insulin, like most cellular regulators, exerts its effects on many cellular processes through alterations in the phosphorylation state of serine and threonine residues within regulated proteins. Insulin exerts these effects via its receptor, which has intrinsic tyrosine-specific protein kinase activity (Rosen et al., 1983, Proc. Natl. Acad. Sci. U.S.A. 80:3237–3240; Ebina et al., 1985, Cell 40:747–758). Of note, the proteins encoded by several oncogenes are also protein-tyrosine kinases. For example, $P68^{gag-ros}$, a transmembrane transforming protein, bears many similarities to the insulin receptor, sharing 50% amino acid identity (for discussion, see Boulton et al., 1990, J. Biol. Chem. 265:2713–2719).

Nerve growth factor (NGF), a neurotrophic agent necessary for the development and function of certain central and peripheral nervous system neurons, is also believed to influence cellular functions, at least in part, by altering phosphorylation of intracellular proteins. It has been observed that NGF promotes changes in the phosphorylation of certain cellular proteins (discussed in Volonte et al., 1989, J. Cell. Biol. 109:2395–2403; Aletta et al., 1988, J. Cell. Biol. 106:1573–1581; Halegoua and Patrick, 1980, Cell 22:571–581; Hama et al., 1986, Proc. Natl. Acad. Sci. U.S.A. 83:2353–2357; Romano et al., 1987, J. Neurosci, 7:1294–1299). Furthermore, NGF appears to regulate several different protein kinase activities (Blenis and Erikson, 1986, EMBO J. 5:3441–3447; Cremins et al., 1986, J. Cell Biol. 103:887–893; Landreth and Rieser, 1985, J. Cell. Biol. 100:677–683; Levi et al, 1988, Mol. Neurobiol. 2:201–226; Mutoh et al., 1988, J. Biol. Chem. 263:15853–15856; Rowland et al., 1987, J. Biol. Chem. 262:7504–7513). Mutoh et al. (1988, J. Biol. Chem. 263:15853–15856) reports that NGF appears to increase the activities of kinases capable of phosphorylating ribosomal protein S6 (S6 kinases) in the PC12 rat pheochromocytoma cell line, a model system regularly used to study NGF function. Volonte et al. (1989, J. Cell. Biol. 109:2395–2403) states that the differential inhibition of the NGF response by purine analogues in PC12 cells appeared to correlate with the inhibition of PKN, an NGF-regulated serine protein kinase. Additionally, activators of the cyclic AMP dependent protein kinase (PKA) and protein kinase C (PKC) have been reported to mimic some but not all of the cellular responses to NGF (Levi et al., 1988, Mol. Neurobiol. 2:201–226). Miyasaka et al. (1990, J. Biol. Chem. 265:4730–4735) reports that NGF stimulates a protein kinase in PC12 cells that phosphorylates microtubule-associated protein-2. Interestingly, despite the many reports linking NGF with changes in phosphorylation of cellular proteins, analysis of a cDNA sequence encoding a subunit of the NGF receptor which is sufficient for low-affinity binding of liqand has indicated no evidence for a protein-tyrosine kinase domain in the cytoplasmic region of this low affinity receptor (Johnson et al., 1986, Cell 47:545–554).

2.2. MAP2 Protein Kinase

Ribosomal protein S6 is a component of the eukaryotic 40S ribosomal subunit that becomes phosphorylated on multiple serine residues in response to a variety of mitogenic stimuli, including insulin, growth factors and various transforming proteins (for discussion, see Sturgill et al., 1988, Nature 334:715–718). Recently, an activated S6 kinase has been purified and characterized immunologically and molecularly (Ericson and Maller, 1986, J. Biol. Chem. 261:350–355; Ericson et al., 1987, Mol. Cell Biol. 7:3147–3155; Jones et al., 1988, Proc. Natl. Acad. Sci. U.S.A. 85:377–3381; Gregory et al., 1989, J. Biol. Chem. 264:18397–18401). Reactivation and phosphorylation of the S6 kinase occurs in vitro via an insulin-stimulated microtubule-associated protein-2 (MAP2) protein kinase providing further evidence for a protein kinase cascade (Sturgill, 1988, supra; Gregory et al., 1989, supra). MAP2 kinase has been observed to phosphorylate microtubule-associated protein-2 (MAP2) on both serine and threonine residues (Ray and Sturgill, 1987, Proc. Natl. Acad. Sci. U.S.A. 84:1502–1506; Boulton et al., 1991, Biochem. 30:278–286). These observations suggest that key steps in insulin action involve the sequential activation by phosphorylation of at least two serine/threonine protein kinases (Sturgill et al., 1988, Nature 334:715–718; Gregory et al., 1989, J. Biol. Chem. 264:18397–18401; Ahn et al., 1990, J. Biol. Chem. 265:11495–11501), namely, a MAP2 kinase and an S6 kinase. The MAP2 kinase appears to be activated transiently by insulin prior to S6 kinase activation.

The MAP2 kinase phosphorylates S6 kinase in vitro causing an increase in its activity (Gregory et al., 1989, J. Biol. Chem. 264:18397–18401; Sturgill et al., 1988, Nature, 334:715–718); thus, the MAP2 kinase is a likely intermediate in this protein kinase cascade. The finding that phosphorylation on threonine as well as tyrosine residues is required for MAP2 kinase activity (Anderson et al., 1990, Nature, 343:651–653) suggests that it, like many other proteins, is regulated by multiple phosphorylations. The phosphorylations may be transmitted through one or several signal transduction pathways.

In addition to stimulation by insulin, MAP2 kinase activity can be rapidly increased by a variety of extracellular signals which promote cellular proliferation and/or differentiation. In this regard, MAP2 kinase may be equivalent to pp42 (Cooper and Hunter, 1981, Mol. Cell. Biol. 1:165–178), a protein whose phosphotyrosine content increases following exposure to growth factors and transformation by viruses (Rossamondo et al., 1989, Proc. Natl. Acad. Sci. U.S.A. 86:6940–6943) and activation of the v-ros oncogene (Boulton et al., 1990, J. Biol. Chem. 265:2713–2719). For example, MAP2 kinase activity is stimulated in: terminally differentiated 3T3-L1 adipocytes in response to insulin (Ray and Sturgill, 1987, Proc. Natl. Acad. Sci. U.S.A. 84:1502–1506); in post-mitotic adrenal chromaffin cells in response to signals that induce catecholamine secretion (Ely et al., 1990, J. Cell Biol. 110:731–742); in PC12 cells in response to nerve growth factor-induced neuronal differentiation (Volonte et al., J. Cell Biol. 109:2395–2403; Miyasaka et al. J. Biol. Chem. 265:4730–4735) and in T lymphocytes (Nel et al., 1990, J. Immunol. 114:2683–2689). MAP2 kinase(s) are likely to play important roles in signal transduction in many different pathways and in a wide variety of cell types.

Ray and Sturgill (1988, J. Biol. Chem. 263:12721–12727) describes some chromatographic properties of a MAP2 kinase and reports the biochemical characteristics of the partially purified enzyme. MAP2 kinase was observed to have an affinity for hydrophobic chromatography matrices. The molecular weight of the partially purified enzyme was observed to be 35,000 by gel filtration chromatography and 37,000 by glycerol gradient centrifugation. MAP2 kinase activity of chromatographic fractions was found to correlate with the presence of a 40 kDa phosphoprotein detected by sodium dodecylsulfate polyacrylamide gel electrophoresis (SDS-PAGE). MAP2 kinase was observed to have a Km of 7 $\mu$M for ATP, and did not appear to utilize GTP. It has been observed that MAP2 kinase requires phosphorylation on tyrosine as well as serine/threonine residues for activity. Ray and Sturgill (supra) cite several problems encountered in the purification of MAP2 kinase, most notably, the presence of contaminating kinases observed to phosphorylate MAP2 in vitro. In addition, only very small amounts of only partially purified protein were available following chromatographic preparation. As discussed supra, Rossomando et al. (1989, Proc. Natl. Acad. Sci. U.S.A. 86:6940–6943) have suggested that MAP2 kinase may be a tyrosine-phosphorylated form of pp42, a low abundance 42-kDa protein which becomes transiently phosphorylated on tyrosine after cell stimulation with a variety of mitogens. Rossomondo et al. (supra) observed that phosphorylation of pp42 and activation of MAP2 kinase occur in response to the same mitogens, that the two proteins comigrate on two dimensional polyacrylamide gels and have similar peptide maps, and that the two proteins copurify during sequential purification on anion-exchange, hydrophobic interaction and gel-filtration media.

3. SUMMARY OF THE INVENTION

The present invention relates to a newly identified family of protein serine/threonine kinases which phosphorylate microtubule-associated protein 2 (MAP2). It is based, in part, on the cloning and characterization of novel MAP2 kinases designated extracellular signal-regulated kinase 1, 2, and 3 (ERK1, ERK2, ERK3) which are expressed in the central nervous system, and on the identification of another ERK family member, ERK4, with antisera. Accordingly, the term "MAP2 kinase" as used herein shall mean a member of the MAP2 family of kinases, including but not limited to ERK1, ERK2, and ERK3.

The present invention provides for recombinant nucleic acid molecules and proteins representing members of the MAP2 kinase family, and also for microorganisms, transgenic animals, and cell lines comprising recombinant MAP2 kinase molecules. In additional embodiments of the invention, the present invention provides for methods for assaying cellular factor activity, including, but not limited to, nerve growth factor activity, in which the activation of MAP2 kinase serves as an indicator of cellular factor activity. These methods may be extremely useful in screening compounds for the presence of a desired cellular factor activity. In specific embodiments, compounds which may be useful in the treatment of Alzheimer's disease, peripheral neuropathies, and diabetes may be identified using the methods of the invention.

4. DESCRIPTION OF THE FIGURES

FIG. 1. Schematic diagram of the relationship between hormone binding to a cellular receptor and consequent changes in the phosphorylation of proteins.

FIG. 2.

A. SDS-PAGE analysis of final Q-Sepharose #2 fractions isolated from NGF-treated or control PC12 cells. Aliquots of fractions obtained from the final purification column (Q-Sepharose#2) were concentrated and then analyzed via 15% SDS-PAGE. Note that fractions containing the most MAP2 kinase activity contained a prominent band (arrow) with a molecular weight of approximately 43,000 kD, as described for the insulin-stimulated MAP2 kinase BSA. Ovalbumin and cytochrome C are presented as size standards.

B. The complete nucleotide sequence (SEQ ID NO:1) of the ERK1 cDNA and its predicted protein product (SEQ ID NO:2). Asterisks denote the residues most conserved among all protein kinases. The sequences of the nine tryptic peptides that were sequenced are underlined. All residues precisely determined by the amino acid sequencing matched the cDNA encoded protein sequence; questionable residues were verified from the cDNA encoded protein sequence. The fourth and seventh peptides indicated represented the minor peptide components described in the text.

Figures 1, 2A:
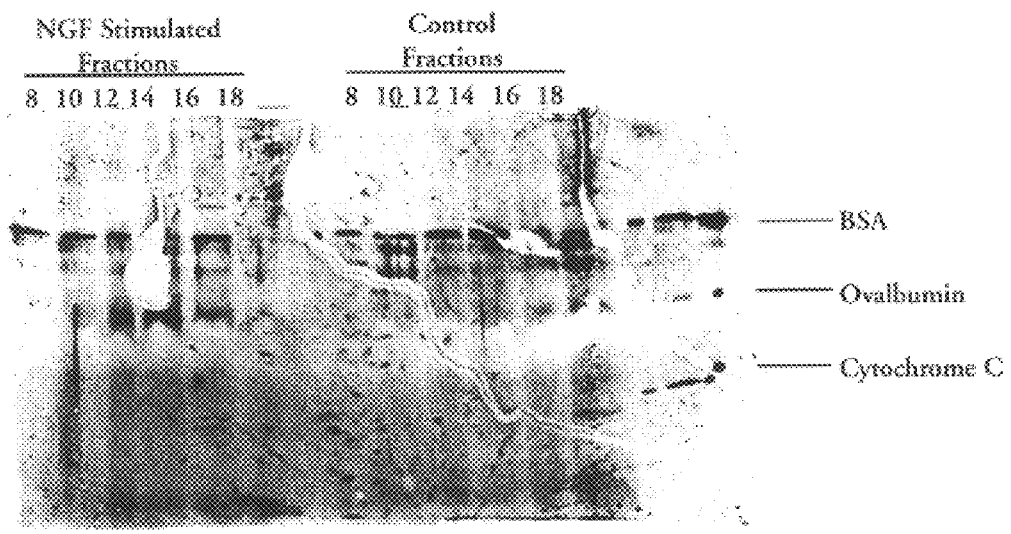
Figures 2, 2A:
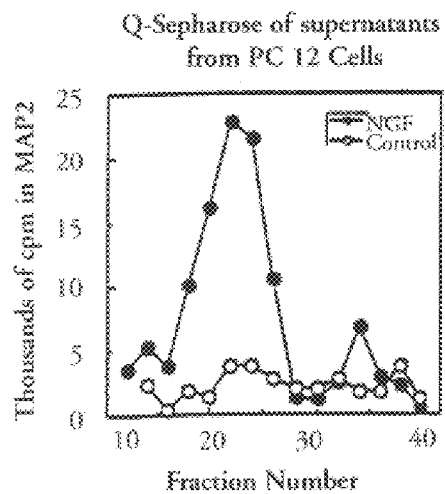
Figures 2, 2A, 3:
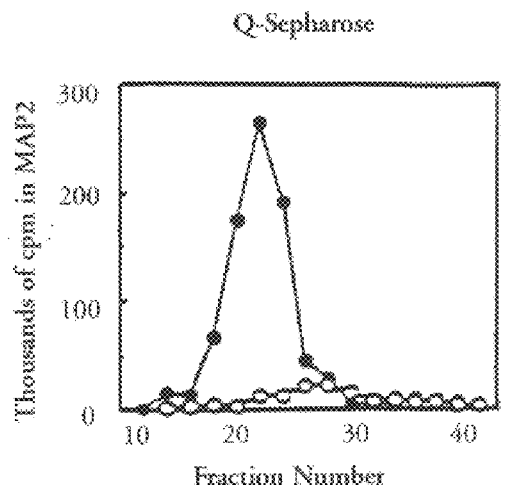

FIG. 3. Nucleotide and predicted protein sequences of ERK2 and ERK3 cDNAs and ERK1Ψ pseudogene. Initiation and termination codons are boxed; approximate locations of protein kinase subdomains indicated by roman numerals; asterisks denote residues most conserved among all protein kinases (Ranks et al., 1988, Science 241:42–52); and pound signs denote which of these residues are not conserved in the indicated sequences.

A. Nucleotide (SEQ ID NO:3) and predicted protein (SEQ ID NO:4) sequence of one of the two ERK2 cDNA clones; protein coding region of the other ERK2 cDNA matches exactly, although sequences in the flanking regions diverged.

B. Complete nucleotide (SEQ ID NO:5) and predicted protein (SEQ ID NO:6) sequence of one of two ERK3 cDNA clones analyzed; sequence of the other ERK3 cDNA matches exactly although there were differences in the amounts of flanking sequence.

C. Alignment of partial sequence of ERK1Ψ with the ERK1 nucleotide sequences; only amino acid differences (including the premature termination codon of ERK1Ψ, which is boxed) from the ERK1 protein sequence are indicated. Dashes indicate deletions in both the nucleotide and amino acid sequences.

Figures 2, 2A, 3, 4:
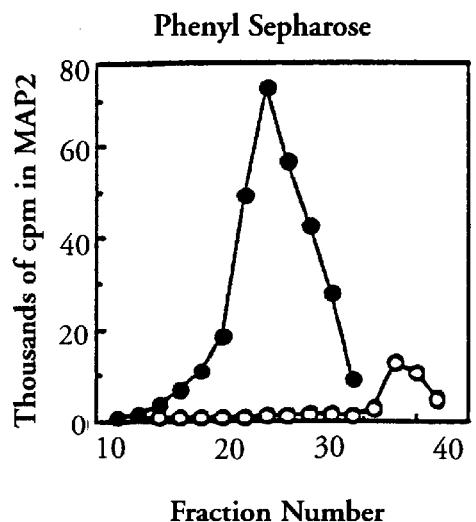

FIG. 4. Comparison of ERKs with FUS3, KSS1 and human cdc2 protein sequences.

A. Computer-generated alignments (MacVector Computer Analysis Software, International Biotechnologies, Inc., New Haven, Conn.) were visually optimized. Roman numerals indicate subdomains conserved in protein kinases (Hanks et al., 1988, Science 241:42–52). Dots indicate identity to ERK1 sequence, dashes indicate spaces introduced to improve sequence alignments.

B. Percent identities between the sequences aligned in A, determined over the length of the cdc2+sequence; mismatches, insertions and deletions between two sequences all weighted equally.

Figures 2, 2A, 3, 4, 5:
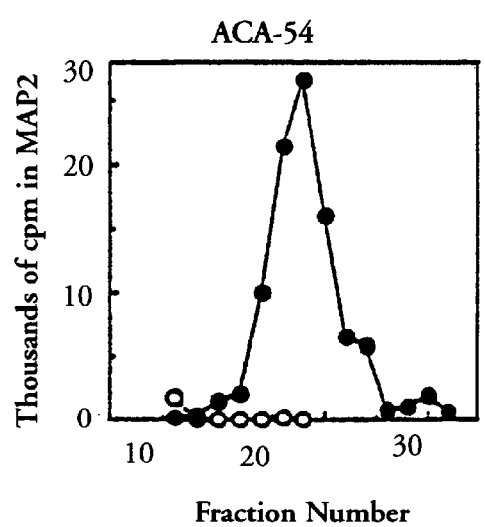

FIG. 5. Use of ERK1-, ERK2- and ERK3-specific probes provides evidence for additional ERK genes.

A. Specificity of each of the ERK probes (described in Materials and Methods) was demonstrated by hybridizing three triplicate Southern blots, each with linearized plasmids containing the ERK1, ERK2 and ERK3 cDNA inserts (as marked for each lane), with each of the ERK probes as indicated below the blots.

B. Probing of Southern blots containing EcoR1-digested rat and human genomic DNA with each of the ERK-specific probes; sizes of DNA fragments indicted in kilobases.

C. Probing of Southern blots containing rat genomic DNA digested with Bgl2, BamH1 and Hind3 with each of the ERK-specific probes; sizes of DNA fragments indicated in kilobases.

Figures 2, 2A, 3, 4, 5, 6:
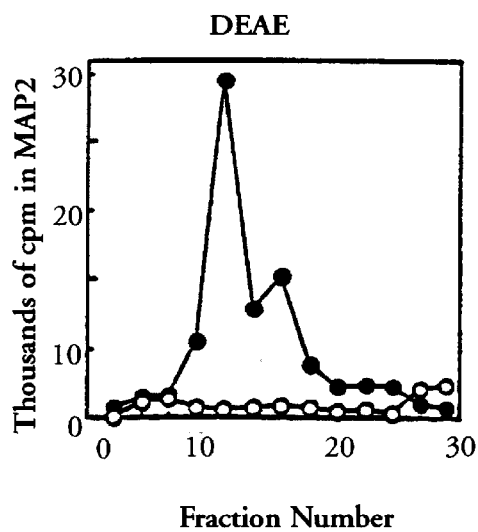

FIG. 6. Independent regulation of ERK transcripts in tissues, developmentally, in cultured astroglia and in the P19 embryocarcinoma cell line.

A. Distinct patterns of expression for each of the ERKs within adult nervous system, in adult peripheral tissues, and in placenta. Specific probes for each of the ERKs (see FIG. 3) were hybridized to Northern blots containing 10 μg of RNA from the indicated adult tissues and brain regions. ADR, adrenal; RET, retina; SC.N., sciatic nerve; S.C., spinal cord; A.BR, adult brain; CBL, cerebellum; HBR, hindbrain; MBR, midbrain; DIEN, diencephalon; STR, striatum; HIP, hippocampus; CTX, neocortex; OLF, olfactory bulb; SKIN, skin; HRT, heart; MUS, muscle; LUNG, lung; INT, intestine; KID, kidney; LIV, liver; SPL, spleen; THY, thymus; PLAC, placenta.

B. ERK transcripts are developmentally regulated within the nervous system and in peripheral tissues. Ten μg of total RNA isolated from the indicated developmental stages (E: embryonic day; P:post-natal day; AD: adult) of rat brain, spinal cord, hippocampus (HIPP), liver and heart were compared for hybridization to each of the ERK-specific probes.

C. ERK2 and ERK3 transcripts expressed at low levels in cultured astroglia. Ten micrograms of total RNA from adult rat brain (BRN) or cultured astroglia (AST) probed with each of the ERK specific probes, as indicated.

D. Independent regulation of individual ERK genes during differentiation of P19 embryocarcinoma cells. Ten micrograms of total RNA from adult rat brain or from undifferentiated P19 cell (STEM), retinoic acid-induced (NEUR) or DMSO-induced (MUSC) were used to prepare replicate Northern blots which were probed as indicated. LANGFR signifies a probe for the low-affinity NGF receptor, the GAPDH control probe verifies that equal amounts of RNA were loaded in each lane.

Figures 2, 2A, 3, 4, 5, 6, 7:
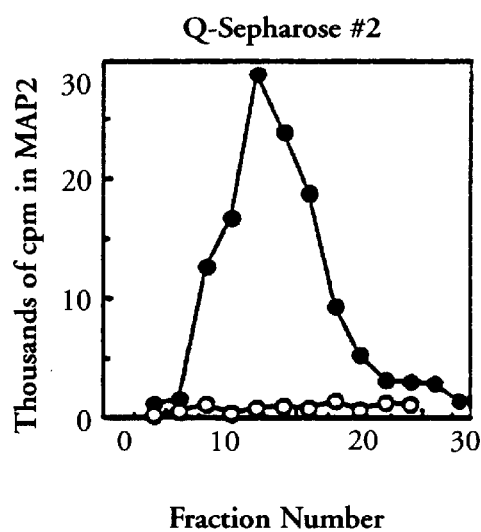

FIGURE 7. Expression of active ERK2 in $E.\ coli$.

A. Silver stained gels of equal amounts of protein from lysates of $E.\ coli$ expressing ERK2 or vector alone. The arrow denotes recombinant ERK2.

B. Immunoblot with antiserum 837 of the same amount of $E.\ coli$ extracts shown in A and about 40 ng of partially purified ERK1.

C. Silver stain (left) and autophosphorylation (right) of 162, 270, or 540 ng of purified recombinant ERK2.

D. Kinase activity of purified recombinant ERK2 incubated for 0, 15, 30, 45, and 60 minutes with MBP.

Figure 8A:
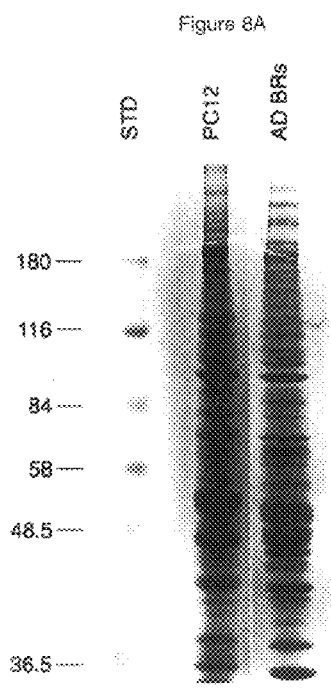

FIG. 8. Specificity of antipeptide antibodies.

A. Coomassie blue stain of 100 μg of soluble protein from PC12 cells and adult rat brain.

B. Immunoblot of partially purified ERK1, recombinant ERK2, and 100 μg of soluble protein from PC12 cells, 100 μg of soluble (s) and particulate (p) protein from embryonic brain (EM BR) and adult brain (AD BR) (prepared as described in Boulton et al., 1991, Biochem. 30:278–286) with antiserum 956.

C. Duplicate blot probed with antiserum 837.

FIG. 9. Immunoprecipitation of $^{32}$P-labeled ERK proteins from insulin-stimulated Rat 1 HIRc B cells and NGF-stimulated PC12 cells.

A. ERK1 was immunoprecipitated with antiserum 837 from $^{32}$P-labeled (left) Rat 1 HIRc B cells with (+) or without (−) exposure to insulin and (right) PC12 cells with (+) or without (−) exposure to NGF. Tick marks indicate molecular weight standards of 116, 84, 58, 48.5, 36.5, and 26.6 kDa.

B. As in part A with and without NGF but with denaturing immunoprecipitation.

C. Phosphoamino acid analysis of immunoprecipitated ERK1 from NGF-treated PC12 cells. The positions of the phosphoamino acid standards are noted. After 4 hours of labeling, ERK1 was only phosphorylated on serine in the absence of NGF.

Figure 10:
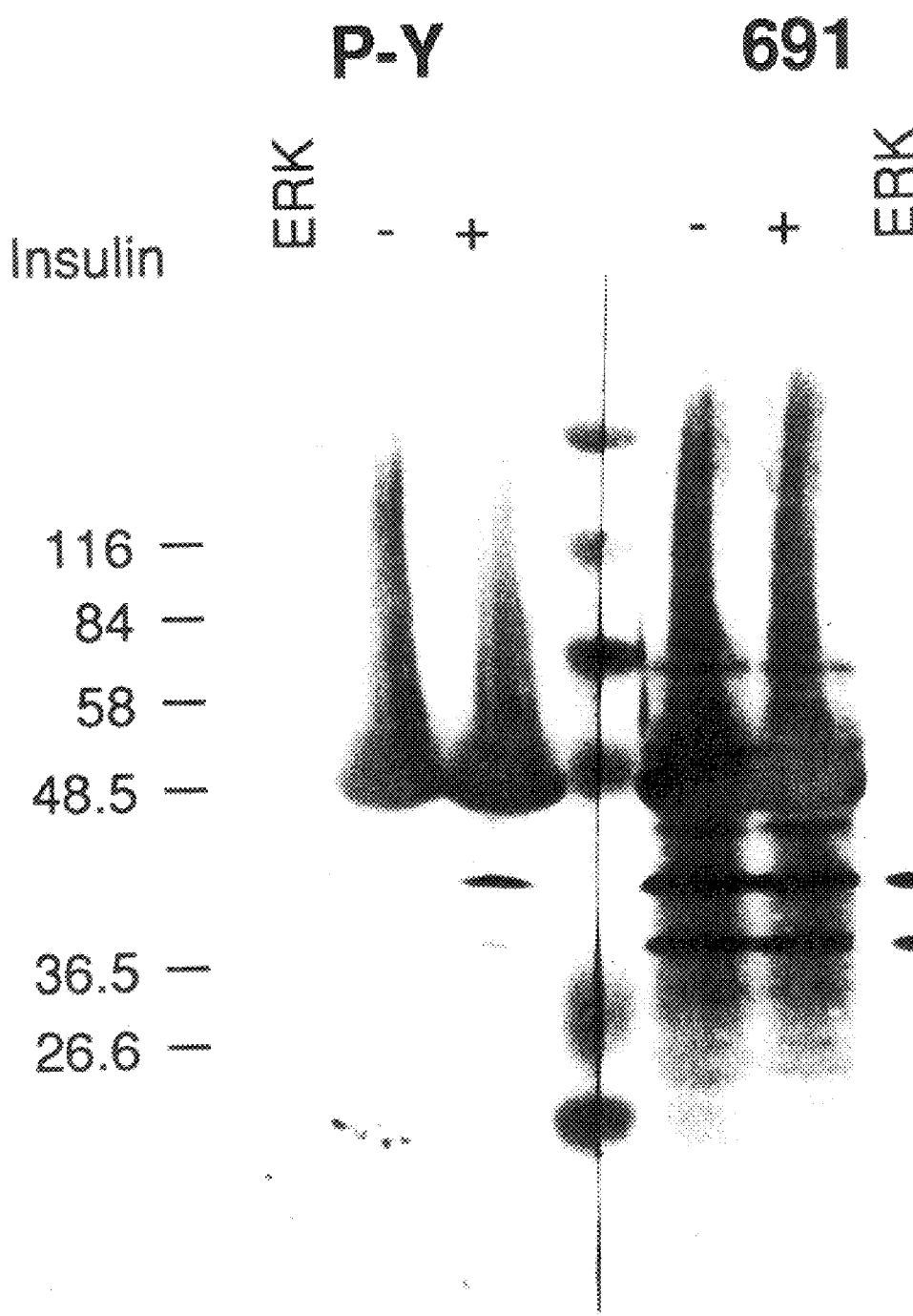

FIG. 10. Imunoblot of immunoprecipitated ERK proteins. ERKs were immunoprecipitated from 1 mg of supernatant protein from insulin-treated (+) or untreated (−) Rat 1 HIRc B cells under denaturing conditions using antiserum 837. The immunoprecipitated proteins were resolved by SDS-PAGE and probed with either antibodies to phosphotyrosine (P-Y) or with ERK antiserum 691. Lanes labeled ERK contain an aliquot of a phenyl-Sepharose fraction containing both ERKs 1 and 2.

Figure 11A:
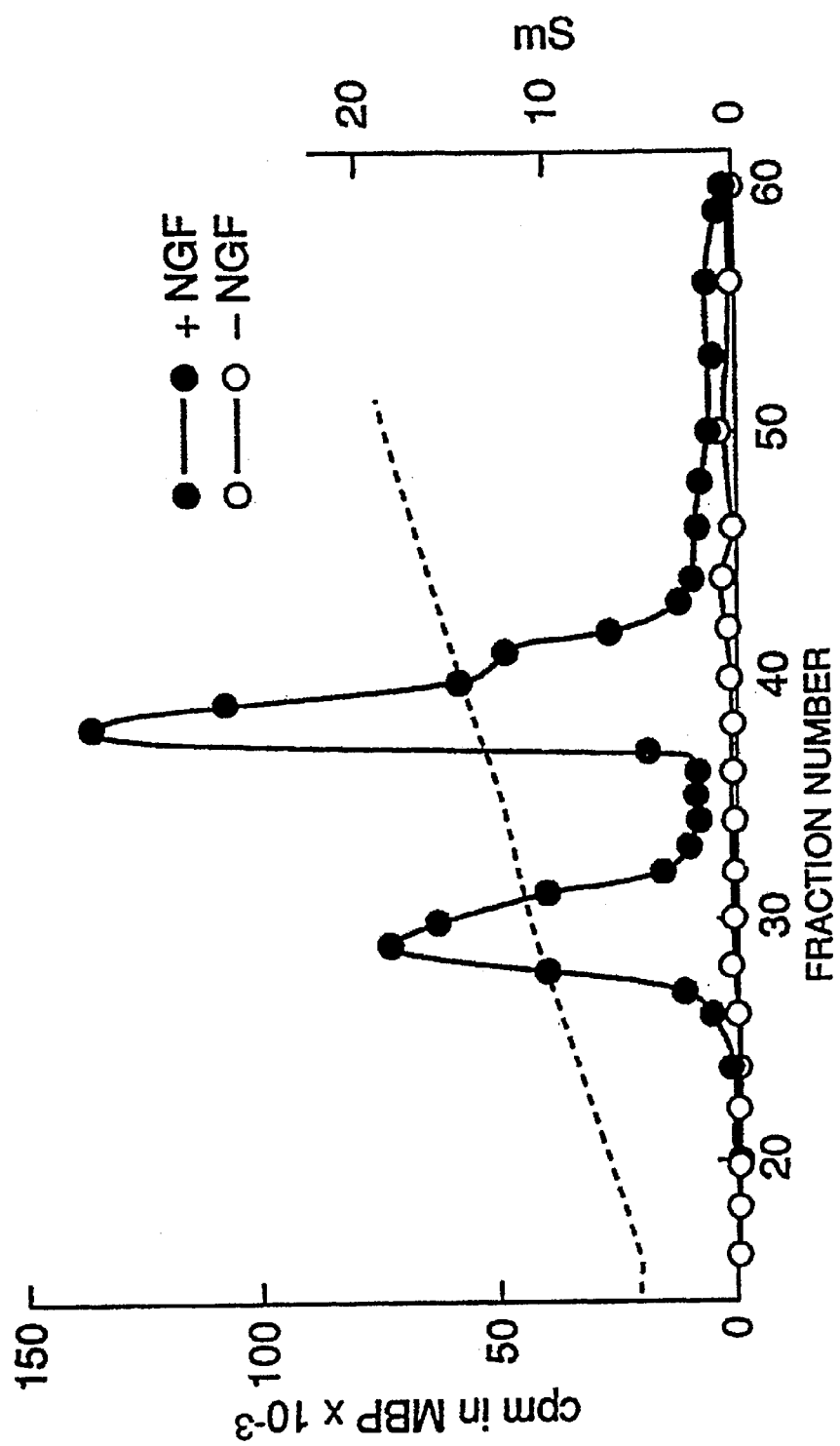

FIG. 11. Chromatography of supernatants from NGF-treated or untreated PC-12 cells on Mono Q. 10 mg of protein from supernatants of PC12 cells either untreated or treated with NGF were chromatographed on a Mono Q column. Kinase activity with MBP is shown in the upper panel. Numbered fractions were precipitated and immunoblotted with the indicated antibody, either 956, 837 or antiphosphotyrosine (αP-Y).

5. DETAILED DESCRIPTION OF THE INVENTION

For purposes of clarity of disclosure, and not by way of limitation, the detailed description of the invention will be divided into the following subsections:

(i) cloning of the MAP2 kinase protein;

(ii) identification of additional members of the MAP2 protein kinase family;

(iii) expression of recombinant MAP2 protein kinase;

(iv) generation of anti-MAP2 protein kinase antibodies;

(v) bioassays for MAP2 kinase activation; and (vi) utility of the invention.

5.1. Cloning of the MAP2 Protein Kinase

According to the present invention, MAP2 protein kinase may be cloned by identifying cloned nucleic acids which contain sequences homologous to known MAP2 kinase sequence, for example, but not limited to, the sequences set forth in FIGS. 2B (SEQ ID NO:1), 3A (SEQ ID NO:3), and 3B (SEQ ID NO:5), and/or contained in plasmids pBS-rERK1, pBS-rERK2, or pBS-rERK3, as deposited with the ATCC and assigned accession numbers 40808, 40809, and 75009 respectively. Alternatively, it may be desirable to obtain such sequence information from purified MAP2 kinase protein.

Purified MAP2 kinase may be obtained from tissues which contain MAP2 kinase activity, including, but not limited to, T lymphocytes, insulin-treated, terminally differentiated 3T3-L1 adipocytes, post-mitotic adrenal chromaffin cells induced to secrete catecholamines, PC12 cells treated with nerve growth factor, brain tissue, or insulin-treated rat 1 HIRc B cells, as well as lower eukaryotes such as sea star and *Xenopus laevis* oocytes. Purification of MAP2 kinase from PC12 cells appears to parallel purification of MAP2 kinases from insulin treated rat 1 HIRc B cells (FIG. 2A).

In a specific embodiment of the invention, and not by way of limitation, MAP2 kinase may be purified to a large extent, as follows (Boulton et al., 1991, Biochem. 30:278–286). Cells containing MAP2 kinase may be used to prepare a cell free extract comprising a crude preparation of MAP2 kinase. For example, either PC12 cells may be cultured in DME medium containing 10% fetal bovine serum and 5% horse serum, and then, prior to NGF treatment, may be incubated in serum-free medium for about one hour. NGF at a concentration of about 4 mM may then be added, and the cells may be incubated for 5 minutes. Alternatively, insulin-treated Rat 1 HIRc B cells may be used. The medium may then be removed and the cells rinsed and scraped into iced homogenization solution that contains 20 mM p-nitrophenylphosphate, 20 mM Tris-HCl, pH 7.5, 1 mM EGTA, 50 mM sodium fluoride, 50 μM sodium orthovanadate and 5 mM benzamidine (MAP2 kinase). Equal numbers of dishes of untreated cells may desirably be harvested as controls. All further steps are preferably performed at 4° C. Cells may be broken with 30–50 strokes of a Dounce homogenizer and homogenates may be centrifuged at 4000×g for 5 minutes. The supernatants may then be centrifuged at 97,000×g for 60 minutes. The resulting supernatants may then be assayed, preferably immediately, then frozen in liquid nitrogen.

For purification of MAP2 kinase, soluble fractions (225–300 ml) combined from 150 to 200 150-cm$^2$ dishes of insulin-treated Rat 1 HIRc Bell cells may be adjusted to a conductivity of 3.5 mS (with water) and to concentrations of 40 μM cAMP, 0.5 mM phenylmethylsulfonylfluoride and 0.1 μM pepstatin prior to chromatography on a Q-Sepharose column (1.5×19 cm). The column may be washed with 4 to 5 volumes of buffer A (10% glycerol, 25 mM Tris-HCl, pH 7.5, 50 μM sodium orthovanadate, 1 mM dithiothreitol, 50 mM NaF, 20 mM β-glycerol phosphate, 1 mM EGTA, 10 mM benzamidine, 10 mM p-nitrophenylphosphate, 0.5 mM phenylmethylsulfonyl fluoride, and 0.1 μM pepstatin) containing 40 μM cAMP. Protein may then be eluted by a gradient of 0–0.4 M NaCl in buffer A. Fractions containing stimulated MAP2 kinase activity may be pooled and applied to a phenyl-Sepharose column (1.5×18 cm). The column may then be washed with 5 column volumes of buffer A containing 0.25 M NaCl and protein may be eluted with a descending gradient of 0.25–0.025 M NaCl plus an ascending gradient of 0–65% ethylene glycol in buffer A without glycerol. Kinase activity may be pooled from the phenyl-Sepharose column and applied directly to a 5 ml column (1.5×3 cm) of S-Sepharose followed by a 5 ml column of phosphocellulose (1.5×3 cm). In both cases, unadsorbed material containing MAP2 kinase activity and 2 column volumes of wash may be collected. The MAP2 kinase activity from the phosphocellulose column may be applied directly to a QAE-Sepharose column (1×24 cm). The column may be washed with 5 volumes of buffer A and protein may be eluted with a gradient of 0–0.4 M NaCl in buffer A. The fractions containing MAP2 kinase activity may then be pooled, Brij-58 may be added to give a final concentration of 0.01% (included in all subsequent steps), and the sample may be concentrated by ultrafiltration to 1.5–2 ml in order to load onto an Ultrogel AcA54 column (1×112 cm) equilibrated in buffer A containing 0.2 M NaCl and 0.01% Brij-58. Fractions from the gel filtration column may be collected into tubes containing 2.4 mM leupeptin. The fractions containing activity may be concentrated and diluted with 25 mM Tris, pH 7.5, 1 mM DTT, 10 mM sodium phosphate, 0.1 μM pepstatin, 0.5 mM phenylmethyl sulfonyl fluoride containing 0.01% Brij-58 until the conductivity is reduced to 3 mS and then may be applied to DEAE-cellulose (0.7×18 cm). The activity may be eluted with a gradient of 0–0.25 M NaCl in buffer A. Fractions containing activity may be pooled, and, as necessary, concentrated and diluted as above to apply to either a Mono Q HR 5/5 or a Q-Sepharose (0.5×9 cm) column. The MAP2 kinase activity may be eluted with a gradient of 0–0.25 M NaCl (from Mono Q) in buffer A. Fractions may be assayed and then immediately frozen in liquid nitrogen.

Purified MAP2 kinase may then be digested with trypsin and the resulting peptides subjected to HPLC (Abersold et al., 1987, Proc. Natl. Acad. Sci. U.S.A. 84:6970–6974) as described in section 6.1, infra. The peptides from one of the resulting peaks may then be subjected to a second chromatographic separation. In order to determine fragments of MAP2 kinase protein sequence accurately, it may be necessary to perform repeated purification of peptides and to discriminate between major and minor component peptides, as would be recognized by one skilled in the art.

Peptides may be sequenced by any method known in the art. For example, fractions containing the enzyme may be pooled and final concentrations of 0.05% Lubrol and 8.5% trichloroacetic acid (w/v) may be added to precipitate the protein. After washing with acetone,the protein may be dissolved in electrophoresis buffer and 250 pmol may be loaded onto a 10% polyacrylamide gel in SDS. Protein may be electrophoretically transferred to nitrocellulose (Schleicher and Schuell, Keene, N.H.). The 43 kDa band may be excised for in situ digestion with trypsin (Abersold et al., 1987, Proc. Natl. Acad. Sci. U.S.A. 84:6970–6974), leaving the minor component, which migrates only slightly faster, on the nitrocellulose. Peptides released from the excised piece of nitrocellulose may be subjected to HPLC on a Model 130A chromatography system (Applied Biosystems, Inc., Foster City, Calif.) equipped with a 2.1× 100 mm Applied Biosystems RP-300 column. Separations may be performed in 0.1% trifluoroacetic acid at a flow rate of 50 $\mu$l/min using a gradient of 0–70% (v/v) acetonitrile of 100-min duration. Absorbency of the eluate may be monitored at 214 nm and the components that eluted may be collected manually. Peptides may be dried onto 1 cm discs of Whatman GF/C paper and sequenced using an Applied Biosystems, Inc. Model 470A amino acid sequencer equipped with a Model 120A phenylthiohydantoin analyzer, according to manufacturer's specifications.

The purification of suitable amounts of MAP2 kinase protein to permit microsequencing makes possible the cloning of a MAP2 kinase cDNA. A strategy for such cloning might be to generate a complementary oligonucleotide probe, based on a segment of known amino acid sequence, and to use this probe to screen cDNA libraries generated from tissue presumed to synthesize mRNA encoding MAP2 kinase is as follows. First, the amino acid sequence derived from purified MAP2 kinase protein may be used to deduce oligonucleotide primers which may be generated and used in standard screening techniques or used in polymerase chain reaction (PCR) (Saiki et al., 1985, Science 230:1350–1354). Because of the degeneracy of the genetic code, in which several triplets may specify the same amino acid, several oligonucleotides should be synthesized for a given amino acid sequence, in order to provide for multiple potential nucleotide sequence combinations; the resulting oligonucleotides are referred to as degenerate primers. For example, in a specific embodiment of the invention, a series of degenerate oligonucleotides may be synthesized that correspond to the coding or anti-coding strands for segments of tryptic peptide sequences obtained from purified MAP2 kinase protein. The oligonucleotides may desirably contain non-degenerate tails at their 5' ends; the tail of each coding strand oligonucleotide may contain, for example, an EcoR1 restriction site, while the tail of each anti-coding strand oligonucleotide may, for example, contain a Sall restriction site. Each coding strand oligonucleotide may then be combined with each anti-coding oligonucleotide in individual PCR reactions using cDNA from Rat 1 cells as template; the PCR reactions and the preparation of the genomic and cDNA templates may then be performed as described in Maisonpierre, C. et al., 1990, Science 247:1446–1451 and Bothwell, A., Yancopoulos, G. and Alt, F., 1990, "Methods for Cloning and Analysis of Eukaryotic Genes", Jones and Bartlett, Boston, Mass. The amplified product obtained using, for example, the QYIGEG SEQ ID NO:7coding oligonucleotide and the DLKPSN SEQ ID NO:9 anti-coding oligonucleotide (designated QYDL SEQ ID NO:11) may then be isolated using a Sephadex G-50 spin column, digested with EcoR1 and Sall, gel purified using 2% Nusieve (FMC Bioproducts),and subcloned into a vector comprising suitable restriction sites, such as the pGEM4Z vector (Promega).

A suitable library, believed to be likely to contain a MAP2 kinase gene, may then be screened with labeled nucleic acid probe (for example, subcloned PCR product radiolabeled using a PCR-based protocol (Maisonpierre et al., 1990, Science 247:1446–1451)). Examples of a suitable library would include a rat brain or T lymphocyte cDNA library or a cDNA library produced from PC12 cells or post-mitotic adrenal chromaffin cells, to name but a few. Hybridization conditions may be performed as described in Maisonpierre et al. (1990, Science 247:1446–1451) or using any standard techniques; washing of filters may preferably be performed first at low stringency (2×SSC (20 mM sodium citrate, pH 7.0, 0.15 M NaCl), 0.1 SDS at 60° C.) and then at high stringency (0.2×SSC, 0.1% SDS at 60° C.).

Once obtained, a MAP2 kinase gene may be cloned or subcloned using any method known in the art. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, or Bluescript® (Stratagene) plasmid derivatives. Recombinant molecules can be introduced into host cells via transformation, transfection, infection, electroporation, etc.

The MAP2 kinase gene may be inserted into a cloning vector which can be used to transform, transfect, or infect appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. It may prove advantageous to incorporate restriction endonuclease cleavage sites into the oligonucleotide primers used in polymerase chain reaction to facilitate insertion into vectors. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and NAP2 kinase gene may be modified by homopolymeric tailing.

In specific embodiments, transformation of host cells with recombinant DNA molecules that incorporate an isolated MAP2 kinase gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

According to a preferred embodiment of the invention, once a cDNA-derived clone encoding MAP2 kinase has been generated, a genomic clone encoding MAP2 kinase may be isolated using standard techniques known in the art. For example, a labeled nucleic acid probe may be derived from the MAP2 kinase clone, and used to screen genomic DNA libraries by nucleic acid hybridization, using, for example, the method set forth in Benton and Davis (1977, Science 196:180) for bacteriophage libraries and Grunstein and Hogness (1975, Proc. Natl. Acad. Sci. U.S.A. 72:3961–3965) for plasmid libraries. Retrieved clones may then be analyzed by restriction-fragment mapping and sequencing techniques according to methods well known in the art.

Furthermore, additional cDNA clones may be identified from a cDNA library using the sequences obtained according to the invention.

5.2. Identification of Additional Members of the MAP2 Protein Kinase Family

The present invention provides for recombinant nucleic acid molecules corresponding to mammalian nucleic acids which are homologous to the nucleic acid sequences substantially as depicted in FIGS. 2B (SEQ ID NO:1), 3A (SEQ ID NO:3) and 3B (SEQ ID NO:5) or portions thereof of at least 10 nucleotides.

According to the present invention, by screening a DNA library (comprising genomic DNA or, preferably, cDNA) with oligonucleotides corresponding to MAP2 kinase sequence derived either from protein sequence data or from the nucleic acid sequence set forth in FIGS. 2B (SEQ ID NO:1), 3A (SEQ ID NO:3) and 3B (SEQ ID NO:5), clones may be identified which encode distinct members of the MAP2 kinase family, as exemplified in Section 7, infra, in which additional members of the MAP2 kinase family were identified. By decreasing the stringency of hybridization, the chances of identifying somewhat divergent members of the family may be increased. It may also be desirable to use sequences substantially shared by members of the MAP2 kinase family which have been sequenced preferably, for example, sequences from domains V or VI; such highly conserved regions may be particularly useful in identifying additional members of the MAP2 kinase family. Library screening may be performed using, for example, the hybridization technique of Benton and Davis (1977, Science 196:180) or Grunstein and Hogness (1975, Proc. Natl. Acad. Sci. U.S.A. 72:3961–3965). Clones identified by hybridization may then be further analyzed, and new family members may be identified by restriction fragment mapping and sequencing techniques according to methods well known in the art.

It may be desirable to utilize polymerase chain reaction (PCR) technology (Saiki et al., 1985), Science 230:1350–1354) to identify additional members of the MAP2 protein kinase family. For example, sense and antisense primers corresponding to known MAP2 protein kinase sequence (which preferably appears to be conserved among characterized members of the MAP2 protein kinase family) may be used in PCR, with cDNA obtained from cells which produce MAP2 kinase as template. It may be desirable to design these primers such that they include restriction enzyme cleavage sites which may facilitate the insertion of the products of PCR into appropriate cloning vectors. The products of PCR may be inserted into suitable vectors as set forth in Section 5.1, supra, and the resulting clones may then be screened for new family members. Such screening may be performed using standard techniques, including hybridization analysis using probes corresponding to known MAP2 kinase sequence. For example, a series of probes representing different regions of an already characterized MAP2 kinase protein may be hybridized at low stringency to duplicate filters carrying DNA from clones generated using PCR, as outlined above. It may be observed that various clones may hybridize to some probes, but not others. New family members may also be identified by increasing the stringency of the hybridization conditions, wherein new members not identical to probes derived from known members (e.g. ERK1, ERK2 or ERK3) would hybridize less strongly at higher stringency. Alternatively, new family members may be identified by restriction mapping or sequencing analysis using standard techniques to reveal differences in restriction maps or sequences relative to known family members.

5.3. Expression of Recombinant MAP2 Protein Kinase

The present invention provides for recombinant MAP2 protein kinase molecule comprising the amino acid sequence substantially as depicted in FIGS. 2B (SEQ ID NO:2), 3A (SEQ ID NO:4) or 3B (SEQ ID NO:6), or a portion thereof, which has a molecular weight, by SDS-PAGE, of between about 41 and 48 kDa, or about 62–63 kDA, or which comprises a portion homologous to the yeast FUS3 or KSS1 protein kinase as well as a short amino terminal extension or which has a carboxy terminal extension of about 180 amino acids. The present invention also provides for mammalian MAP2 protein kinases homologous to the above-mentioned molecules.

In order to express recombinant MAP2 kinase, the nucleotide sequence coding for a MAP2 kinase protein, or a portion thereof, can be inserted into an appropriate expression vector, i.e., a vector which contains the necessary elements for the transcription and translation of the inserted protein-coding sequence. The necessary transcriptional and translation signals can also be supplied by the native MAP2 kinase gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding MAP2 kinase protein or peptide fragment may be regulated by a second nucleic acid sequence so that MAP2 kinase protein or peptide is expressed in a host transformed with the recombinant DNA molecule. For example, expression of MAP2 kinase Day be controlled by any promoter/enhancer element known in the art. Promoters which may be used to control MAP2 kinase expression include, but are not limited to, the SV40 early promoter region (Bernoist and Chambon, 1981, Nature 290:304–310), [the CMV promoter] the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionine gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing MAP2 kinase gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted MAP2 kinase gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the MAP2 kinase gene is inserted within the marker gene sequence of the vector, recombinants containing the MAP2 kinase insert can be identified by the absence of the marker gene function. In the third approach, recombinant expression vectors can be identified by assaying the foreign gene product expressed by the recombinant. Such assays can be based, for example, on the physical or functional properties of the MAP2 kinase gene product in bioassay systems as described supra, in Section 5.2. However, if cells containing MAP2 kinase expression constructs contain intrinsic MAP2 kinase, activity resulting from the construct can be distinguished from endogenous kinase activity (e.g. put a distinguishing tag on the recombinant molecule) or by subtracting background levels of endogenous kinase.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered NAP2 kinase protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous MAP2 kinase protein. Furthermore, different vector/host expression systems may effect processing reactions such as proteolytic cleavages to different extents.

Once a recombinant which expresses the MAP2 kinase gene is identified, the gene product should be analyzed. This can be achieved by assays based on the physical or functional properties of the product.

Once the MAP2 kinase protein is identified, it may be isolated and purified by standard methods including chromatography (e.g., ion exchange, affinity, and sizing column chromatography), centrifugation, differential solubility, or by any other standard technique for the purification of proteins.

The presence of functional MAP2 kinase activity may be determined as set forth in section 5.5, infra.

5.3.1. MAP2 Gene Kinase Genes and Proteins

Using the methods detailed supra and in Example Sections 6 and 7, infra, the following nucleic acid sequences were determined, and their corresponding amino acid sequences deduced. The sequences of two rat MAP2 kinase cDNAs were determined, and are depicted in FIGS. 2B (SEQ ID NO:1), 3A (SEQ ID NO:3) and 3B (SEQ ID NO:5). Each of these sequences, or their functional equivalents, can be used in accordance with the invention. Additionally; the invention relates to MAP2 kinase genes and proteins isolated from porcine, ovine, bovine, feline, avian, equine, or canine, as well as primate sources and any other species in which MAP2 kinase activity exists. The present invention also provides for ERK4, as identified and described in Section 7, infra, which corresponds to a protein having a molecular weight of about 45 kDa. The invention is further directed to homologous subsequences of MAP2 kinase nucleic acids comprising at least ten nucleotides, such subsequences comprising hybridizable portions of the MAP2 kinase sequence which have use, e.g., in nucleic acid hybridization assays, Southern and Northern blot analyses, etc. The invention also provides for MAP2 kinase proteins, fragments and derivatives thereof, according to the amino acid sequences set forth in FIGS. 2B (SEQ ID NO:2), 3A (SEQ ID NO:4) and 3B (SEQ ID NO:6) or their functional equivalents and for proteins homologous to such proteins, such homology being of at least about 30 percent. The invention also provides fragments or derivatives of MAP2 kinase proteins which comprise antigenic determinant(s) or which are functionally active or which are at least six amino acids in length. As used herein, functionally active shall mean having the capacity to phosphorylate MAP2 or other relevant substrates (e.g. MBP, S6 kinase; see Section 5.5, infra).

For example, the nucleic acid sequences depicted in FIGS. 2B (SEQ ID NO:1), 3A (SEQ ID NO:3) and 3B (SEQ ID NO:5) can be altered by substitutions, additions or deletions that provide for functionally equivalent molecules. Due to the degeneracy of nucleotide coding sequences, other DNA sequences which encode substantially the same amino acid sequence as depicted in FIGS. 2B (SEQ ID NO:2), 3A (SEQ ID NO:4) and 3B (SEQ ID NO:6) may be used in the practice of the present invention. These include but are not limited to nucleotide sequences comprising all or portions of the MAP2 kinase genes depicted in FIGS. 2B (SEQ ID NO:1), 3A (SEQ ID NO:3) and 3B (SEQ ID NO:5) which are altered by the substitution of different codons that encode a functionally equivalent amino acid residue within the sequence, thus producing a silent change. Likewise, the MAP2 kinase proteins, or fragments or derivatives thereof, of the invention include, but are not limited to, those containing, as a primary amino acid sequence, all or part of the amino acid sequence substantially as depicted in FIGS. 2B (SEQ ID NO:2), 3A (SEQ ID NO:4) and 3B (SEQ ID NO:6) including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are MAP2 kinase proteins or fragments or derivatives thereof which are differentially modified during or after translation, e.g., by phosphorylation, glycosylation, proteolytic cleavage, linkage to an antibody molecule or other cellular ligand, etc. For example, it may be desirable to modify the sequence of a MAP2 kinase such that specific phosphorylation, i.e. serine threonine, is no longer required or as important.

In addition, the recombinant MAP2 kinase encoding nucleic acid sequences of the invention may be engineered so as to modify processing or expression of MAP2 kinase. For example, and not by way of limitation, a signal sequence may be inserted upstream of MAP2 kinase encoding sequences to permit secretion of MAP2 kinase and thereby facilitate harvesting or bioavailability.

Additionally, a given MAP2 kinase can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, et al., 1978, J. Biol. Chem. 253:6551), use of TAB® linkers (Pharmacia), etc.

5.4. Generation of Anti-MAP2 Protein Kinase Antibodies

According to the invention, MAP2 kinase protein, or fragments or derivatives thereof, may be used as immunogen to generate anti-MAP2 kinase antibodies. By providing for the production of relatively abundant amounts of MAP2 kinase protein using recombinant techniques for protein synthesis (based upon the MAP2 kinase nucleic acid sequences of the invention), the problem of limited quantities of MAP2 kinase has been obviated.

To further improve the likelihood of producing an anti-MAP2 kinase immune response, the amino acid sequence of MAP2 kinase may be analyzed in order to identify portions of the molecule which may be associated with increased immunogenicity. For example, the amino acid sequence may be subjected to computer analysis to identify surface epitopes which present computer-generated plots of hydrophilicity, surface probability, flexibility, antigenic index, amphiphilic helix, amphiphelic sheet, and secondary structure of MAP2 kinase. Alternatively, the deduced amino acid sequences of MAP2 kinase from different species could be compared, and relatively non-homologous regions identified; these non-homologous regions would be more likely to be immunogenic across various species.

For preparation of monoclonal antibodies directed toward MAP2 kinase, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of MAP2 kinase. For the production of antibody, various host animals can be immunized by injection with MAP2 kinase protein, or fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and, *Corynebacterium parvum*.

A molecular clone of an antibody to a MAP2 kinase epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

The present invention provides for antibody molecules as well as fragments of such antibody molecules.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

5.5. Bioassays for MAP2 Kinase Activity

The activity of MAP2 kinase may be measured using any suitable kinase assay known in the art. For example, and not by way of limitation, the method described in (Boulton et al., 1990, J. Biol. Chem. 265:2713–2719) as follows. The assay for phosphorylation of MAP2 may contain 30 mM Hepes, pH 8, 50 µM ATP (1–50 cpm/fmol), 1 mM dithiothreitol, 1 mM benzamidine, 10 mM $MgCl_2$, 100 µg/ml bovine serum albumin, 3 µg MAP2 and no more than about 10 µg sample protein in a final volume of 30 µl for 10 minutes at 30° C. The amount of MAP2 in the assay (100 µg/ml) may be chosen for convenience of analysis both by SDS-PAGE and by precipitation. The enzyme is not saturated with substrate even at 1.36 mg MAP2/ml. However, with 100 µg MAP2/ml enzyme activity may be expected to be linear with time for at least 30 minutes. All samples except for unfractionated supernatants may be routinely assayed as above in the presence of 1 mg of bovine serum albumin. Assays may be terminated by the addition of 10% trichloroacetic acid and precipitates may be collected on glass fiber filters. All assays except as noted above may be terminated by the addition of 0.25 volume of 0.3 M Tris-HCl, pH 6.9, containing 2 M mercaptoethanol, 50% glycerol and 10% SDS and analyzed by electrophoresis in SDS using 5% (MAP2) polyacrylamide gels. The gels may be stained with Coomassie blue, destained in 10% methanol and 10% acetic acid, dried and subjected to autoradiography at −80° C. using Kodak XS-5 or BB-5 film with Dupont Quanta III intensifying screens. Substrate bands may be excised from gels and $^{32}P$ may be quantitated using liquid scintillation counting.

5.6. Utility of the Invention

The present invention may be utilized to provide unique model systems for the study of mechanisms of hormones and other cellular factors, and may also be used in methods for screening compounds for hormone/cellular factor activity and to identify agents which function as agonists or antagonists.

According to various embodiments of the invention, recombinant MAP2 kinase molecules can be used to create novel model systems for the study of mechanisms of hormones and other cellular factors. For example, and not by way of limitation, the recombinant molecules of the invention can be incorporated into cells or organisms such that higher than normal amounts of MAP2 kinase are produced, so that the effects of hyperactivation of MAP2 kinase may be evaluated. Overproduction of MAP2 kinase may identify aspects of the hormonal/cellular factor response related to MAP2 kinase activity, particularly when evaluated in comparison to cells or organisms which produce normal amounts of MAP2 kinase.

Alternatively, recombinant MAP2 kinase molecules may be engineered such that cells or organisms comprising the recombination molecules produce a mutant form of MAP2 kinase which may, for example, lack the serine/threonine kinase activity of normal MAP2 kinase. The mutant kinase may, on a concentration basis, overshadow, or titrate out, the effects of normal MAP2 kinase and thereby create cells or organisms with a functional aberrancy of MAP2 kinase function. It is also envisioned that such mutant nucleic acid sequences may result in mutation of the endogenous MAP2 kinase gene, for example, by homologous recombination, creating true MAP2 kinase mutants. In light of the high levels of expression of MAP2 kinase encoding mRNA in the central nervous system, and the role of MAP2 in forming neurofibrillary tangles, it may be possible to generate a transgenic non-human animal which expresses a mutant MAP2 kinase molecule in its central nervous system (e.g. via a brain-specific promoter sequence) and which may serve as an animal model system for neurological disorders such as Alzheimer's disease or for peripheral neuropathies.

In addition, because the present invention enables the production of large amounts of purified MAP2 kinase for the first time, it allows for the production of anti-MAP2 kinase antibodies. Anti-MAP2 kinase antibodies, polyclonal or monoclonal, may be used in experiments utilizing cells or organisms which study the effects of selective neutralization of MAP2 kinase function. Such experiments may further elucidate the specific role of MAP2 kinase in hormone or cellular factor action.

An important embodiment of the present invention relates to methods for the screening of compounds for hormone or cellular factor activity. In specific embodiments, the present invention provides for a method of detecting the presence of a compound having nerve growth factor-like activity comprising (i) culturing cells that produce an NAP2 protein kinase (which is activated by nerve growth factor) in the presence of a compound suspected of having nerve growth factor-like activity (construed to mean activity similar but not necessarily identical to NGF, including, for example, the ability to support the growth of sympathetic neurons in culture) and (ii) detecting changes in the levels of MAP2 protein kinase activity, wherein an increase in activity is indicative of the presence of nerve growth factor-like activity. Similarly, in another specific embodiment, the present invention provides for a method of detecting the presence of a compound having insulin-like activity comprising (i) culturing cells that produce an MAP2 protein kinase (which is activated by insulin) in the presence of a compound suspected of having insulin-like activity (construed to mean activity similar but not necessarily identical to insulin, including for example, the ability to activate MAP2 kinase in insulin, responsive cells) and (ii) detecting changes in the levels of MAP2 protein kinase activity, wherein an increase in activity is indicative of the presence of insulin-like activity. The present invention therefore provides a powerful method for identifying compounds that may be useful in the treatment of diabetes. The present invention also provides for analogous methods which screen for the activity of other hormones or cellular factors. In additional embodiments of the invention, it may be desirable, in the above-mentioned screening methods, to utilize cell lines which comprises a recombinant nucleic acid molecule encoding a mammalian MAP2 kinase, including, but not limited to, recombinant nucleic acid molecules comprising sequences substantially as depicted in FIGS. 2B (SEQ ID NO:1), 3A (SEQ ID NO:3) and 3B (SEQ ID NO:5). Such cell lines may preferably express elevated levels of MAP2 kinase, and would therefore provide a more sensitive assay for MAP2 kinase activation. The present invention also provides for similar methods, in which cells utilized for screening comprise a recombinant nucleic acid sequence homologous to the sequence substantially as depicted in FIGS. 2B (SEQ ID NO:1), 3A (SEQ ID NO:3) and 3B (SEQ ID NO:5) or a portion thereof. The methods of the invention may be used to identify compounds that may be effective in the treatment of peripheral neuropathies or which may promote nerve regeneration. Furthermore, because NGF-responsive cholinergic neurons of the basal forebrain nucleic are consistently affected in early stages of Alzheimer's disease, the methods of the present invention may be particularly useful in identifying compounds with NGF-like activity which may be effective in the treatment of Alzheimer's disease. In addition, such methods may enable the identification of molecules capable of bypassing the hormone/receptor interaction. It may be clinically useful to inhibit the activity of MAP2 kinase in an organism, using, for example, small molecules such as purine analogues.

In further embodiments of the present invention, recombinant MAP2 kinase may be used to identify other molecules, such as kinases related to cellular factor or hormone action. For example, recombinant MAP2 kinase could be used to identify additional kinases by affinity purification, wherein a MAP2 kinase may be used to adhere to other kinases which participate in a MAP2 associated phosphorylation cascade. Sequenced portions of the NGF receptor are likely to be physically associated with an as yet unidentified protein kinase. Recombinant MAP2 kinase may be useful in studying such interactions.

In another embodiment, detecting a change in a MAP2 protein kinase activity resulting from culturing cells in the presence of a compound known to or suspected to affect MAP2 protein kinase activity, can be used to detect the presence or measure the amount of such a compound and its ability to modulate MAP2 kinase activity levels. Such an effect on MAP2 kinase activity can occur directly or indirectly (e.g. through a signal transduction pathway). In a specific example of such an embodiment, the presence of a neurotrophin molecule (including but not limited to NGF, brain derived neurotrophic factor, neurotrophin-3 (NT-3) and other members of the NGF/BDNF/NT-3 family of molecules) can be detected by detecting an increase in the activity of a MAP2 protein kinase upon culturing the cells in the presence of a sample suspected of containing such a neurotrophin molecule. The cells which are cultured in such assays should express receptors for the neurotrophin molecule being detected, which receptors can be endogenous or recombinant.

6. EXAMPLE

Molecular Cloning of an Insulin-stimulated MAP2 Protein Kinase: Homology in Pheromone-regulated Cell Cycle Control

6.1. Materials and Methods

6.1.1. Cell Lines

Rat 1 HIRc B cells (McClain et al., 1987, J. Biol. Chem. 262:14663–14671) were obtained from Don McClain (Veterans Administration Medical Center, San Diego, Calif.). Porcine insulin was a gift from Mary Root (Eli Lilly). Restriction enzymes were obtained from New England Biolabs.

6.1.2. Purification and Sequencing of Tryptic Peptides from MAP2 Kinase

MAP2 kinase was purified from insulin-treated Rat 1 HIRc B cells (Boulton et al., 1990, Biochem. 30:278–286), digested with trypsin and the resulting peptides subjected to HPLC (Abersold et al., 1987, Proc. Natl. Acad. U.S.A. 84:6970–6974). The peptides from one of the resulting peaks were subjected to a second chromatographic separation. Amino acid sequence was obtained from seven distinct peaks. One peak contained a mixture of three peptides, with one major and two minor components: the sequence of the major peptide was determined based on recovery, but the assignment of the amino acids in the minor components to their respective peptide sequences was based on the cDNA sequence (see below).

6.1.3. Cloning an Amplified Fragment of the MAP2 Kinase cDNA

A series of degenerate oligonucleotides were synthesized that corresponded to the coding or anti-coding strands for fragments of the tryptic peptide sequences obtained. The oligonucleotides contained non-degenerate tails at their 5' ends; the tail of each coding strand oligonucleotide had an EcoR1 restriction site, while the tail of each anti-coding strand oligonucleotide contained a Sall restriction site. Each coding strand oligonucleotide was combined with each anti-coding oligonucleotide in individual PCR reactions using rat genomic DNA or cDNA from Rat 1 cells as template; the PCR reactions and the preparation of the genomic and cDNA templates were performed as described in Maisonpierre et al. (1990, Science 247:1446–1451) and Yancopoulous and Alt (1990, in "Methods for Cloning and Analysis of Eukaryotic Genes", Jones and Bartlett, Boston, Mass.). The amplified product obtained using the QYIGEG SEQ ID NO:7 coding oligonucleotide and the DLKPSN SEQ ID NO:9 anti-coding oligonucleotide (designated QYDL SEQ ID NO:11) was isolated using a Sephadex G-50 spin column, digested with EcoR1 and Sall, gel purified using 2% Nusieve (FMC Bioproducts), and subcloned into the pGEM4Z vector. (Promega).

6.1.4. Screening the cDNA Library 600,000 plaques from a rat brain cDNA library constructed in the Lambda Zap 2 vector (Stratagene) were screened using the subcloned QYDL PCR product as probe; the prove was radiolabeled using a PCR-based protocol described in Maisonpierre et al. Hybridization conditions have been described in Maisonpierre et al.; after hybridization the library filters were first washed at low stringency (2×SSC, 0.1% SDS at 60° C.) and then at high stringency (0.2×SSC, 0.1% SDS at 68° C.).

6.1.5. DNA Sequencing

Sequencing was performed using the dideoxynucleotide chain termination method (Sanger et al., 1977, Proc. Natl. Acad. Sci. U.S.A. 74:5463–5467), with the Sequenase Kit (version 2.0) and recommended protocols (U.S. Biochemical). All sequence was verified by sequencing both strands of the DNA, using appropriate oligonucleotides corresponding to MAP2 kinase sequence or flanking plasmid sequence.

6.1.6. Northern Analysis

RNA isolation, Northern blotting, and hybridization to labeled probes were performed as described in Maisonpierre et al. (1990; Science 247:1446–1451).

6.2. Results

Purified MAP2 kinase isolated from insulin-treated rat 1 HIRc B cells consists of one major band of $M_r$=43,000. SDS polyacrylamide gel electrophoresis of final Q Sepharose #2 fractions isolated from NGF-treated or control PC12 cells indicated that purification of MAP2 kinase from PC12 cells appears to parallel purification of MAP2 kinases from insulin treated rat HIRC B cells (FIG. 2A). Following tryptic cleavage, amino acid sequences of seven tryptic peptides were obtained from the 43 kd band; these peptides are underlined in FIG. 2. None of the peptides are contained in proteins in the Genbank data base. However, consensus sequences characteristic of serine/threonine protein kinases (Hanks et al., 1988, Science 241:42–52), GEGAYG SEQ ID NO:12 (part of the nucleotide binding site) and DLKPSN SEQ ID NO:9 were found among the tryptic peptides isolated from this protein.

Degenerate oligonucleotides corresponding to several different regions of the resulting amino acid sequence were utilized in PCR reactions. Oligonucleotides corresponding to segments of the peptides containing the conserved GEGAYG (SEQ ID NO:12) and DLKPSN SEQ ID NO:9 sequences to segments most clearly yielded amplified fragments of an expected size using cDNA templates prepared from Rat 1 fibroblasts. Based on homologies to other protein kinases it was assumed that the GEGAYG SEQ ID NO:12 sequence is closer to the N-terminus of the protein and DLKPSN SEQ ID NO:9 is closer to the C-terminus of the protein; these sequences are separated by about 120 amino acids in most protein kinases. PCR reactions using the degenerate oligonucleotide encoding the amino acids QYIGEG (SEQ ID No:7) (5'-TTCTAGAATTCCA(A,G)TA(C,T)AT(A,T,C)GG(A,T,C,G)GA(A,G) GG-3', SEQ ID NO:8) and the degenerate oligonucleotide corresponding to the anti-coding strand for the amino acids DLKPSN (SEQ ID NO:9) (t5'-TTCTCGAGTCGAC(A,G)TT(A,T,C,G)GA(A,T,C,G) GG(C,T)TT(A,T,C,G)A(A,G)A,G)TC-3', SEQ ID NO:10) yielded an amplified product of approximately 360 bp. The PCR product was subcloned and sequenced to confirm its identity as a novel protein kinase. The PCR product was then used as a probe to screen a rat brain cDNA library. A single clone that hybridizes at high stringency has been isolated; this clone contains a 1.9 kb cDNA insert. Northern blot analysis revealed a band corresponding to a mRNA of 1.9 kb, indicating that the insert corresponded to a full-length clone.

The cDNA insert has a single long open reading frame that could encode a protein of at least 367 residues with $M_r$ greater than or equal to 42,000; it contains the primary sequence of seven of the tryptic peptides isolated from the insulin-stimulated MAP2 kinase. In addition, the exact sequences of two additional peptides from a mixed sequence are found in the translated cDNA. Together these tryptic peptides consisted of 115 residues all of which are in accord with sequence in the translated cDNA, accounting for over 31% of the putative translation product. The exact correspondence between the extensive tryptic peptide sequence and the predicted translation product provides substantial evidence that the cDNA encodes the insulin-stimulated MAP2 kinase. We have designated the gene ERK1 for extracellular signal-regulated kinase-1.

ERK1 contains the 15 invariant residues found in all protein kinases; it also displays substantial homology with all of the subdomains defined by Hanks et al. (1988, Science, 241:42–52), and contains residues characteristic of serine/threonine protein kinases. A comparison with other protein kinases reveals striking similarities between MAP2 kinase and the KSS1 (Courchesne, et al., 1989, Cell 58:1107–1119) and FUS3 (Elion, et al., Cell 60:649–664) protein kinases recently isolated from yeast. See infra and FIG. 4. ERK1 kinase is 56% identical to KSS1, and 56% identical to FUS3. KSS1 and FUS3 display about the same degree of similarity (57%) to each other as they do to MAP2 kinase; they are all significantly less homologous to other kinases than they are to each other. All three share their next most impressive homologies with the $CDC28/cdc^{2+}$ subfamily of kinases (ERK1 kinase is 41% identical to this kinase). However, KSS1, FUS3 and MAP2 kinase all lack the VPSTAIR SEQ ID NO:13 sequence found in subdomain III of all CDC28 functional homologs. Furthermore, all three also share C-terminal extensions not found on the $CDC28/cdc^{2+}$ kinases. Unlike FUS3 and KSS1, MAP2 kinase contains a significant N-terminal extension of at least 17 amino acids.

ERK1 also differs from its yeast homologs at the C-terminus and between the DFG and APE motifs of subdomains VII and VIII, which contain inserts of different lengths with phosphorylatable residues (e.g. Thr-238 and Thr-242 in ERK1). Both regions poorly conserved between the yeast kinases, have been implicated in determining unique functional characteristics of individual kinases. In a number of kinases the segment that resides between subdomains VII and VIII is autophosphorylated in a manner that influences enzymatic activity (e.g., cAMP-dependent protein kinases insulin receptor). Conservation among the kinases may also reveal functionally important residues. There is a conserved tyrosine in subdomain 1, whose phosphorylation in CDC28 is known to inhibit protein kinase activity. Near the C-terminus of the protein is a sequence (residues 367–379) that draws particular attention as a potential site of tyrosine phosphorylation due to interesting similarities to the regulatory autophosphorylated region of the insulin receptor. Three tyrosine residues are located within this region spaced identically to those in the receptor ($YX_3YY$); four acidic residues, important determinants for recognition by protein-tyrosine kinases, are nearby. The presence of sequences resembling the insulin receptor phosphorylation site is consistent with evidence suggesting that ERK1 (MAP2 kinase) may be a substrate for the insulin receptor.

6.2.1. Tissue Distribution and Inducibility of the MAP2 Kinase Transcript

A probe made from the MAP2 kinase cDNA identifies a single 1.9. kb transcript on Northern blot analysis, indicating that our cDNA clone represents nearly full-length transcript. The MAP2 kinase transcript is detectable in all tissues and cell lines examined.

Interestingly, the transcript is expressed at highest levels (by 3- to 6-fold) in the central nervous system compared to other tissues examined. The abundance of MAP2 kinase transcripts in the adult rat brain was estimated to be about 0.0005% by screening $10^6$ phage from a rat brain cDNA library at high stringency. The transcript is clearly detectable in Rat 1 fibroblasts and PC12 cell lines, both of which express acutely activatable MAP2 kinase.

6.3. Discussion

Amino acid sequence was obtained from tryptic peptides isolated from a MAP2 protein kinase purified over 6000-fold from insulin-stimulated rat fibroblasts. The sequence was used to design degenerate oligonucleotides that led to the molecular cloning of a 1.9 kb cDNA via a PCR-based strategy. The cDNA predicts a protein with a molecular weight of greater than or equal to 42,000, designated ERK1, which contains sequences consistent with all of the tryptic peptide sequence obtained from the purified MAP2 kinase, accounting for more than 31% of the primary sequence of the protein. Thus, this cDNA appears to encode the insulin-stimulated MAP2 kinase.

Many protein kinases phosphorylate MAP2 (Aklyama et al., 1986, J. Biol. Chem. 261:14797–14803; Akiyama et al., 1986, J. Biol. Chem. 261:15648–15651; Hernandez et al., 1987, J. Neurochem. 48:84–93). The MAP2 kinase molecularly cloned here is distinguished by its rapid activation by insulin (Boulton et al., 1990, J. Biol. Chem. 265:2713–2719; Ray et al., 1987, Proc. Natl. Acad. Sci. U.S.A. 84:1502–1506; Ray et al., 1988, Proc. Natl. Acad. Sci. U.S.A. 85:3753–3757; Ray et al., 1988, J. Biol. Chem. 263:12721–12727; Hoshi et al., 1988, J. Biol. Chem. 263:5396–5401; Sturgill et al., 1988, Nature, 334:715–718; Anderson et al., 1990, Nature 343:651–653). Although the physiological functions of this enzyme are not known, a role in the regulation of S6 phosphorylation was proposed following the demonstration that MAP2 kinase phosphorylates and activates S6 kinase II purified from *Xenopus laevis* (Sturgill et al., 1988, Nature 334:715–718) as well as a rabbit liver S6 kinase (Gregory et al., 1989, J. Biol. Chem. 264:18397–18401). The involvement of the MAP2 kinase in signaling pathways is further indicated by the presence of phosphotyrosine on the kinase (Ray et al., 1988, Proc. Natl. Acad. Sci. U.S.A. 85:3753–3757; Boulton et al., 1991, Biochem. 30:278–286; Boulton et al., May 1991, Cell). While it has not been shown that the insulin receptor catalyzes this phosphorylation, the fact that dephosphorylation of the tyrosine residues decreases activity (Anderson et al., 1990, Nature 343:651–653; Boulton and Cobb, May 1991, in Cell Regulation, Vol. II) supports the notion that the MAP2 kinase functions at an early step in the signal transduction pathway and is, therefore, perhaps directly regulated by the insulin receptor. Additional evidence indicating a role for this kinase in signaling by numerous agents is raised by evidence indicating that the MAP2 kinase may be pp42 (Rossomando et al., 1989, Proc. Natl. Acad. Sci. U.S.A. 86:6940–6943), a protein whose phosphotyrosine content increases following transformation by viruses and exposure to growth factors (Cooper et al., 1981, Mol. Cell. Biol. 1:165–178). MAP2 kinase, or a closely related enzyme is also activated by a variety of agents that promote differentiation or expression of differentiated functions, not cellular proliferation (Boulton et al., 1990, J. Biol. Chem. 265:2713–2719; Ray et al., 1987, Proc. Natl. Acad. Sci. U.S.A. 84:1502–1506; Ray et al., 1988, Proc. Nat. Acad. Sci. U.S.A. 85:3753–3757; Ray et al., 1988, J. Biol. Chem. 263:12721–12727; Hoshi et al., 1988, J. Biol. Chem. 263:5396–5401; Ely et al., 1990, J. Cell Biol. 110:731–742; Volonte et al., 1989, J. Cell Biol. 109:2395–2403; Miyasaka et al., 1990, J. Biol. Chem. 265:4730–4735) For example, we have recently purified a nerve growth factor-stimulated MAP2 kinase from PC12 cells to near homogeneity by the same procedure developed to purify the insulin-stimulated enzyme. This enzyme is the same size by SDS-PAGE as the insulin-stimulated kinase. Furthermore, the activity has properties in common with nerve growth factor-activated MAP kinase described by Greene and coworkers (Volonte et al., 1989, J. Cell Biol. 109:2395–2403 and Miyasaka et al., 1990, J. Biol. Chem. 265:4730–4735.

The dramatic homology between ERK1 and the two yeast kinases, KSS1 and FUS3, is consistent with a critical and evolutionarily conserved role for this new family of kinases in mediating the response to extracellular signals. The yeast kinases play antagonistic roles in regulating the yeast cell cycle in response to mating factors, the only known peptide hormones that mediate intercellular communication in yeast. Both kinases seem to act by fine-tuning the activity of CDC28, a related protein-serine/threonine kinase which is the indispensable regulator of the mitotic cycle, probably via interactions with a yeast cyclin. FUS3 apparently has two regulatory roles. It seems to be important in leading to pheromone-induced cell-cycle arrest in G1, either by directly inhibiting the activation of CDC28 or by promoting the inactivation of a cyclin required for CDC28 activation; activation of FUS3 by pheromones also independently promotes mating-specific functions. By contrast, KSS1 promotes re-entry into the cell cycle following pheromone-induced cell-cycle arrest; KSS1 may work by activating the same cyclin that FUS3 may inactivate. ERK1 apparently represents a mammalian counterpart, perhaps functionally as well as evolutionarily, to the yeast kinases. Thus ERK1 may act via similar pathways to regulate the cell cycle in response to a variety of extracellular signals. As with FUS3, ERK1 apparently also plays a regulatory role in responses that do not directly involve the cell cycle. The dramatic homology between ERK1 and the yeast kinases raises the possibility that yeast may provide a useful experimental system in which to introduce ERK1 for the analysis of its function.

MAP2 kinase, or MAP2 kinase-like activity, is increased in many different types of cells in response to a wide variety of stimuli. In the course of cloning ERK1, we have also molecularly cloned other closely related kinases. The identification of a mammalian family of MAP2 kinase-related enzymes, which are structural homologs of the yeast KSS1 and FUS3 kinases, suggests that multicellular, higher eucaryotes have appropriated kinases, originally utilized to detect environmental perturbation by unicellular organisms, to mediate responses to extracellular signals. The molecular cloning of this family of MAP kinase-related proteins will facilitate the elucidation of the mechanisms of regulation of this group of enzymes and studies of their physiological roles.

7. EXAMPLE

Erks, a Family of Protein-serine/-Threonine Kinase that are Activated and Tyrosine Phosphorylated in Response to Insulin and NGF

7.1. Materials and Methods

7.1.1. Isolation and Sequences Analysis of Novel ERK Genes

The QYDL probe described in Boulton et al. (1990, Science 249:64–67) was used to screen both a rat brain cDNA library constructed in the Lambda Zap II vector (Stratagene) as well as a rat genomic DNA library derived from rat (Sprague-Dawley) liver DNA partially digested with Sau3A restriction endonuclease and then cloned into the EMBL3/SP6/T7 bacteriophage vector (Clontech). After hybridization (Maisonpierre et al., 1990a, Science 247:1446–1451), the ERK2 and ERK3 phage clones were identified (and eventually purified) by washing library filters using low-normal stringency (20 mM sodium citrate, pH 7.0, 0.15 N NaCl, 0.1% sodium dodecyl sulfate (SDS) at 60° C.). The inserts in the phage clones were subcloned into Bluescript2 plasmid (Stratagene), and characterized by DNA sequence analysis using the dideoxynucleotide chain termination method (Sanger et al., 1977, Proc. Natl. Acad. Sci. U.S.A. 74:5463–6467), with the Sequenase version 2.0 kit and recommended protocols (U.S. Biochemical).

7.1.2. Generation of ERK-specific Probes

Oligonucleotides (17 bases) corresponding to the DNA sequences bordering the relatively unconserved N-terminal regions of ERK1 (amino acids 5–67), ERK2 (amino acids 14–138), and ERK3 (amino acids 11–105), were used to amplify precisely these coding regions from plasmids containing each of the ERK-cDNA inserts. The N-terminal coding regions were used because they were the least homologous regions among these three ERKs. Polymerase chain reaction (PCR) amplifications were also performed, with each pair of these primers, using either rat brain cDNA or genomic rat DNA as template. Each of these amplifications yielded indistinguishable fragments whether genomic DNA or cDNA was used, indicating that these probes did not span any introns within the ERK genes. The three fragments amplified from plasmids were each radiolabeled using the polymerase chain reaction method and hybridized to Southern blots containing rat and human genomic DNA (as described in Maisonpierre et al., 1990, Science 247:1446–1451); the filters were hybridized to each of the radiolabeled ERK-specific probes at 68° C. in the presence of 0.5 M sodium phosphate, pH 7.0, 1% bovine serum albumin (fraction V, Sigma), 7% SDS, 1 mM EDTA (Mahmoudi and Lin, 1989, Biotechniques 7:331–333) and 100 $\mu$g/ml of sonicated, denatured salmon sperm DNA, and then were washed at 68° C. as in Maisonpierre et al. (1990, Science 247:1446–1451) and subjected to autoradiography.

7.1.3. Northern Blot Analysis

Dissections of tissues and brain regions of Sprague-Dawley rats (Harlan Sprague Dawley, Inc.) were performed as described in Maisonpierre et al., 1990, Neuron 5:501–509. The dissected samples were immediately frozen in liquid nitrogen. Timed-pregnant rats were used to obtain embryonic tissues, with day of sperm positivity designated as day E1; the day of birth was designated PO. Adult rats averaged 150–275 g (6–8 weeks of age). Total RNAs were isolated by homogenization in 3M LiCl/6M urea as described in Bothwell et al., 1990, "Preparation of DNA and RNA. In Methods For Cloning and Analysis of Eukaryotic Genes", Jones and Bartlett, Boston, Mass., pp. 15–16. Gel electrophoresis, capillary transfer to nylon membranes (MagnaGraph, Micro Separations, Inc.), and UV-cross-linking to the membranes were performed as described in Maisonpierre et al., 1990, Neuron 5:501–509. The filters were hybridized to the radiolabeled ERK-specific probes and washed as described in the preceding section. Ethidium bromide staining of triplicate gels demonstrated that equivalent amounts of total RNA were being assayed (Maisonpierre et al., 1990, Science 247:1446–1451) on each blot; this was confirmed by hybridizing several of the blots with a probe for 28S rRNA.

7.1.4. Culturing of Astro-glial Cells and P19 Embryocarcinomas

To obtain purified astroglial cell hippocampi from newborn rats were dissected, dissociated and cultured in serum-containing medium (DMEM supplemented with 10% fetal bovine serum). On culture days 7 and 9, the flasks were shaken vigorously to remove non-astroglial cells. Astroglia were then plated onto 100 mm dishes and cultured for 28 days prior to RNA preparation. The S1801A1 subclone of the P19 embryocarcinoma (McBurney et al., 1982, Nature 2999:165–167) was cultured and induced as described in Dinsmore and Solomon, 1991, Cell 64:817–826. RNA was prepared 3 days after induction.

7.1.5. Bacterial Strians and Plasmids

*E. coli* W3110 lac 1$^q$F$^-$ a strain that overproduces the lactose operon repressor, and the plasmid vector pCP110 have been used in studies described in Panayotatos, 1988, Gene 74:357–363. Vectors were engineered for ERK2 expression by using polymerase chain reaction as follows: The 5' synthetic oligodeoxyribonucleotide primer (RAE-21) was designed to generate a unique Sal I site immediately following the initiation methionine ATG codon by changing the sequence GTA-CGA(Val-Arg) into TCG-ACA(Ser-Thr). The 3' primer (RAE22) included a unique Eag I site following the TAA termination codon. The expression vector pCP110 was linearized with Sal I plus Eag I and the resulting 3652 bp fragment was purified by agarose gel electrophoresis. The vector and PCR fragment similarly digested and purified were ligated and transformed in *E. coli* W3110 lac 1$^q$F$^-$. Transformants were screened by restriction mapping for the desired plasmid and a positive candidate (pRPN117) was confirmed by DNA sequencing to carry the expected full length gene fused to the translation initiation signal in the correct reading frame.

pRPN125: This plasmid is identical to pRPN117 except that the codons of the first two amino acids were restored to the native sequence. This was accomplished with two internal PCR primers that extended over the target sequence and carried the desired modifications and two external primers that served to amplify the desired fragment. Two reactions, each with 1 $\mu$g pRPN117 as a template, were set up: one contained 5 $\mu$g RAE-10 primer and 0.5 $\mu$g RAE-28 primer and the other 5 $\mu$g RAE-22 primer and 0.5 $\mu$g RAE-27 primer. After ten PCR cycles (each cycle consisting of incubation for 1 min at 92° C., 2 min at 55° C., 2 min at 72° C.) the two samples were combined and subjected to another 25 cycles (consisting of incubation for 1 min at 94° C., 2 min at 55° C., 4 min at 74° C.) in the DNA thermal cycler. Because the internal primers RAE-28 and RAE-27 are fully complementary to each other, the products of the first stage PCR reactions can subsequently anneal. Furthermore, in the second stage reaction, the presence of substantially higher concentrations of the external primers RAE-10 and RAE-22 drives the synthesis of large amounts of the desired full-length product. The product of the final PCR reaction was purified by PAGE. A 3349 bp fragment was obtained by digesting pRPN117 with Aat II and Eag I and purified by agarose gel electrophoresis. Both fragments were ligated and transformed in *E. coli* W3110 lac 1$^q$F$^-$. Transformants were screened by restriction mapping for the desired plasmid and one of the positive candidates (pRPN125) was further characterized by DNA sequencing across the 5' primer region.

For fermentation, cells were shaken in LB broth at 37° C. to $OD_{590}$=1. Lactose was added to 1% final concentration and incubation continued for 20 hours. Cells were collected by centrifugation at 6,000×g for 30 min, resuspended in threefold (w/v) excess buffer A (100 mM Tris-HCl pH 7.5, 50 mM EDTA pH 8.0, 0.2 mM DTT) and stored at −20° C.

7.1.6. Purification of Recombinant ERK2

Cells (2 g) were thawed at room temperature, incubated with 2 mg of lysozyme on ice for 20 minutes and passed through a French press (SLM-Aminco) at 8000 psi. The viscous suspension was then diluted 2-fold with buffer A and further homogenized with 3 1-minute bursts of a Polytron (Kinematica) at a setting of 4. After centrifugation at 11,000×g for 10 minutes at 4° C., the supernatant was diluted 5-fold with buffer B (20 mM Hepes, pH 7.5, 0.1 mM EDTA, 2 mM dithiothreitol, and 20 mM NaCl) and applied to Affigel blue (Biorad) equilibrated in buffer B. Proteins were eluted with a 100-ml, linear gradient of 0.02–1 M NaCl in buffer B. Fractions of ERK2 (0.4–1 M NaCl) were diluted with buffer C (20 mM histidine, pH 5.6, 0.1 mM EDTA, 2 mM dithiothreitol, and 20 mM NaCl) to reduce NaCl to 0.1 M and loaded onto a DEAE-cellulose cartridge (ZetaPrep 60, CUNO) equilibrated in buffer C. The cartridge was washed stepwise with 0.1–1 M NaCl in 0.1 M increments. ERK2 eluted between 0.6 and 0.9 M NaCl and was judged to be greater than 90% pure (e.g. FIG. 7C).

7.1.7. Measurement of Recombinant ERK2 Activity

Autophosphorylation of ERK2 was carried out in the presence of 10 mM $MgCl_2$, 1 mM dithiothreitol, 1 mM benzamidine, 30 mM Hepes, pH 8.0, and [$\gamma$-$^{32}$P]ATP at 30° C. for 30 minutes. Kinase activity was measured by incubating ERK2 with 50 $\mu$M ATP, 20 mM $MgCl_2$, 1 mM dithiothreitol, 1 mM benzamidine and MBP or MAP2(0.1 mg/ml). The reactions were terminated with 10% trichloroacetic acid as in Boulton et al., 1991, Biochemistry 30:278–286.

7.1.8. Labeling, Immunoprecipitation, and Phosphoamino Acid Analysis of ERK1

Rat 1 HIRc B or PC12 cells in 2 100-mm dishes were changed to serum-free Krebs-Ringers-bicarbonate solution in 2% bovine serum albumin (Smith et al., 1980, Proc. Natl. Acad. Sci. U.S.A., 77:2641–2645) for either overnight or 60 minutes and then labeled with $^{32}$P orthophosphoric acid (1 mCi/ml) for 50 minutes with or without the addition of insulin (0.18 $\mu$M) or NGF (75 ng/ml) for the last 5 minutes of the incubation. The cells were washed in chilled medium, scraped in 1 ml of homogenization buffer (20 mM p-nitrophenylphosphate, 20 mM Tris-HCl, pH 7.5, 1 mM EGTA, 50 mM sodium fluoride, 50 $\mu$M sodium orthovanadate and 5 mM benzamidine) containing 2 mM phenylmethylsulfonyl fluoride and 0.1 $\mu$M pepstatin, and homogenized by douncing. Following sedimentation at 100,000×g for 1 hour at 4° C., the supernatants (1 ml) were precleared once with preimmune serum and then divided for incubation with 5 $\mu$l of either antiserum 837 or preimmune serum for 1 hour on ice. Immune complexes were collected with Pan-sorbin (Calbiochem) and washed in homogenization buffer plus 0.2% Triton X-100 containing first 2 M NaCl, second 0.15 M NaCl, and finally 0.15 M NaCl plus 0.01% SDS. The pellets were resuspended in 40 $\mu$l of 2.5-fold concentrated electrophoresis sample buffer, boiled for 10 minutes, and loaded onto a 10% polyacrylamide gel in SDS. Aliquots (5 $\mu$l) along with an ERK1 standard were transferred to nitrocellulose to confirm by immunoblotting that the radiolabeled band in each immunoprecipitate comigrated with ERK1. For denaturing immunoprecipitations, the supernatants were adjusted to final concentrations of 0.5% SDS and 1 mM dithiothreitol. The samples were boiled 1–2 minutes and diluted 4-fold with homogenization buffer containing 1.25% sodium deoxycholate, 1.25% Triton X-100, and 0.1 or 1 mM dithiothreitol and then immunoprecipitated as above. The bands corresponding to ERK1 were excised from the dried gels and hydrolyzed in 6 N HCl for 90 minutes. Phospho-amino acids were analyzed as described by Cooper et al., 1983, "Methods In Enzymology,", Vol. 99, J. D. Corbin and J. G. Hardman, eds, New York Academic Press, pp. 387–402.

To blot the immune complexes 1 mg of supernatant was immunoprecipitated under denaturing conditions. The Pan-sorbin pellets were washed twice with 0.25 M Tris, pH 7.5, and 0.1 M NaCl prior to electrophoresis. To detect phosphotyrosine the blot was stained using a monoclonal antibody to phosphotyrosine (UBI) and visualized with a goat anti-mouse IgG alkaline phosphatase-conjugated secondary antibody. The 691 immunoblot was developed with goat anti-rabbit IgG horse radish peroxidase-conjugated secondary antibody.

7.1.9. Chromatography of Extracts on Mono-Q Sepharose

PC12 cells were grown to confluence on uncoated plastic dishes in Dulbecco's Modified Eagles medium with 5% fetal bovine serum and 5% horse serum. NGF was added to 5 of 10 150-mm dishes at a final concentration of 50 ng/ml for 5 minutes. Cells were scraped into homogenization buffer and soluble fractions were prepared and protein determined as described (Boulton et al., 1991, Biochem. 30:278–286). Soluble fractions were diluted with 3 volumes of water and applied to a Mono-Q HR 5/5 column equilibrated in 50 mM $\beta$-glycerophosphate, pH 7.3, 1 mM EGTA, 1 mM dithiothreitol, 0.1 mM sodium vanadate, and 0.1 $\mu$M pepstatin. The protein was eluted with a gradient of 0–0.3 M NaCl in this buffer. Sixty 1-ml fractions were collected and assayed for MBP kinase activity using 0.3 mg/ml MBP.

7.2. Results

7.2.1. Molecular Cloning of Two Novels ERKs

Figure 3A-1:
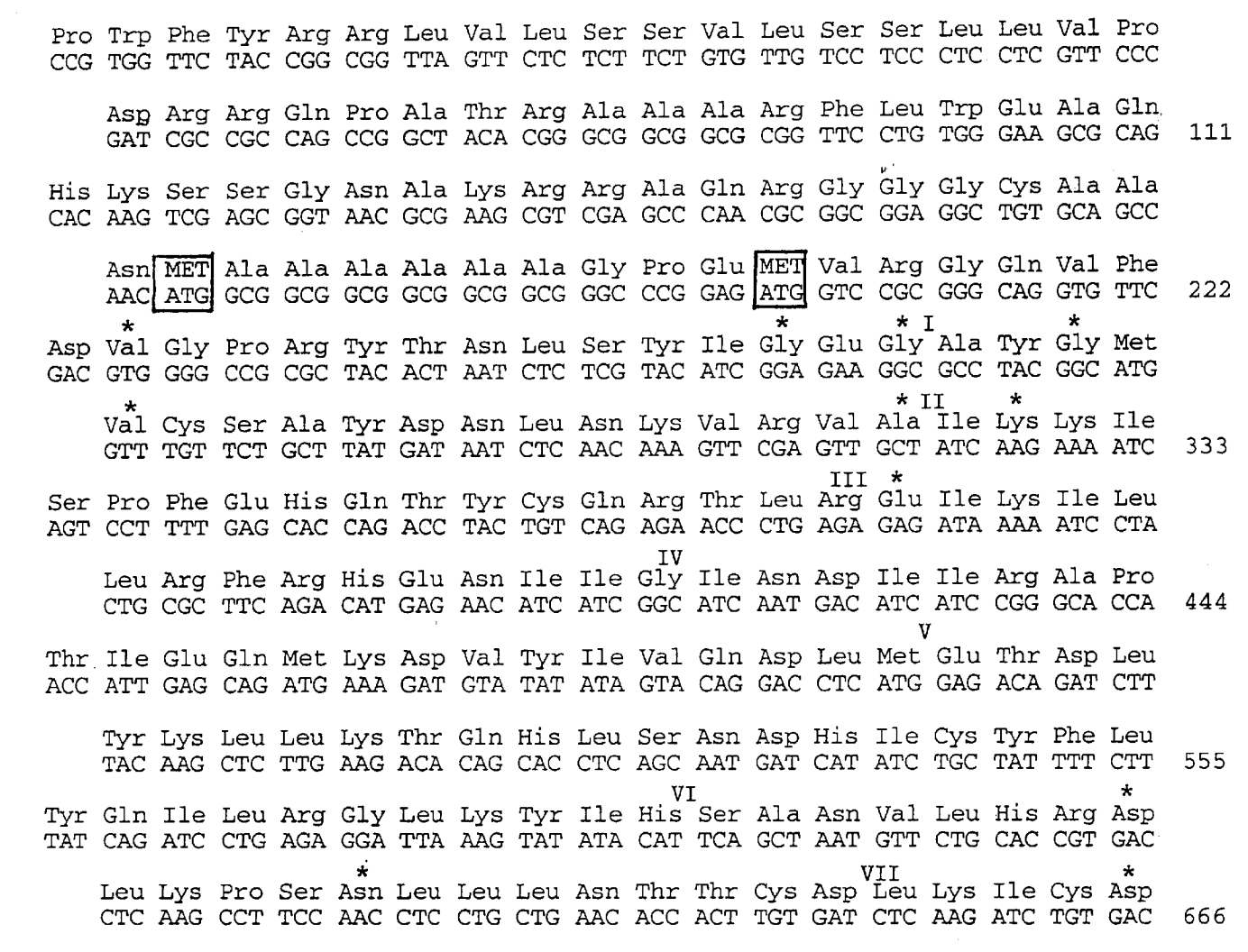

The same probe utilized to isolate the ERK1 cDNA (Boulton et al., 1990, Science 249:64–65) was used to screen a rat brain cDNA library at low-normal stringency, resulting in the identification of multiple hybridizing cDNA clones. Analysis of these clones has led to the discovery of at least two novel protein kinases, which we designate ERK2 and ERK3 (FIGS. 3A (SEQ ID NO:3 AND NO:4) and 3B (SEQ ID NO:5 and NO:6)). ERK1, ERK2 and ERK3 are all more closely related to the yeast kinases, KSS1 and FUS3, than to any other protein kinases (FIGS. 4A and 4B). While the ERKs share approximately 37% (ERK3) to 56% (ERKs 1 and 2) identity with the yeast kinases, they are significantly less related (26% identity for ERK3 and 41% identity for ERKs 1 and 2) to their next closest relatives, the cdc2 family of kinases (Lee and Nurse, 1987, Nature 327:31–35). ERK1 and ERK2 are much more closely related to each other (90% identity) than to ERK3 (FIG. 2B). Using the first in-frame methionine (which satisfies the Kozak consensus for initiation sites (Kozak, 1987, Nucleic Acids Res. 15:8125–8148)), the protein predicted by the ERK2 cDNA has a molecular weight of 41.2 kDa, smaller than ERK1 (~43 kDa), with fewer residues at the amino terminus preceding the catalytic domain. A second in-frame methionine for ERK2 can be aligned with the initiator methionines found in KSS1 and FUS3.

The deduced amino acid sequence of ERK3 predicts a protein of 62.6 kDa. While the initiator methionine is located just downstream of that predicted for ERK2, ERK3 has a C-terminal extension of approximately 180 amino acids compared to ERK1 and ERK2. Despite this long C-terminal extension, ERK3 is notably more related to ERK1 and ERK2 (~50% identity within the catalytic domain) than to its next closest relatives (FIG. 4B). Furthermore, clusters of near identity among the ERKs (e.g. subdomains V-83% identity and VI-95% identity; see FIG. 4A) demonstrate that ERK1 and ERK2 are more closely related to ERK3 than they are to KSS1 and FUS3. Sequencing of two independent cDNA clones confirmed that ERK3 contained SPR rather than APE in subdomain VIII; the glutamic acid in the APE sequence is the only one of the fifteen invariant residues in protein kinases (Hanks et al., 1988, Science 241:42–52) which is not conserved in ERK3. Mutational analysis with the src tyrosine kinase has revealed that a lysine residue substituted for this glutamic acid leads to diminished activity (Bryant and Parsons, 1984, Mol. Cell. Biol. 4:862–866). In subdomain VI, ERK3 SEQ ID NO:6 contains DLKPAN SEQ ID NO:14, a grouping reminiscent of both tyrosine and serine/threonine kinases.

7.2.2. Evidence for Additional ERKs

Figure 3C-1:
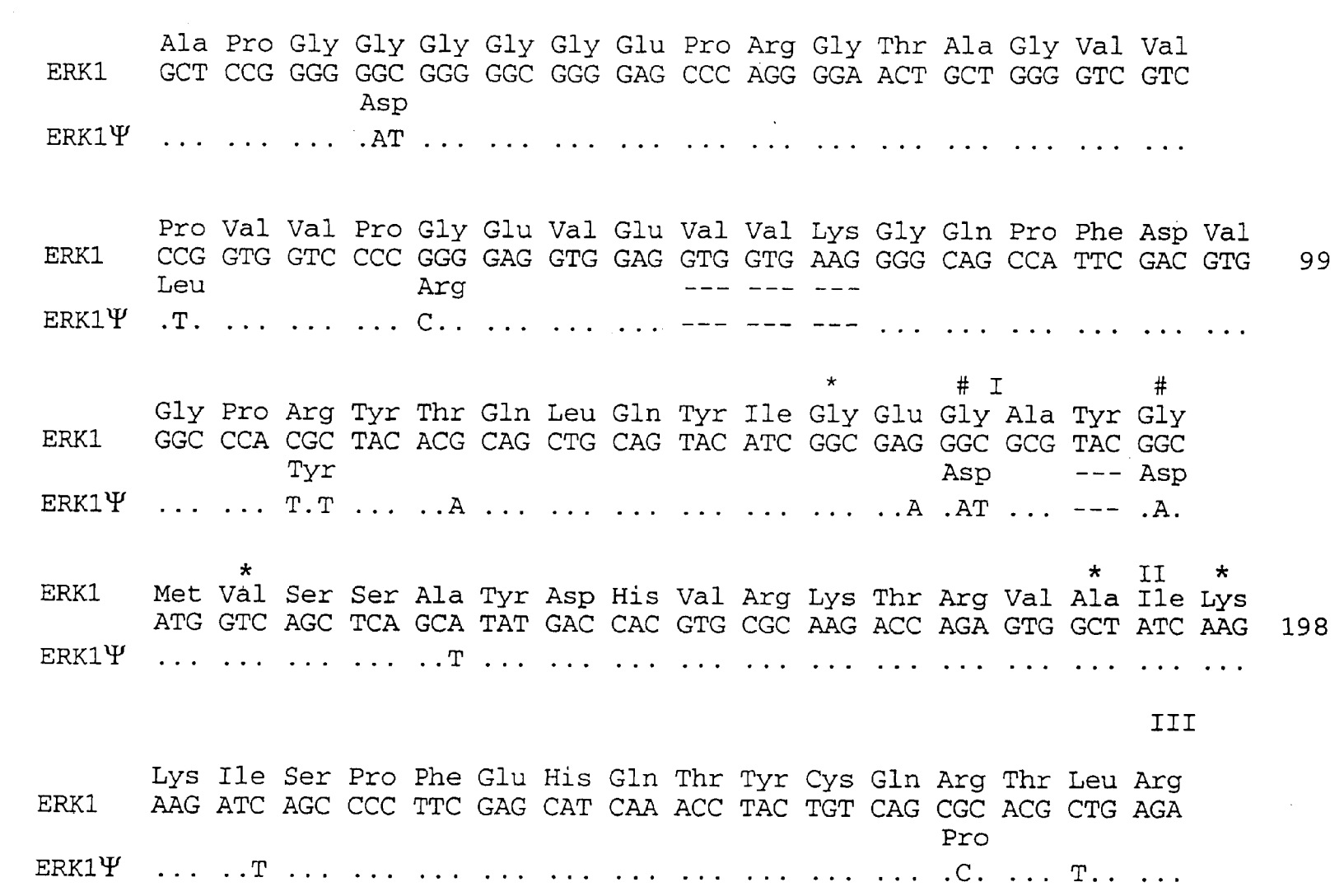
Figure 5A:
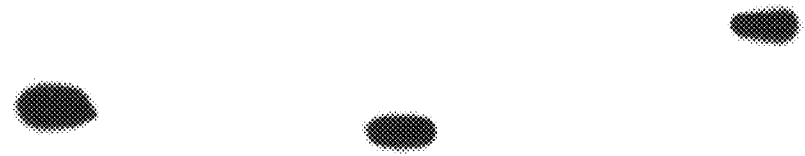
Figure 5B:
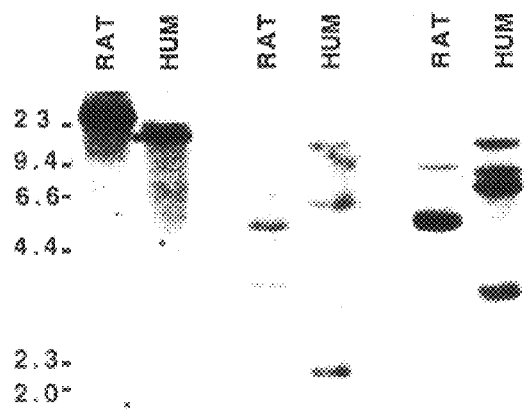
Figure 5C:
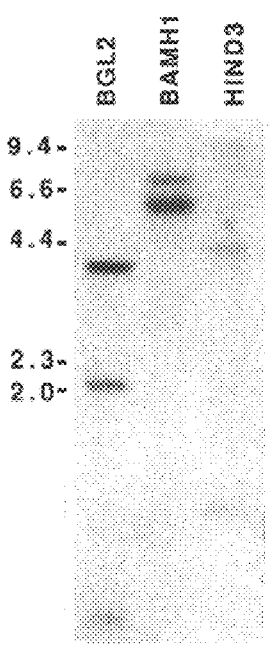

We used probes specific for the individual ERKs (FIG. 5A) to determine whether or not there are additional members of this family. These probes were generated from the least conserved portions of each of the three ERKs (see Materials and Methods) and each probe was shown not to cross hybridize to the other known ERKs (FIG. 5A). The ERK1-specific probe identified a single strongly hybridizing fragment as well as several weekly hybridizing fragments in rat genomic DNA digested with EcoR1, but multiple strongly hybridizing fragments in rat genomic DNA digested with other enzymes (FIGS. 5B and 5C). The ERK2-specific probe identified two distinct EcoR1 fragments in rat genomic DNA and three distinct EcoR1 fragments in human genomic DNA (FIG. 5B). The ERK3-specific probe identified two fragments in rat genomic DNA and four fragments in human genomic DNA (FIG. 5B). Because these probes did not span any introns or contain any of the restriction sites used in the analysis (see Naterials and Methods), these hybridizations suggest that there are multiple ERKs in addition to those already isolated and that the ERKs may be further grouped into subfamilies. Screening rat genomic and cDNA libraries with the ERK-specific probes further supports the idea of subfamily members due to the isolation of a number of clones that hybridize only to one of the specific probes, but only at low-normal stringency. However, these may not all represent functional genes because partial nucleotide sequence of one of the genomic clones reveals that it contains a pseudogene closely related to ERK1 (designated ERK1Ψ, FIG. 3C).

7.2.3. Distinct Developmental and Tissue Distributions of ERKs

Figure 6A:
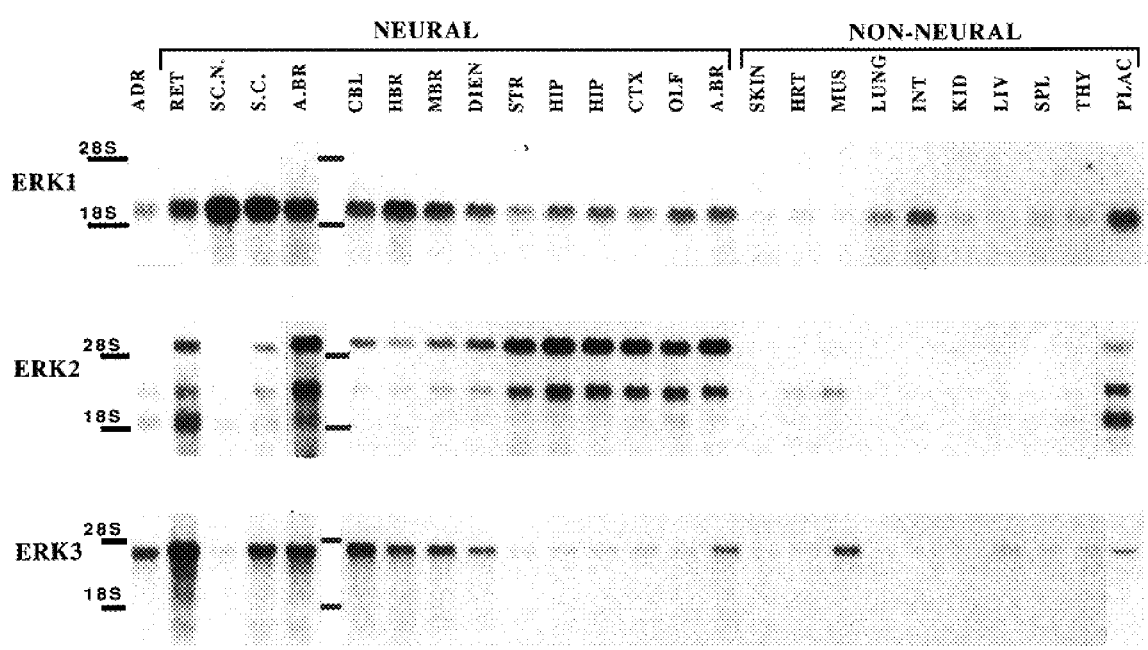

The ERK1-, ERK2-, and ERK-3 specific probes were used to determine the developmental and tissue distributions of ERK mRNA expression. In the adult rat all three ERK mRNAs were expressed at highest levels within the nervous system, although all the mRNAs were detectable in all tissues examined (FIG. 6A). Within the nervous system ERK2 and ERK3 displayed a clearly reciprocal pattern of mRNA expression, with higher ERK3 expression in hindbrain regions and higher ERK2 expression in forebrain regions; by comparison ERK1 was expressed more uniformly. Outside of the nervous system, each of the ERKs was expressed at highest amounts in different tissues. ERK1 was expressed at highest levels in intestine and placenta and to a lesser extent in lung. ERK2 mRNA was expressed at highest levels in muscle, thymus, and heart. The ERK2 probe identified three distinct transcripts, which were expressed at different ratios in different tissues; these transcripts may be differentially processed forms of the ERK2 mRNA or may arise from other genes in the ERK2 subfamily. ERK3 mRNA was expressed at highest levels in skeletal muscle.

Figure 6B:
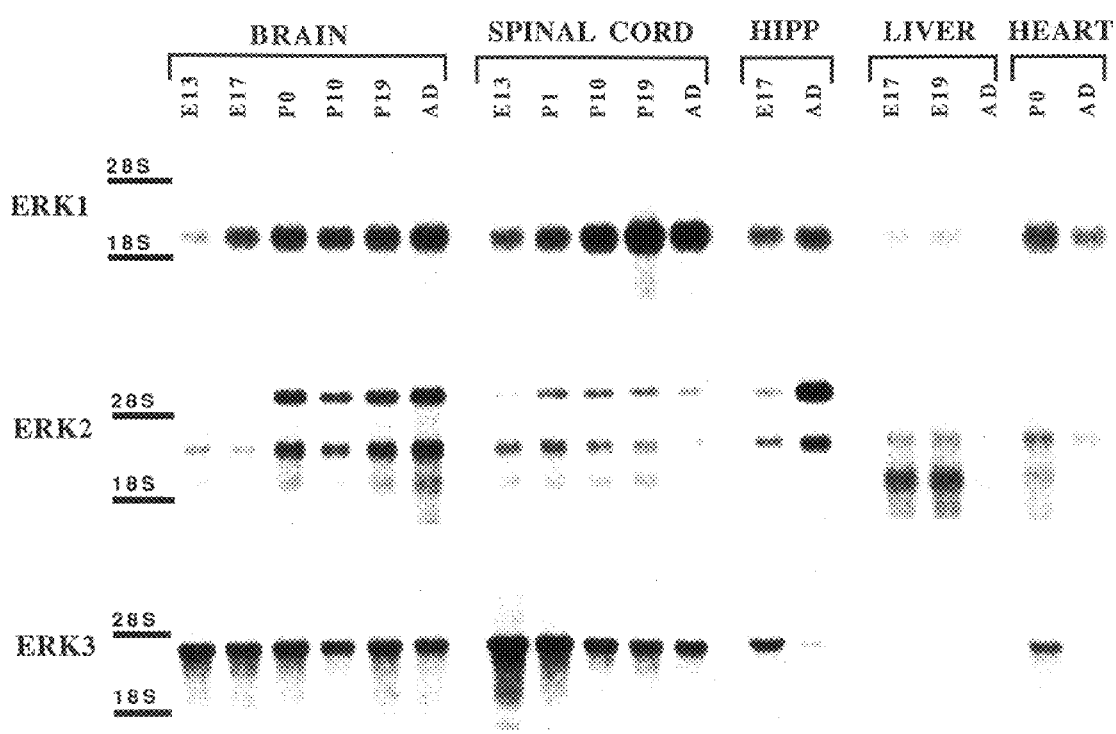

A developmental study of the expression of ERK1, ERK2, and ERK3 within the nervous system revealed that ERK3 mRNA was expressed at highest levels early in development (especially in spinal cord and hippocampus), while the expression of ERK1 and ERK2 mRNAs generally increased during development (FIG. 6B). The developmental increases in the mRNAs for two of these kinases within the brain reflected changes in the amounts of ERK1 and ERK2 protein (see below). In liver and heart the expression of all three ERKs decreases in the adult rat (FIG. 6B). The discrete distributions and developmental patterns of the ERKs suggest that they play unique physiological roles in different cells or perhaps in response to different repertoires of signals.

Figure 6C:
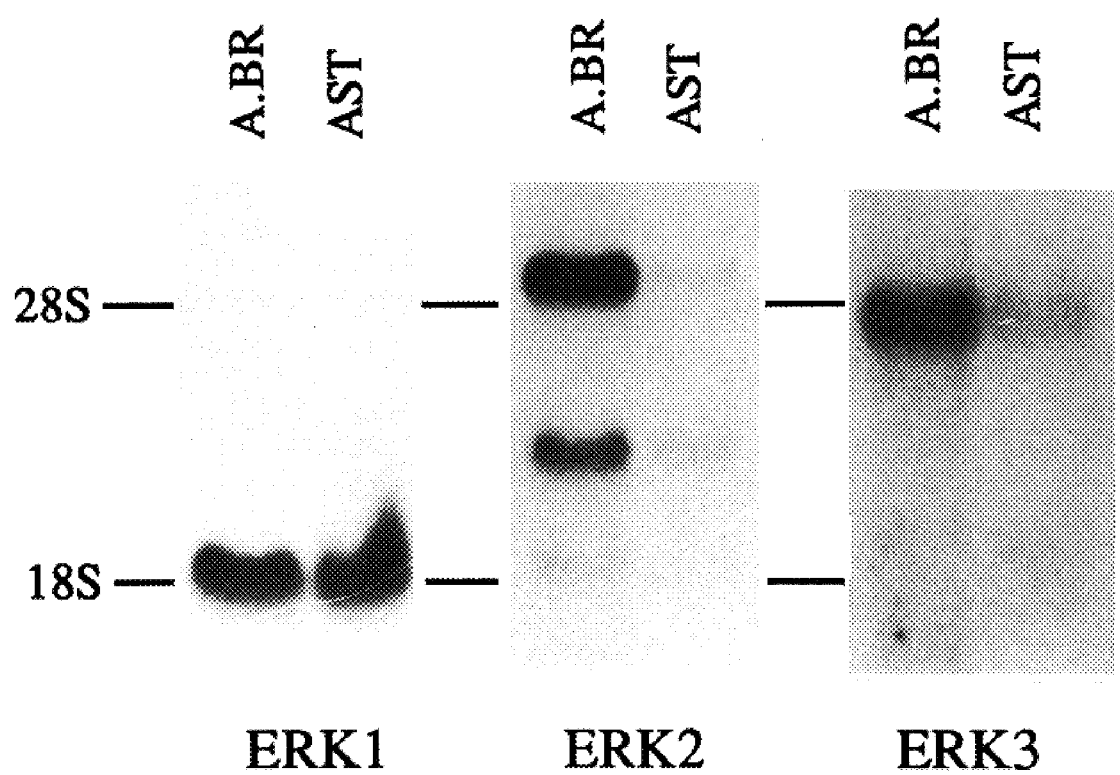

The low levels of ERK2 and ERK3 transcripts in sciatic nerve (which contains neuronal axons and neuron-supporting cells (glia), but lacks neuronal cell bodies and thus neuronal-specific mRNA) contrasts with the high levels of ERK1 mRNA in this peripheral nerve (FIG. 6A). Thus, the high levels of ERK2 and ERK3 in the brain as opposed to peripheral nerve might reflect specific expression within neurons. To further explore this possibility, the level of each of the ERKs was compared in whole brain and in neuron-free glial cultures derived from newborn brains (FIG. 6C). The decreased level of ERK2 and ERK3 expression compared to ERK1 expression in these cultures further indicates that neuronal specificity of ERK2 and ERK3.

7.2.4. Distinct Regulation of Transcripts upon Induction of Neuronal or Muscle Differentiation in Embryocarcinoma Cells The embryonal carcinoma line P19 normally displays an undifferentiated phenotype, but can be induced to differentiate into neuronal muscle lineages following treatment with retinoic acid (RA) or dimethylsulfoxide (DMSO), respectively (McBurney et al., 1982, Nature 2999:165–167). Transcripts hybridizing to the three ERK probes are each uniquely regulated during P19 differentiation. While ERK1 transcripts display no or a slight decrease upon induction towards either neuronal or muscle-like phenotypes, the ERK2 transcripts display a notable increase only upon neuronal induction (which parallels the pattern seen for the low affinity NGF receptor) and the ERK3 transcripts increase upon differentiation toward either the neuronal or muscle lineage. These expression patterns upon differentiation parallel the specific distributions each of the ERRS display in vivo (see above), and provide additional support for the neuronal (rather than glial) specificity of both ERK2 and ERK3. Thus, the P19 differentiation system appears to be a useful model system for studying the roles of individual ERKs during neuronal and muscle differentiation. Interestingly MAP2, which may represent a normal substrate for at least some of the ERKS, is apparently required for important features of the P19 neuronal differentiation process such as neurite extension and cessation of proliferation (Dinsmore and Solomon, 1991, Cell 64:817–826).

7.2.5. Activity of Recombinant ERK2

To begin to compare the properties of the novel ERKs with those of ERK1 purified from insulin-treated fibroblasts (Boulton et al., 1991, Biochem. 30:278–286), we purified recombinant ERK2 synthesized in E. coli (FIG. 7A). Purified recombinant ERK2 phosphorylated itself (FIG. 7C) and the exogenous substrates MAP2 and MBP in a time—(FIG. 7D) and concentration-dependent manner. The specific activities of two preparations of purified recombinant ERK2 were 0.6 and 1 nmol/min/mg of protein with either MAP2 or MBP as substrates. This compares to a specific activity with MAP2 of 300 nmol/min/mg for a highly purified preparation of ERK1 and 4 nmol/min/mg for the same ERK1 preparation which had been exhaustively dephosphorylated with the catalytic subunit of phosphatase 2a. The fact that recombinant ERK2 has a specific activity similar to that of dephosphorylated native ERK1 suggests that the recombinant protein is in the appropriate conformation to be activated by phosphorylation.

7.2.6. Antisera can Distinguish ERK1 and ERK2 and Identify a Novel ERK

Figure 8B:
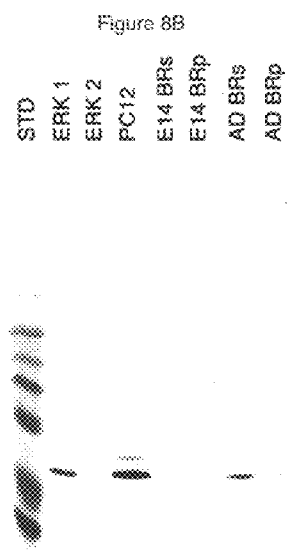
Figure 8C:
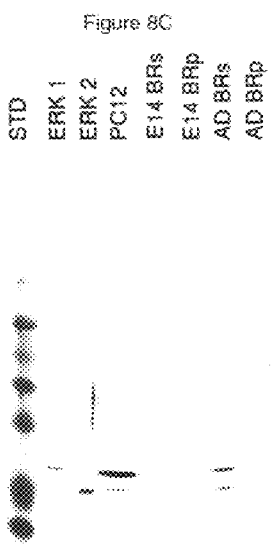

Two different polyclonal antisera, both raised against a peptide consisting of the 16 C-terminal residues of ERK1 (of which 10 are conserved in ERK2), were able to distinguish between purified ERK1 and recombinant ERK2 on immunoblots and could also identify these proteins as well as a novel ERK in crude cell extracts. Antiserum 837 recognized both purified ERK1 and recombinant ERK2 (FIG. 7B), and also identified two proteins of similar sizes in crude brain extracts (FIG. 8C). Antiserum 956 recognized purified ERK1 but not recombinant ERK2; in crude brain extracts this antiserum recognized a protein comigrating with purified ERK1 as well as a novel ERK of 45 kDa (FIG. 8B). Antibodies raised against peptides from other subdomains of ERK1 also recognized all three of these proteins (Boulton and Cobb, May 1991, in Cell Regulation, Vol. II) verifying the identification of ERK1 and ERK2 and confirming the existence of a novel 45 kDa ERK. By immunoblotting, the amounts of both the 43 and the 41 kDa proteins increased dramatically (FIGS. 8B and 8C) in adult brain compared to embryonic brain, paralleling the developmentally regulated increase in accumulation of mRNAs for ERK1 and ERK2 in brain. Based on the specificities of the antisera for the purified ERKs as well as the correlations between amounts of protein and mRNA, we have designated the 43 kDa protein recognized in crude brain extracts by both antisera as ERK1, the 41 kDa protein recognized only by antiserum 837 as ERK2, and the novel 45 kDa ERK as ERK4.

7.2.7. ERKs are Phosphorylated in Response to Insulin and NGF

It has been reported that a protein cochromatographing with MAP kinase activity was phosphorylated on threonine and tyrosine residues in response to insulin (Ray and Sturgill, 1988, Proc. Natl. Acad. Sci. U.S.A. 85:3753–3757). Both types of phosphorylation may be required for maximum MAP2 kinase activity (Anderson et al., 1990, Nature 343:651–653; Ahn et al., 1990, J. Biol. Chem. 265:11495–11591; Gomez et al., 1990, FEBS Lett. 271:119–122; Boulton and Cobb, 1991, Cell Regulation, In press). We utilized our antibody reagents that specifically identify individual ERKs to explore the activation and phosphorylation state of individual members of this kinase family in response to two different growth factors, insulin and NGF.

Figure 9A:
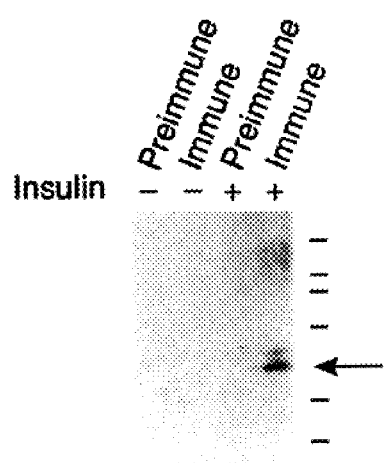
Figure 9A:
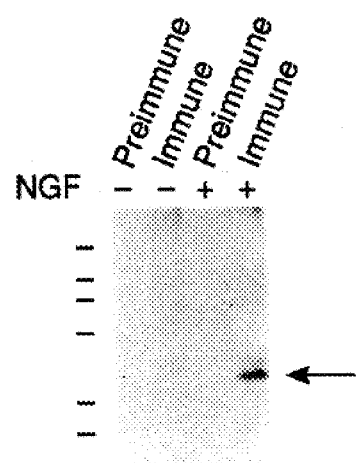
Figure 9B:
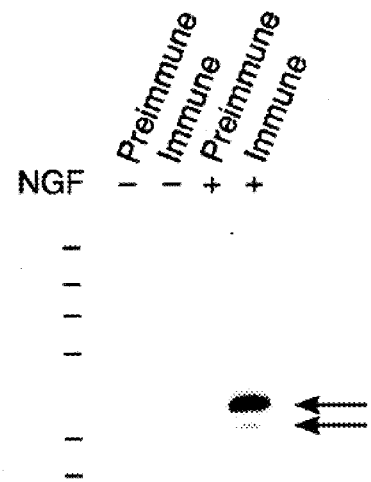

To examine the effect of insulin and NGF on ERK1 phosphorylation directly, we used antiserum 837 to immunoprecipitate ERK1 from $^{32}$P-labeled Rat 1 HIRcB or PC126 cells before and after insulin or NGF stimulation (FIG. 9A). Although antiserum 837 recognized ERK1, ERK2, and ERK4 on immunoblots under denaturing conditions, it immunoprecipitated the 43 kDa ERK1, a small amount of the kDa ERK4, but not the 41 kDa ERK2 from crude extracts under nondenaturing conditions. No $^{32}$P-labeled bands were detected in immunoprecipitates from untreated cells, while $^{32}$P-labeled ERK1 (43 kDa) and a small amount of $^{32}$P-labeled ERK4 (45 kDa) were immunoprecipitated from both insulin-treated or NGF-treated cells, indicating that there is hormone-dependent phosphorylation of both of these ERKs (FIG. 9A). Under denaturing conditions small amounts of labeled ERK2 were also detectably precipitated following stimulation by NGF (FIG. 9B) indicating that ERK2, like ERK1 and ERK4, underwent hormone-dependent phosphorylation.

Figure 9C:
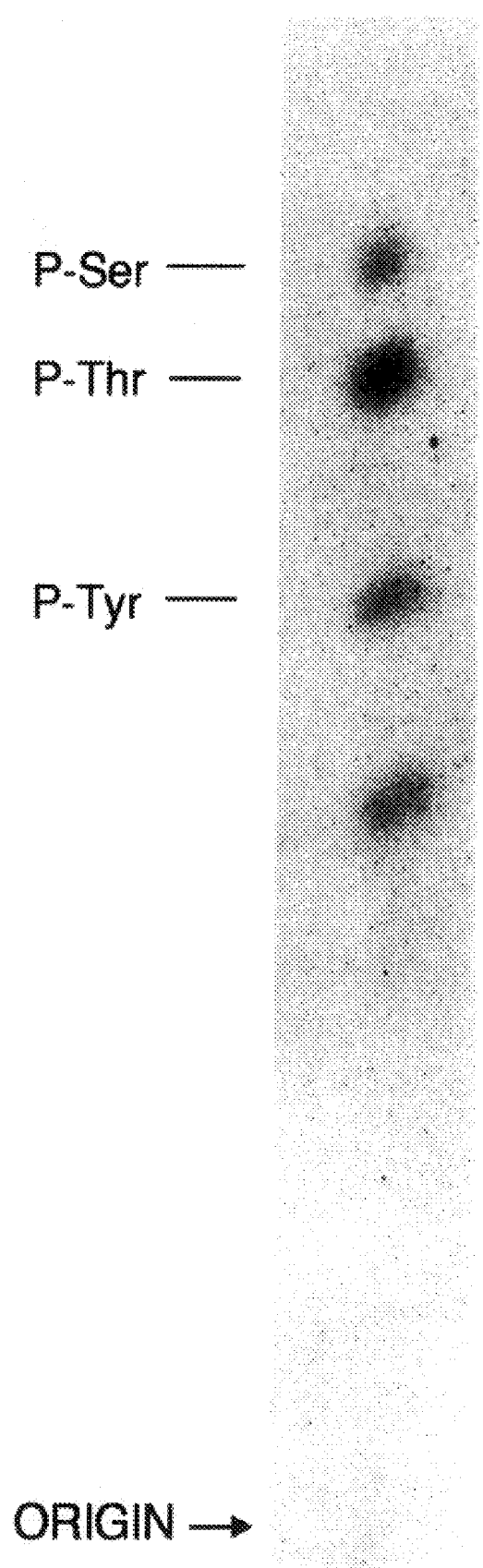

To determine if these phosphorylations include tyrosine, both phosphoamino acid analysis and phosphotyrosine immunoblotting were performed on immunoprecipitated ERKs. When duplicate immunoprecipitates (performed on Rat 1 HlRcB cells under denturing conditions (see Methods)) were immunoblotted with ERK antibodies as well as antibodies to phosphotyrosine, it was evident that both ERK1 and ERK2 from insulin-stimulated extracts contained phosphotyrosine, while there was little detectable phosphotyrosine on the proteins from the unstimulated cells (FIG. 10). No phosphotyrosine was detected on the ERK4; this could be due to our inability to detect it with the antibodies because so little of this protein was immunoprecipitated; alternatively, the hormone-induced increase in phosphate on ERK4 may be only on serine/threonine residues. Phosphoamino acid analysis of $^{32}$P-labeled 43 kDa ERK1 excised from the gel of FIG. 9A revealed that threonine, serine, and tyrosine were phosphorylated in response to NGF (FIG. 9C). The same was true for ERK1 from insulin-treated cells. These findings demonstrate that at least three ERK proteins are phosphorylated in response to insulin and NGF and at least two of these contain phosphotyrosine.

7.2.8. Relationship Between Phosphorylation and Activation of ERKS in Response to NGF To relate the phosphorylation of these proteins to their activities following NGF stimulation, we located ERK1 and ERK2 on immunoblots from Mono Q profiles of untreated and NGF-treated PC12 cells using antisera 956 and 837. NGF treatment resulted in a shift of elution of a portion of both ERK1 (from fractions 29–31 to fractions 38–41) and apparently also ERK2 (from fractions 25–27 to fractions 29–31) (FIG. 11), presumably due to changes in the phosphorylation of these proteins. Identical immunoblots probed with antiphosphotyrosine antibodies revealed little to no phosphotyrosine on ERK1 or ERK2 before NGF treatment. NGF treatment resulted in increased phosphorylation of tyrosine residues on both ERK1 and ERK2. Phosphotyrosine was detectable in both unshifted and shifted ERK1 protein, suggesting that multiple modifications (such as further phosphorylations on tyrosine, threonine, and/or serine residues, which would be consistent with the phosphoamino acid analysis of immunoprecipitated ERK1 described above) are required to retard elution from Mono Q. Analysis of bands from insulin-treated cells on the same gel indicated that the ERK-crossreacting and phosphotyrosine-containing bands comigrate.

NGF treatment also resulted in two major peaks of MBP kinase activity in the Mono Q profile that were not present in the profile from untreated cells. The first peak of activity coeluted with the shifted ERK2 protein (but also overlapped with the unshifted ERK1 protein), while the second peak coeluted with the shifted ERK1 protein. The first peak of MBP kinase activity was not immunoprecipitable with antiserum 837, unlike the second peak. Further, some activity from the first peak could be precipitated with an antibody to recombinant ERK2 that has a limited ability to immunoprecipitate ERK2, but none could be precipitated from the second peak. In addition, activity from both peaks could be inactivated by both the serine/threonine-selective phosphatase 2a and by the tyrosine-selective phosphatase CD45 (Boulton and Cobb, May 1991, in Cell Regulation, Vol. II). Thus, these observations support the conclusion that activity in the second peak is due to fully modified ERK1 and that in the first peak is due to activated ERK2 and not to partially modified ERK1. Altogether, the data indicate that ERK1 and ERK2 are rapidly activated in response to extracellular signals such as insulin and NGF, and that this activation is correlated with increased tyrosine phosphorylation, but that full activation requires additional modifications.

7.3. Discussion

We have compared the sequences of three members of the ERK family. Hybridizations to genomic rat and human DNA (which define a minimum of 3 new ERK genes in addition to ERKs 1, 2, and 3 in rat), screening of genomic and cDNA libraries, and immunoblotting with ERK specific antisera (which define at least one novel ERK in addition to ERK2 and ERK3) suggest that there are additional ERK genes in rat and perhaps even more in human. There is evidence for stimulation of MAP2/MBP Kinase activity in different cell types in response to a variety of signals; there is even more extensive evidence for tyrosine phosphorylation of 40–45 kDa proteins in response to cellular stimulation (cooper and Hunter, 1981, Mol. Cell. Biol. 1:165–178; Maytin et al., 1984, J. Biol. Chem. 259:12135–12143; Cooper et al., 1984, Mol. Cell. Biol. 4:30–37; Martinez et al., 1982, Mol. Cell. Biol. 2:653–685; Cooper et al, 1982, Cell 31:263–273; Roassomando et al., 1989, Proc. Natl. Acad. Sci. U.S.A. 86:6940–6943; Ferrell and Martin, 1990, Molec. Cell. Biol. 10:3020–3025; Gold et al., 1990, Nature 345:810–813). Our results indicate that the MAP2/MBP Kinase activity measured in extracts from insulin- and NGF-stimulated cells is derived not from a single enzyme but from at least two different protein kinases, ERK1 and ERK2. These data are consistent with our findings that suggest an extended family of ERK-related enzymes in rat. We conclude that similar activities found in other types of cells in response to other stimuli could be due to ERK1 or ERK2 alone, to both enzymes, or perhaps to other members of this family. The first three characterized members of this family were isolated from a brain cDNA library and are found at highest levels within the nervous system, although the expression of each ERK displays distinct tissue and developmental regulation. Screening of libraries from other tissues may yield ERKs that function predominantly in non-neural tissues.

The kinases next most closely related to the ERKs are the products of the KSS1 (Courchesne et al., 1989, Cell 58:1107–111) and the FUS3 (Ellon at al., 1990, Cell 60:649–664) genes previously cloned from yeast. KSS1 overcomes mating factor-induced growth arrest. In contrast FUS3 leads to the arrest of the cell cycle in response to mating factors. Because of regions of new identity among all three ERKS, it seems likely that they evolved from a common precursor. The relationship between the ERKs and their yeast relatives suggests that multicellular higher eukaryotes have appropriated kinases, originally utilized by primordial mating responses in unicellular organisms, to mediate responses to extracellular signals. Furthermore, the cdc2 kinases, which are the next closest relatives of the ERKS, apparently play similar roles in regulating the cell cycle in eukaryotes as diverse as yeast and man. Intriguingly, as in the case with the ERKs, the cdc2 kinases are also regulated (albeit negatively) by phosphorylation on both tyrosine and threonine.

Understanding signal transduction requires elucidating the mechanisms by which receptor-activated tyrosine phosphorylation is converted into the serine/threonine phosphorylations that regulate downstream targets. We have defined a family of serine-threonine protein kinases, the ERKS, with members that are activated and phosphorylated on tyrosine residues in response to NGF and insulin. The initiation of the series of events culminating in activation of the ERKs by insulin and NGF may occur via distinct receptors; however, both hormones are known to elicit tyrosine phosphorylation. While the insulin receptor has been recognized to contain intrinsic tyrosine kinase activity for several years, it is still unclear how activation of the NGF receptor elicits intracellular tyrosine phosphorylation. Recent evidence suggests that the NGF receptor may either contain tyrosine kinase activity (Kaplan et al., 1991, Nature 350:158–160) or is associated with such protein (Neakin and Shooter, 1991, Neuron 6:153–163). Whatever mechanisms may be involved, phosphorylation of the ERKs represents the first example of defined intracellular proteins which are phosphorylated on tyrosine in response to NGF.

Our findings suggest that a characteristic property of this family of kinases is to serve as intermediates that depend on tyrosine phosphorylation to activate serine/threonine phosphorylation cascades in response to a wide variety of extracellular signals, although it is still unclear whether the ERKs are direct substrates for receptor-associated tyrosine kinases, or whether they are further downstream in cascades. Delineating the involvement of individual ERKs in phosphorylation networks, and how they might act combinatorially, may be necessary to determine how different cell types produce the complex array of responses to the many extracellular signals that activate tyrosine phosphorylation. For example, the same signal acting through the same receptor, during different developmental stages or in different cell types, can generate dissimilar responses (e.g., proliferation vs. differentiation). Activation of specific ERKs in different contexts may contribute to multiple interpretations of the same signal or common responses to different signals. The observation that the three kinases are differentially expressed in tissues during development and the finding that ERKs 2 and 3 are induced in a model system for neuron development while ERK1 is lost during this process, further support the notion that these enzymes play unique roles in signal transduction pathways recruited during development. Furthermore, deregulation of such potentially important signalling molecules might be involved in cellular transformation and oncogenesis.

The cloning of the ERK genes and the identification of a differentiating cell line in which they are independently regulated may be used in elucidating the role of the ERKs in phosphorylation cascades, and to reveal the mechanisms involved in regulating this family of kinases. Expression of recombinant ERK proteins and their mutants may be used to define the roles of these kinases in vivo and to determine residues involved in ERK function and activation. Antibodies to common and unique regions of the ERKs may facilitate examination of how individual members participate in various responses. The indication from Mono Q profiles that both active and inactive ERK1 contains phosphotyrosine upon stimulation suggests that the extent of ERK1 activation is also determined by threonine/serine phosphorylation. The large increase in MBP kinase activity induced by okadaic acid (Haystead et al., 1990, J. Biol. Chem. 265:16571–16580), is consistent with this notion. The availability of recombinant proteins may be used to dissect the roles of both serine/threonine and tyrosine phosphorylation in ERK activation. In this regard, recombinant ERK2 has activity similar to dephosphorylated native ERK1, suggesting that the recombinant protein may be in the appropriate conformation to be activated by phosphorylation. In fact, experiments show that the activity of dephosphorylated ERK1 is increased to the specific activity of the purified active protein and the activity of recombinant ERK2 is increased 150-to 200-fold by an EGF-sensitive activator recently described by Ahn et al., 1991, J. Biol. Chem. 266:4220–4227). The ability to activate recombinant ERK2 in vitro verifies the utility of recombinant ERK proteins to search for shared or unique substrates, activators (e.g. serine/threonine and tyrosine kinases) and inactivators (e.g., phosphatases).

8. Deposit of Microorganisms

Various references are cited herein, the disclosures of which are incorporated by reference in their entireties.

The following plasmids and cell line were deposited with the American Type Culture Collection in 10801 University Boulevard, Manassas, Va. 20110-2209.

|  | Accession No. | Date of Deposit |
|---|---|---|
| Cell line Rat 1 HIRc B | CRL 10476 | May 31, 1990 |
| Plasmid pBS-rERK1 | 40808 | May 23, 1990 |
| Plasmid pBS-rERK2 | 40809 | May 23, 1990 |
| Plasmid pBS-rERK3 | 75009 | May 14, 1991 |

The present invention is not to be limited in scope by the constructs deposited or the embodiments disclosed in the examples, which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the scope of the appended claims.

Various references are cited herein, the disclosures of which are hereby incorporated by reference in their entireties.

What is claimed is:

1. A purified MAP2 protein kinase comprising an amino acid sequence as set forth in SEQ ID NO:2.

2. The purified MAP2 protein kinase of claim 1, having an amino acid sequence as set forth in SEQ. I.D. No. 2.

3. A purified MAP2 protein kinase designated ERK1 encoded by a nucleic acid molecule selected from the group consisting of:

(a) a nucleic acid molecule comprising a nucleotide sequence as set forth in SEQ ID NO:1; and (b) a nucleic acid molecule comprising a nucleotide sequence that, as a result of the degeneracy of the genetic code, differs from the nucleotide sequence of (a) and encodes the MAP2 protein kinase designated ERK1 as set forth in SEQ ID NO:2.

4. A purified MAP2 protein kinase designated ERK1 encoded by the plasmid designated pBS-rERK1 (ATCC® Accession No. 40808).

* * * * *